United States Patent
Chauvier et al.

(10) Patent No.: US 8,173,600 B2
(45) Date of Patent: *May 8, 2012

(54) CASPASE-2 INHIBITORS AND THEIR BIOLOGICAL APPLICATIONS

(75) Inventors: David Chauvier, Chatillon (FR);
Richard Casimir, Bischeim (FR);
Etienne Jacotot, Paris (FR); Dominique Rebouillat, Paris (FR)

(73) Assignee: Chiesi Farmaceutici S.p.A., Parma (IT)

( * ) Notice: Subject to any disclaimer, the term of this patent is extended or adjusted under 35 U.S.C. 154(b) by 445 days.

This patent is subject to a terminal disclaimer.

(21) Appl. No.: 11/579,202

(22) PCT Filed: May 2, 2005
(Under 37 CFR 1.47)

(86) PCT No.: PCT/EP2005/005493
§ 371 (c)(1),
(2), (4) Date: May 19, 2008

(87) PCT Pub. No.: WO2005/105829
PCT Pub. Date: Nov. 10, 2005

(65) Prior Publication Data
US 2008/0311051 A1      Dec. 18, 2008

Related U.S. Application Data

(60) Provisional application No. 60/566,589, filed on Apr. 30, 2004, provisional application No. 60/659,219, filed on Mar. 8, 2005.

(51) Int. Cl.
*A61K 38/08* (2006.01)
*A61K 38/55* (2006.01)
*C07K 7/06* (2006.01)

(52) U.S. Cl. ............... 514/18.9; 514/20.2; 514/21.8; 530/330

(58) Field of Classification Search ............ None
See application file for complete search history.

(56) References Cited

U.S. PATENT DOCUMENTS

| | | | |
|---|---|---|---|
| 6,235,493 | B1 | 5/2001 | Bissell et al. |
| 2002/0061853 | A1 | 5/2002 | Golec |
| 2002/0183258 | A1 | 12/2002 | D'Lima et al. |
| 2006/0241034 | A1 | 10/2006 | Chauvier et al. |

FOREIGN PATENT DOCUMENTS

| | | |
|---|---|---|
| WO | WO 86/00075 | 1/1986 |
| WO | WO95/04541 | 2/1995 |
| WO | WO 95/08678 | 3/1995 |
| WO | 97/27220 A | 7/1997 |
| WO | 02/24720 A | 3/2002 |
| WO | 2004/103389 A | 12/2004 |

OTHER PUBLICATIONS

Jin et al. Two caspase-2 transcripts are expressed in rat hippocampus after global cerebral ischemia. Journal of Neurochemistry. 2002, vol. 81, pp. 25-35.*
Letter to the Editor "Broad-spectrum caspase inhibitors: from myth to reality?", Cell Death and Differentiation (2006) 00, 1-4.
R&D Systems, Caspase-2 Inhibitor, Z-VDVAD-FMK, catalog No. FMK003, published on the internet on Jun. 18, 1999, 1 page.
R&D Systems, Caspase-2-Fluorometric Assay, catalog No. BF5100, published on the internet on Jan. 28, 2002, 2 pages.
Andersson et al, "Caspase and Proteasome Activity during Staurosporin-Induced Apoptosis in lens Epithelial Cells", IOVS, Aug. 2000, vol. 41, No. 9, pp. 2623-2632.
Huo et al, "Activation of Caspase-2 Mediates the Apoptosis Induced by GTP-Depletion in Insulin-Secretin (HIT-T15) cells", Endocrinology 143(5), pp. 1695-1704, 2002.
Stennicke et al, Caspase Assays, Methods in Enzymology, vol. 322, pp. 91-100 (2000).
File History of EPA 05758395.7, Feb. 26, 2010.
U.S. Appl. No. 12/417,760, filed Apr. 2009, Chauvier et al.
International Search Report of PCT/EP2004/006288, mailed Aug. 26, 2005.
Stefanis et al., "Caspase-2 (Nedd-2) processing and death of trophic factor-deprived PC12 cells and sympathetic neurons occur independently of caspase-3 (CPP32)-like activity", Journal of Neuroscience, Nov. 15, 1998, vol. 18, No. 22, pp. 9204-9215, XP008047225.
Lassus et al., "Requirement for caspase-2 in stress-induced apoptosis before mitochondrial permeabilization", Science, Aug. 23, 2002, vol. 297, No. 5585, pp. 1352-1354, XP001187581.

Droin et al., "Involvement of caspase-2 long isoform in Fas-mediated cell death of human leukemic cells", Blood, Mar. 15, 2001, vol. 97, No. 6, Mar. 15, 2001, pp. 1835-1844, XP008047224.

Bergeron et al., "Defect in Regulation of Apoptosis in Caspase-2-Deficient Mice", Genes and Development, vol. 12, May 1998, pp. 1304-1314, XP000952591.

S. Kumar, "Inhibition of apoptosis by the expression of antisense Nedd2.", FEBS Letters, Jul. 10, 1995, vol. 368, No. 1, pp. 69-72, XP001187587.

Troy et al., "Caspases on the brain", Journal of Neuroscience Research, Jul. 15, 2002, vol. 69, No. 2, pp. 145-150, XP008029695.

International Search Report of PCT/EP2005/005493, mailed Nov. 8, 2005.

Ceruti et al; "A key role for caspase-2 and caspase-3 in the apoptosis induced by 2-chloro-2'-deoxy-adenosine (cladribine) and 2-chloro-adenosine in human astrocytoma cells", Molecular Pharmacology, Jun. 2003, vol. 63, No. 6, pp. 1437-1447, XP002349134.

* cited by examiner

*Primary Examiner* — Jeffrey E Russel

(74) *Attorney, Agent, or Firm* — Nixon & Vanderhye P.C.

(57) ABSTRACT

The invention relates to selective new caspase-2 inhibitors that recognize caspase-2 and prevent and block its activity based on the following backbone: 2-Quinolinylcarbonyl-L-Valinyl-L-Aspartyl (methyl ester)-L-Valinyl-L-Alanyl-L-Aspartyl (methyl ester) 2,6-difluorophenyl ester SEQ ID NO:1) and derivatives thereof, SEQ ID NO:1 corresponding to formulae Ia or Ib. Application of the inhibitors for preventing and treating diseases involving caspase-2.

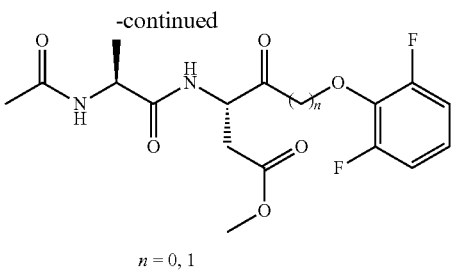

$n = 0, 1$

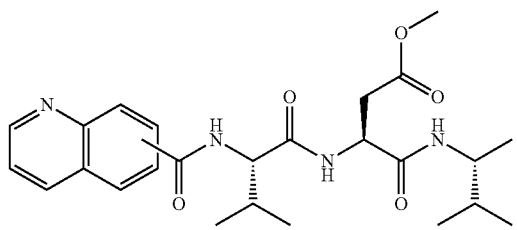

Ib

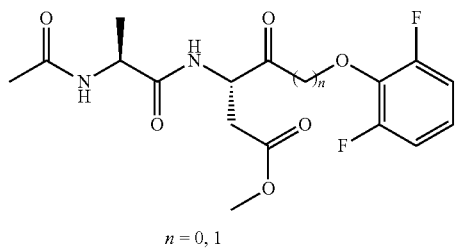

$n = 0, 1$

Ia

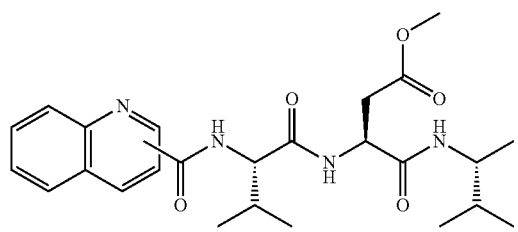

7 Claims, 10 Drawing Sheets

Figure 1:
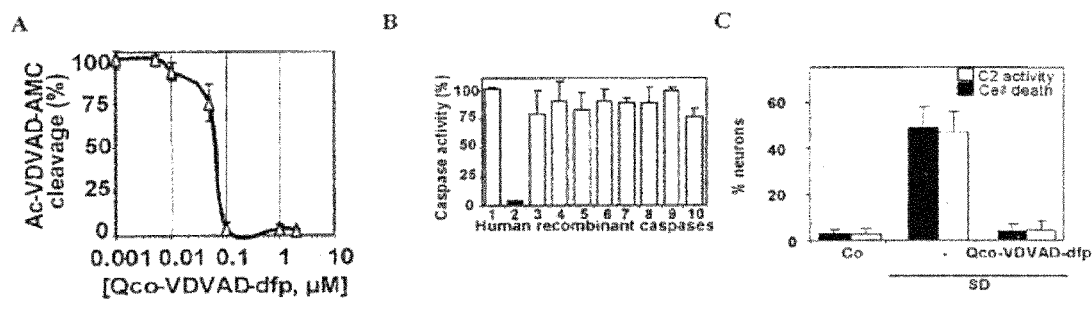

Figure 2
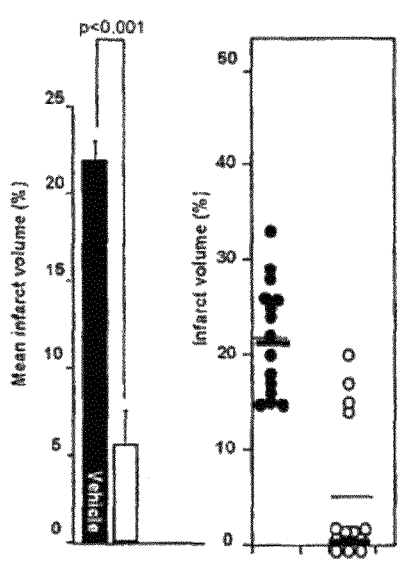
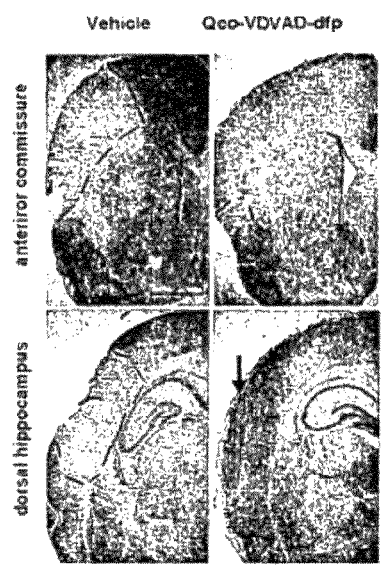
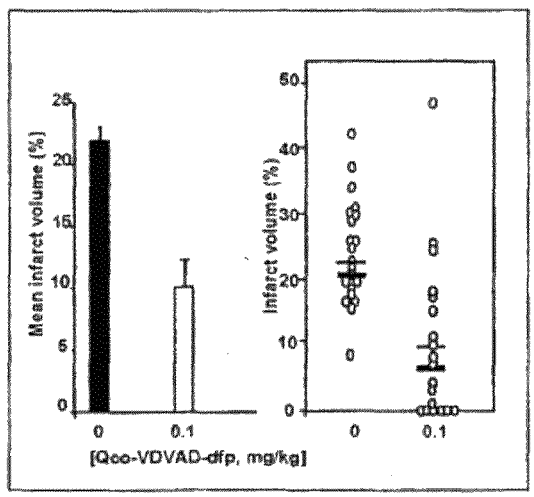
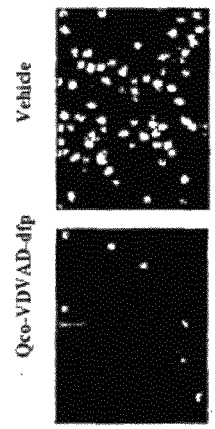
|  | 5 min before ischemia (°C) | 5 min after ischemia (°C) |
|---|---|---|
| Vehicle | 37.21 ± 0.48 | 36.39 ± 0.54 |
| Pre 5 mg/kg | 36.60 ± 0.28 | 36.40 ± 0.67 |
| Post 5 mg/kg | 36.50 ± 0.13 | 35.88 ± 0.21 |
| Post 10 mg/kg | 36.63 ± 0.23 | 35.85 ± 0.18 |
Instrumental precision : +/- 0.4 °C Figure 4
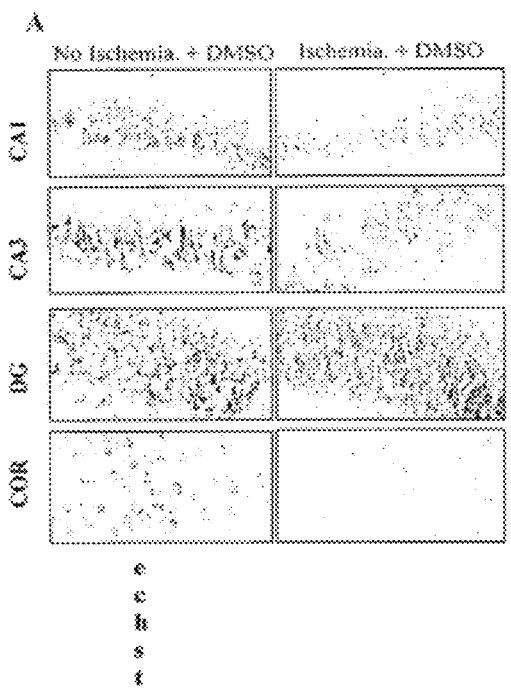
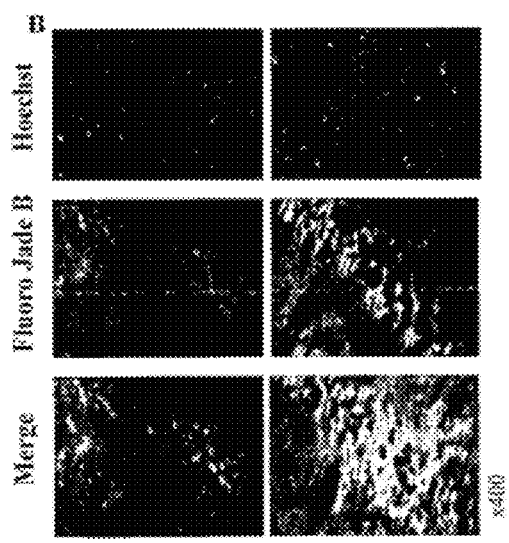
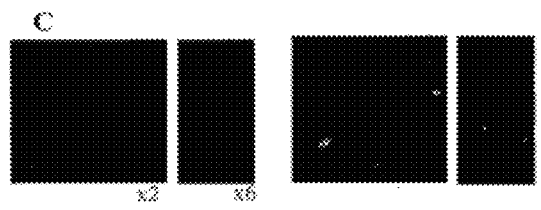
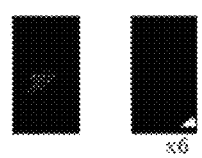

Figure 10
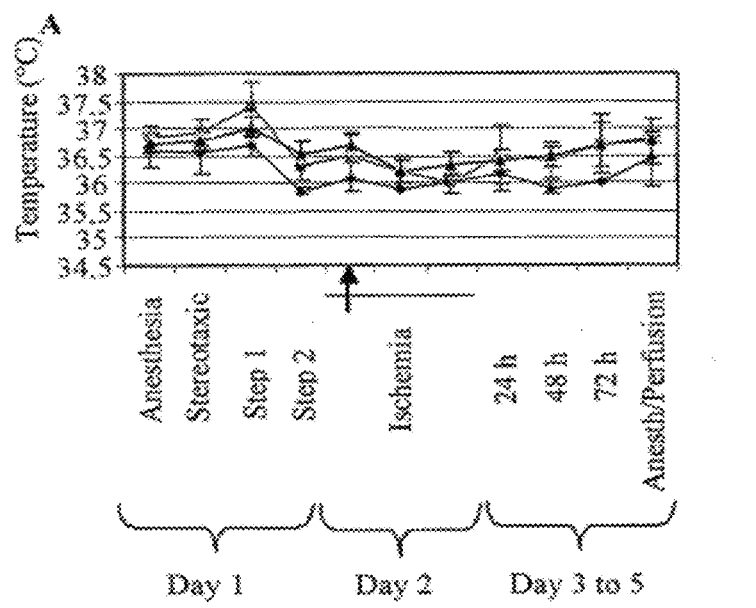
- Isch. + DMSO
- Isch. + Qco-VDVAD-dfp 600 ng
- Isch. + Qco-VDVAD-dfp 60 ng
→ injection
| Parameters | normal score | Isch. + DMSO | Isch. + QcoVDVAD-dfp 600 ng | Isch. + QcoVDVAD-dfp 60 ng |
|---|---|---|---|---|
| Feeding | 1 | 0 | 1 | 1 |
| Spontaneous activity | 1 | 0.5 | 1 | 0.8 |
| Reactivity | 1 | 0.5 | 0.8 | 0.8 |
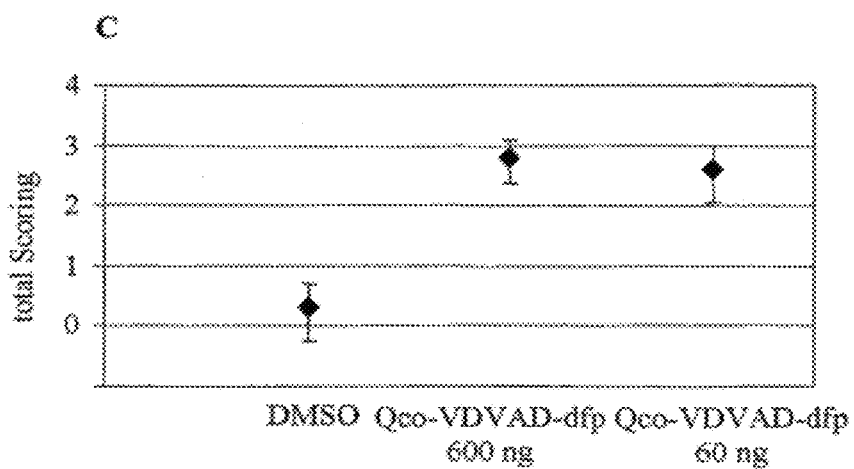

CASPASE-2 INHIBITORS AND THEIR BIOLOGICAL APPLICATIONS

This application is the US national phase of international application PCT/EP2005/005493, filed 2 May 2005, which designated the U.S. and claims priority of U.S. 60/566,589, filed 30 Apr. 2004, and U.S. 60/659,219, filed 8 Mar. 2005, the entire contents of each of which are hereby incorporated by reference.

The invention relates to caspase-2 inhibitors and their biological applications, particularly for the treatment of focal and global cerebral ischemia.

I/ FIELD OF THE INVENTION

The invention is in the field of medicinal biology and chemistry and relates to novel compounds, and pharmaceutical compositions, that inhibit pro-apoptotic caspase-2 (Nedd-2; Ich-1), to treat diseases and injuries where caspase-2 activity is implicated. More precisely:
(a) The invention relates to means, methods and products, for blocking, preventing or treating cell death, particularly in vivo cerebral cell death.
(b) The invention relates to the discovery that caspase-2 is an upstream major checkpoint for inhibition of neuronal cell death (especially apoptosis) in vitro and in in vivo pathological situation including cerebral hypoxia-ischemia (H-I) injuries and stroke-like situations that result in brain damages (in neurons or other non-neuronal cells): for example, MCAO (Middle Cerebral Artery Occlusion), global (as a consequence of blood flow reduction or hypoxia during cardiac arrest or cardiovascular injuries) or focal, transient or permanent, adult or neonatal H-I, ischemia with or without hypoxia and/or hypoglycaemia, H-I with or without reperfusion.
(c) The invention relates to the discovery that selective caspase-2 inhibitors (for example, Qco-VDVAD-dfp (SEQ ID NO:1)) prevents or decreases in vivo cerebral cell death
(d) The invention relates to the discovery that selective caspase-2 inhibitors (for example, Qco-VDVAD-dfp (SEQ ID NO:1)) prevents or decreases cerebral cell death in in vivo pathological situations including ischemic injuries following focal transient neonatal H-I
(e) The invention relates to the discovery that selective caspase-2 inhibitors (for example, Qco-VDVAD-dfp (SEQ ID NO:1)) prevents or decreases cerebral cell death in in vivo pathological situations including cerebral global adult ischemia following blood flow reduction/hypoxia during cardiac arrest or cardiovascular injuries.
(f) The invention relates to new applications for specific new caspase-2 inhibitors including local (intracerebroventricular, intrahippocampal, . . . for example) delivery or systemic (intraperitoneal, intravenous . . . ) administration to reduce cerebral cell death during pathological situations in which blood flow and oxygen pressure are disturbed, i.e. cerebral (transient or permanent) focal or global ischemia.

II/ DATA SUPPORTING THE INVENTION

The invention relates to means, methods and products, for blocking preventing or treating cell death, particularly neuronal cell death.

Neuronal cell death occurs during embryogenesis to remove excess of neurons to ensure appropriate pre- and post-synaptic connections and to allow formation of a functional adult brain. Besides post-mitotic death related to normal ageing, environmental or genetic mutational factors may induce neuronal death in the adult human during acute injuries (for instance, hypoxia-ischemia, stroke, spinal cord injury, trauma) or chronic neurodegenerative diseases. Cell death associated with these disorders may occur by three distinct mechanisms, exhibiting morphological and biochemical features of necrosis, autophagy or apoptosis. Both physiological and pathological neuronal deaths are often associated with defective apoptosis regulation and signalling pathways that lead to this active cell suicide mechanism may be divided in cysteinyl aspartate-specific protease (caspase)-dependent versus caspase-independent pathways in mammalian cells.

Neuronal apoptosis is an active cell suicide mechanism that can be divided into sequential phases, including initiation, decision, execution, and degradation. This cascade of events is driven by the activation of a specific machinery, that involve both the activation of cysteine-dependent aspartate-specific proteases (caspases) and the mitochondrion which may act as a decisive (or amplifier) regulatory organelle. Indeed, mitochondrial alterations include loss of mitochondrial inner membrane electrochemical gradient ($\Delta\Psi_m$) and release of apoptogenic factors such as cytochrome c, Smac/Diablo and Apoptosis Inducing Factor. Once released from mitochondria, these effectors trigger caspase-dependent and/or caspase-independent cytoplasmic and nuclear dismantling. Hence, mitochondrial factors combined with caspases contribute to the degradation phase of apoptosis, resulting in cell shrinkage, nuclear condensation, emission of apoptotic bodies and appearance of "eat-me" signals such as phosphatidylserines translocation to the outer leaflet of the plasma membrane before phagocytosis.

The respective contribution of mitochondria, caspases and other events during in vitro or in vivo neuronal apoptosis is still not elucidated, particularly with respect to a ischemic or stroke-like_injuries.

As illustrated, the inventors provide useful means and molecules enabling to inhibit caspase-2 activity in vitro and in cellula, by using specific in vitro caspases assays and serum deprivation in neuronal culture as an experimental model relevant to in vivo ischemia.

The selective new caspase-2 inhibitors of the invention, that recognize caspase-2 and prevent and block its activity, are based on the following backbone: 2-Quinolinylcarbonyl-L-Valinyl-L-Aspartyl (methyl ester)-L-Valinyl-L-Alanyl-L-Aspartyl (methyl ester) 2,6-difluorophenyl ester (SEQ ID NO:1)

One preferred molecule corresponds to SEQ ID NO:1.

Other preferred molecules comprise structures II two XIX as indicated, particularly, in Tables 1 to 14.

Another object of the invention is to provide novel products (molecules or formulations) that inhibit pro-apoptotic caspase-2 activity and induce cytoprotection.

Another object of the invention is to provide products and pharmaceutical compositions and methods of treatments of diseases and injuries where caspase-2 is involved.

The inventors have developed pharmacological specific peptides, preferentially but not exclusively pentapeptide-based molecules, for direct inhibition of caspase-2 activity in order to attenuate in vitro and in vivo cell death mediated by caspase-2.

Such inhibitors are capable of preventing or blocking caspase-2 activity in cell death. Said cells are neurons, or neuronal cells, or non neuronal cells.

The above defined inhibitors are useful for in vivo inhibition of caspase-2 activity to provide neuroprotective or cerebroprotective effect. They are also useful for in vivo inhibition of caspase-2 activity to provide cytoprotective effect.

According to one aspect, the invention relates to method for preventing cell death in the brain following (global of focal) ischemic injuries.

As illustrated by the examples, the invention provides means, methods and products, for blocking or preventing or treating cell death, particularly in the injured (ischemic) brain.

As illustrated, the inventors demonstrate that specific caspase-2 inhibitor (single intraperitoneal injected dose) induces important infarct reduction in neonatal transient hypoxia-ischemia brain injury. Infarct volume reduction was obtained when caspase-2 inhibitor administration before or after ischemic onset. Cytoprotective effects provided by the inhibitor are not mediated by temperature (hypo or hyperthermic) regulation. But in vivo caspase-2 activity or caspase-2 processing is abolished after injection of the inhibitor.

As illustrated, the inventors demonstrate that specific intracerebroventricular (ICV) administration of caspase-2 inhibitor (single dose) results in partial increase of Cresyl-Violet intensity staining, absence of Fluoro Jade B intake in damaged cells, an improvement or preservation of nuclear morphology (Hoechst 33342) as well as a considerable improvement in the behaviour of inhibitor-treated rats (refeeding post-ischemia; higher score in tests regarding spontaneous activity and reactivity). Cytoprotective and behavioural effects provided by the inhibitor are not mediated by temperature (hypo or hyperthermic) regulation.

According to another aspect, the invention also relates to molecules capable of preventing caspase-2 activity and pharmaceutical compositions useful for treating diseases and injuries where caspase-2 is involved.

The synthetized molecules are introduced in human or animal, under conditions for caspase-2 inhibition. The introduction step comprises chemical modifications of molecules as suitable carriers or is performed by injection.

Accordingly, this is another object of the invention to provide pharmaceutical compositions containing specific caspase-2 inhibitors.

The pharmaceutical compositions of the invention comprise a therapeutically effective amount of at least one caspase-2 inhibitor as above defined, in association with a pharmaceutically acceptable carrier.

Administration of inhibitors is performed (but is not restricted to) by oral, nasal, local (intracerebroventricular, intrahippocampal, or other intracerebral delivery, intracerebral implantation of instrumentation for mechanical delivery such as of Gelfoam® impregnated with compounds or pharmaceutical compositions, for example) or systemic (intraperitoneal, intravenous . . . ) route, or intracerebral delivery or as aerosol to reduce in vivo cerebral cell death.

The invention also relates to the use of said caspase-2-inhibitors for making drugs for preventing or treating pathologies involving caspase-2 activity.

The pharmaceutical compositions of the invention are particularly useful for preventing, reducing and treating pathologies with cell death, particularly in H-I injuries and stroke-like situations brain injuries: for example, global or focal, transient or permanent, adult or neonatal H-I (ischemia with or without hypoxia/hypoglycaemia) with origin at cerebral or heart level, with or without reperfusion, or MCAO (Middle Cerebral Artery Occlusion).

The pharmaceutical compositions of the invention are particularly useful for:

preventing and/or treating apoptosis during chronic degenerative diseases e.g. neurodegenerative disease including Alzheimer's disease, Huntingtons' disease, Parkinsons' disease, Multiple sclerosis, amyotrophic lateral sclerosis, spinobulbar atrophy, prion disease, dementia, or preventing and/or treating retinal pericyte apoptosis, retinal neurons apoptosis glaucoma, retinal damages resulting from local ischemia, diabetic retinopaty, or preventing and/or treating epilepsy, or preventing and/or treating apoptosis during spinal cord injury, or to prevent and/or treat apoptosis resulting from traumatic brain injury, retinal ischemia or preventing and/or treating apoptosis during pathological situations of focal cerebral ischemia or providing cerebroprotective effect, or preventing and/or treating cytotoxic T cell and natural killer cell-mediated apoptosis associated with autoimmune disease and transplant rejection, or preventing and/or treating cell death of cardiac cells including heart failure, cardiomyopathy, viral infection or bacterial infection of heart, myocardial ischemia, myocardial infarct, and myocardial ischemia, coronary artery by-pass graft, or preventing and/or treating mitochondrial drug toxicity e.g. as a result of chemotherapy or HIV therapy, preventing and/or treating cell death during viral infection or bacterial infection, or preventing and/or treating inflammation or inflammatory diseases, inflammatory bowel disease, sepsis and septic shock, or preventing cell death from follicule to ovocyte stages, from ovocyte to mature egg stages and sperm (for example, methods of freezing and transplanting ovarian tissue, artificial fecondation), or preserving fertility in women and men after chemotherapy, or preserving fertility in females and males animals, or to prevent and/or treat, macular degenerescence and glaucoma, or to prevent and/or treat acute hepatitis, chronic active hepatitis, hepatitis-B, and hepatitis-C, or preventing and/or treating hair loss, and said hair loss due-to male-pattern baldness, radiation, chemotherapy or emotional stress, or treating or ameliorating skin damage (due to exposure to high level of radiation, heat, burns, chemicals, sun, and autoimmune diseases), or preventing cell death of bone marrow cells in myelodysplastic symdromes (MDS), or preventing and/or treating pancreatisis, or preventing and/or treating respiratory symdrome, or preventing and/or treating osteoarthitis, rheumatoid arthritis, psoriasis, glomerulonephritis, atheroscerosis, and graft versus host disease, or preventing and/or treating disease states associated with an increase of apoptosis, or preventing cell death in vegetals (for example: plants, flowers, thallophytes (mushrooms, seaweed) . . . )

The term "treatment or treat" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treat" can also mean prolonging survival as compared to expected survival if not receiving treatment.

The invention also relates to method of treatment of pathologies with cell death, particularly ischemia and stroke injuries, comprising the administration of a therapeutically effective dose of a pharmaceutical composition such as above defined.

Precised characteristics and advantages of the invention are given in the following data with reference to the figures, which represent:

III/ PEPTIDES AND PSEUDOPEPTIDES INHIBITORS OF CASPASE-2

1. QCO-VDVAD-DFP (SEQ ID NO:1)

Qco-VDVAD-dfp (SEQ ID NO:1) is a pseudopeptide (MW: 827) that inhibits selectively human recombinant caspase-2 in vitro (IC50=80 nM) but not other cysteines-proteases. It combines pentapeptide VDVAD (SEQ ID NO:9) ((L-Valinyl-L-Aspartyl-L-Valinyl-L-Alaninyl-L-Aspartyl (SEQ ID NO:9) substituted on aspastate residues by O-methyl groups (OMe)) moieties, quinolinylcarbonyl and 2,6-difluorophenyl ester backbones. Its formula is Ia/Ib according to the position of the substituted VD(OMe)VAD(OMe)-Oph on the quinoline nucleus: for example the 2-Quinolinylcarbonyl-L-Valinyl-L-Aspartyl (methyl ester)-L-Valinyl L-Alanyl-L-Aspartyl (methyl ester) 2,6-difluorophenyl ester (SEQ ID NO:1) (II, n=0).

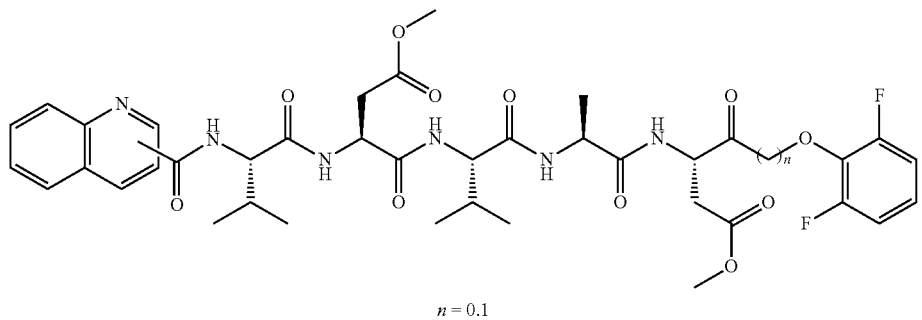

Ia $n = 0.1$

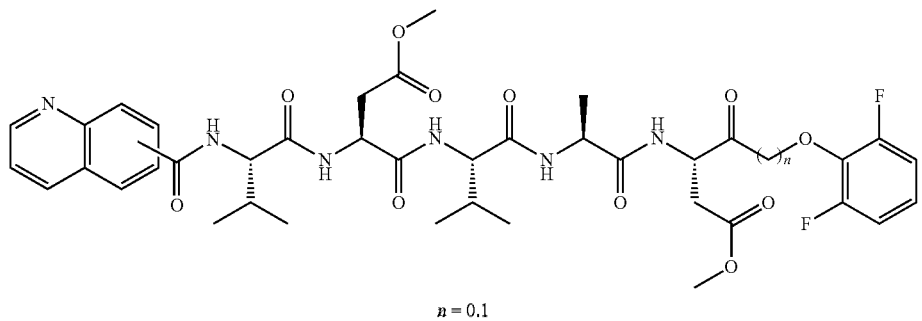

Ib $n = 0.1$

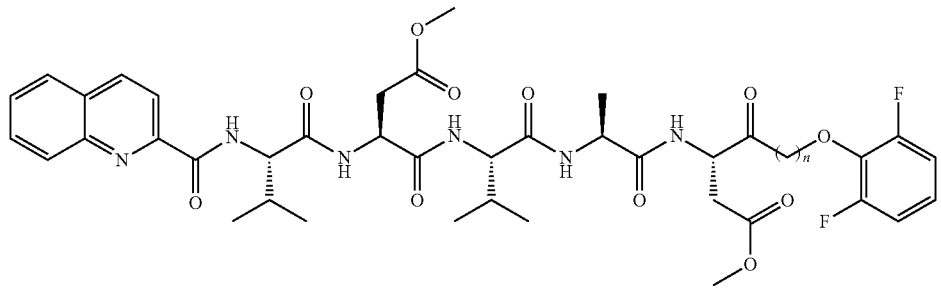

II $n = 0.1$

2-Quinolinylcarbonyl-L-Valinyl-L-Aspartyl (methyl ester)-L-Valinyl-L-Alanyl-L-Aspartyl (methyl ester) 2,6-difluorophenyl ester=(SEQ ID NO:1)

2. MODIFICATION OF AMINO ACID SIDE CHAINS AND FUNCTIONAL GROUPS

Other selective new caspase-2 inhibitors of the invention are based on structure III below:

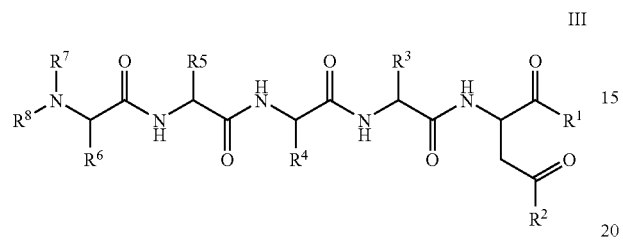

wherein
(i) the absolute configuration of each amino acid is either L or D;
(ii) $R^1$ and $R^2$ are a hydrogen atom, deuterium atom, $C_{1-20}$ aliphatic, substituted or unsubstituted aryl, cycloalkyl, naphthyl, substituted naphthyl, 2-benzoxazolyl, substituted 2-oxazolyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, $CH_2N_2$, $CH_2Y$, OH, OR, $NH_2$, NHR, $NR_2$, SR, COR, $CO_2R$, $CONR_2$, $CH_2OCOR$, $CH_2O$—CO aryl, $CH_2O$—C(O) substituted aryl (ex: 2,6-dimethylbenzoyloxymethyl), $CH_2O$—C(O) substituted aryl, $CH_2O$—C(O) heteroaryl, $CH_2O$—C(O) substituted heteroaryl or $CH_2OPOR_2$;
(iii) $R^3$, $R^4$, $R^5$ and $R^6$ are the side-chains of one of the twenty amino acids (excluding cysteine). For example, the pentapeptides can also be analogues of Leu-Asp-Glu-Ser-Asp (SEQ ID NO:2). $R^3$, $R^4$, $R^5$ and $R^6$ are also $C_{1-20}$ aliphatic, cycloalkyl, naphthyl, substituted naphthyl, 2-benzoxazolyl, substituted 2-oxazolyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, $CH_2N_2$, $(CH_2)_n$Z, $CH_2OCOR$, $CH_2OCO$ (aryl), $CH_2OCO$ (substituted aryl), $CH_2OCO$ (heteroaryl), $CH_2OCO$ (substituted heteroaryl) or $CH_2OPOR_2$;
(iv) $R^7$ is a hydrogen atom and $R^8$ is R, U, $CO(CH_2)_n$NH (U), $CO(CH_2)_nS(U)$
(v) U is (un)substituted (2-, 3-, 4-, 5-, 6-, 7- or 8-) quinolinyl, $C_{1-20}$ straight chain or branched alkyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, or a marker group such as fluorophore markers or markers useful in electronic microscopy; particularly, biotin, dinitrophenyl (DNP), iodoacetamides, DTNB, COR (ex. 2-quinolinylcarbonyl), COOR, $CO(CH_2)_n$NH(Z), Acridine derivatives (Red, yellow, orange . . . ), Fluorescein derivatives (fluorescein, FITC, FAM (carboxyfluorescein), 5-(and -6)-carboxynaphthofluorescein, carboxyfluorescein, BCECF, naptofluorescein . . . ), Oregon Green® (2',7'-difluorofluorescein) dyes (Oregon Green® 488, Oregon Green® 514 . . . ), BODIPY® (4,4-difluoro-5,7-dimethyl-4-bora-3a,4a-diaza-s-indacene-3-propionic acid) dyes (BODIPY FL, BODIPY TMR, BODIPY TR, BODIPY 630/650, BODIPY 630/665 . . . ), Bimane, Coumarin derivatives (aminomethylcoumarin (AMC), AMCA, aminocoumarin, diethylaminocoumarin hydroxymethylcoumarin; hydroxycoumarin, methoxycoumarin, AFC, . . . ), Cyanin derivatives (phycocyanin, allophycocyanin (APC), CY3.18, CY5.18, Cy2, Cy3, Cy3.5, Cy5, Cy5.5, Cy7 . . . ), Erythrin/Phycoerythrin derivatives (R-Phycoerythrin (PE), B-Phycoerythrin . . . ), APC/PE-Cy conjugates (PE-Cy5 conjugates, PE-Cy7 conjugates, APC-Cy7 conjugates . . . ), Calcein derivatives (calcein, SNAFL calcein . . . ), DANS, DANSA, Cascade Blue, Lucifer yellow, NBD, Red 613, FluorX, Rhodamine derivatives (Rhodamine 123, Rhodamine 110, Rhodamine B, Rhodamine 6A, Rhodamine 6G, TRITC, X-Rhodamine, sulphorhodamin, Rhodamine Red-X, Lissamine™ rhodamine B, DHR, Rhodamine Green . . . ), PerCP, Texas Red, TruRed, Alexa Fluo® (Alexa Fluor 350, Alexa Fluor 430, Alexa Fluor 488, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750 . . . ), Q-DOTs™ derivatives (655,605, 585,525, . . . ), SNARF, Zenon™ derivatives (Zenon™ Alexa Fluor® 350, Zenon™ Alexa Fluor® 488, Zenon™ Alexa Fluor® 555, Zenon™ Alexa Fluor® 594, Zenon™ Alexa Fluor® 647, Zenon™ Allophycocyanin, Zenon™ Biotin-XX, Zenon™ R-Phycoerythrin, . . . ); NBD, Texas Red®, QSY® dyes (QSY® 7, QSY® 9, QSY® 35, QSY® 21), Hoechst (33342, 33258), DAPI, Chromomycin A3, Mithramycin, SYTOX (Blue, Green, Orange), Ethdium, Ethidium Bromide, 7-AAD, TOTO dyes, YOYO dyes, TO-PRO dyes, BOBO dyes, JO-PRO dyes, LO-PRO dyes, PO-PRO dyes, YO-PRO dyes, Thiazole Orange, Propidium Iodide (PI), LDS 751, Indo® dyes (Indo-1 . . . ), Fluo® dyes (Fluo-3 . . . ), DCFH, pNA, SYBR green II, SyPro (Orange, Ruby), EDANS, IR800, DiI, DiO, DiD, SNARF® derivatives, Fura dyes, QUIN dyes, NANOGOLD particles, NANOGOLD maleimide, AlexaFluor FluoroNANOGOLD, AlexaFluor FluoroNANOGOLD streptavidin, malachite green, Dabcyl, Dabsyl, Cascade yellow, dansyl, Dapoxyl, PyMPO, Pyrene; benzoxadiazole derivatives, strepavidin-/neutravidin-)biotin-labeled fluorescent microspheres, CMNB-caged fluorescein conjugate of streptavidin, calcofluor white, nile red, Y66F, Y66H, EBFP, GFP wild type, QFP mutants H9/P4/P9/P11/W, GFPuv, ECFP, Y66W, S65A, S65C, S65L, S65T, EGFP, EYFP, ECFP, DsRed1, DsRed2, NANOGOLD® particles, streptavidin-Nanogold®, Monomaleido Nanogold®, Mono-Sulfo-NHS-Nanogold®, Monoamino Nanogold®, positively/negatively charged Nanogold® (NN, NHSN, NHSNA, NHSNS), Non-Functionalized Nanogold®, Monomaleido Nanogold®, Mono-Sulfo-NHS-Nanogold®, Monoamino Nanogold®, Non-functional Nanogold®, Nanogold®-conjugates, Nanogold®-streptavidin, lipide-Nanogold (Palmitoyl Nanogold®, DPPE Nanogold®, Palmitoyl Undecagold, DPPE Undecagold), Ni-NTA-Nanogold®, Alexa Fluor® 488 FluoroNanogold, Alexa Fluor® 594 FluoroNanogold, Fluorescein FluoroNanogold, HRP substrate-Nanogold.
(vi) $R^7$ and $R^8$ are also taken together with the intervening nitrogen to form a heterocyclic ring such as substituted or unsubstituted tetrahydroquinoline, tetrahydroisoquinoline, dihydroacridine, benzazepine, pyrrolidine, morpholine, thiomortholine, piperazine, piperidine, dihydropyridine, benzimidazole, imidazole, imidazoline, pyrrole, pyrrolidine, pyrroline, pyrazole, pyrazoline, pyrazolidine, triazole, piperidine, morpholine, thiomorpholine, piperazine, carbazole, phenothiazine, phenoxazine, dihydrophenazine, dihydrocinnoline, dihydroquinoxaline, dihydronaphthyridine, tetrahydronaphthyridine, dihydroacridine, indole, isoindole, dihydroindole, indoline, indazole, purine, 9,10-dihydrophenanthridine, 5H-dibenzo[b,f]azepine, 10,11-dihydro-5H-dibenzo[b,f]azepine, β-carboline, pyrido[4,3-b]indole, 2,3,9-triazofluorene, 9-thia-2,10-diazaanthracene, thieno[3,2b]pyrrole, dihydrophenanthrine.

(vii) R is a hydrogen atom, $C_{1-20}$ aliphatic group, aryl, substituted aryl (ex: 4-nitrophenyl or coumarine derivatives), hetetoaryl (ex. 2-pyridine), substituted heteroaryl, cycloalkyl, naphthyl, substituted naphthyl, $(CH_2)_n$cycloalkyl, $(CH_2)_n$phenyl, $(CH_2)_n$substituted phenyl (ex: 2,6-dihalophenyl), $(CH_2)_n$(1- or 2-naphthyl), $(CH_2)_n$heteroaryl or (un)substituted (2-, 3-, 4-, 5-, 6-, 7- or 8-) quinolinyl, fluorenmethyl;

(viii) Y is an electronegative leaving group including halogens such as F, Cl, Br or I, aryl or alkylsulfonyloxy groups, trifluoromethanesulfonyloxy, OR, SR, COOR, $OP(O)R_2$ wherein R is an aliphatic group, an aryl group, an aralkyl group, a carbocyclic group, an alkyl carbocyclic group, or a heterocyclic group;

(ix) Z is a halogen (F, Cl, Br or I), CN, OH, OR, $NH_2$, NHR, $NR_2$, SR, COR, $CO_2R$, $CONR_2$, (x) n is 0 to 20;

As used herein, the following definitions shall apply unless otherwise indicated. The abbreviations Q and OPH stand for quinolinylcarbonyl and 2,6-difluorophenoxy respectively. The term "aliphatic" herein means straight chained or branched $C_{1-20}$ hydrocarbons which are completely saturated or which contain one or more units of unsaturation. The term "alkyl" used alone or as part of a larger moiety refers to both straight or branched chains containing one to twenty carbon atoms. The term "aryl" refers to mono cyclic or polycyclic aromatic ring groups having five to fourteen atoms, such as phenyl, naphthyl or anthryl. The term "heterocyclic group" refers to saturated or unsaturated polycyclic or monocyclic ring systems containing one or more heteroatoms and a ring size of three to nine such as furanyl, thienyl, pyrrolyl, pyrrolinyl, pyrrolidinyl, dioxolanyl, oxazolyl, thiazolyl, imidazolyl, imidazolinyl, imidazolidinyl, pyrazolyl, pyrazolinyl, pyrazolidinyl, isoxalolyl, isothiazolyl, oxadiazolyl, dioxanyl, morpholinyl, dithianyl, thiomorpholinyl, pyridazinyl, pyrimidinyl, pyrazinyl, piperazinyl, triazinyl, trithianyl, indolizinyl, indolyl, isoindolyl, indolinyl, benzofuranyl, benzothiophenyl, indazolyl, benzamidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, quinuclidinyl, carbazolyl, acridinyl, phenazinyl, phenothiazinyl, or phenoxazinyl. "Heteroaryl" refers to a heterocyclic ring that is aromatic. The term "carbocyclic group" refers to unsaturated monocyclic or polycyclic carbon ring systems of three to fourteen carbons which may be fused to aryl or heterocyclic groups. An aliphatic, alkyl, aryl, heteroaryl (ex: quinoline), heterocyclyl, or carbocyclyl, used alone or as part of a larger moiety, refers to substituted or unsubstituted groups. When substituted, these groups may contain one or more substituents. These substituents can be halogen (F, Cl, Br, I), OH, U, $CO(CH_2)_nNH(U)$, $CO(CH_2)_nS$ (U), OR, SR, $NH_2$, NHR, $NR_2$, OCOR, $OP(O)R_2$ wherein R is an aliphatic group, an aryl or substituted group, an aralkyl group, a carbocyclic group, an alkyl carbocyclic group, a heterocyclic group or a radio-isotope (ex: $I^{125}$, $H^3$, $S^{35}$, $C^{14}$, $P^{33}$, $P^{32}$, $Cr^{51}$, $Ca^{45}$, $Fe^{59}$, $Ni^{63}$, $Ba^{133}$, $Cs^{137}$, $Eu^{152}$, $Ra^{226}$, $Xe^{133}$, technétium 99, thallium 201). FITC stands for fluorescein isothiocyanate.

3. PEPTIDE ISOSTERES OR BIOISOSTERES (a) This invention also relates to carba analogues of formula IV.1 to IV.7 (Table 1) wherein
  (i) the absolute configuration of each amino acid or its isostere is either L or D;
  (ii) n, R, $R^1$, $R^2$, $R^3$, $R^4$, $R^5$, $R^6$, $R^7$, $R^8$, U, Y and Z are as described above.

TABLE 1

Carba analogues of the pentapeptide VDVAD (SEQ ID NO: 9) (compounds IV.1 to IV.7)

| No. | Structure |
|---|---|
| 1 | 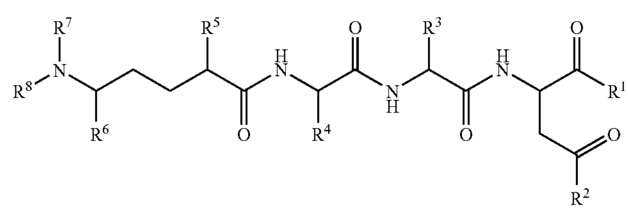 |
| 2 | 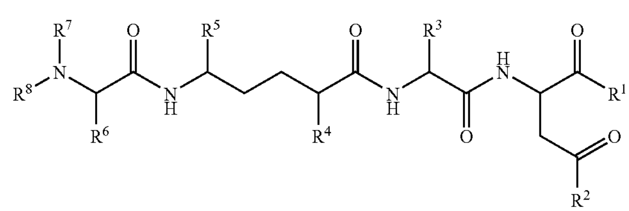 |

TABLE 1-continued

Carba analogues of the pentapeptide VDVAD (SEQ ID NO: 9) (compounds IV.1 to IV.7)

| No. | Structure |
|---|---|
| 3 | [structure] |
| 4 | [structure] |
| 5 | [structure] |
| 6 | [structure] |
| 7 | [structure] |

(b) The invention also relates to ketomethylene analogues of formula V.1 to V.7 (Table 2) in which
  (i) the absolute configuration of each amino acid or its isostere is either L or D;
  (ii) n, R, $R^1$, $R^2$, $R^3$, $R^4$, $R^5$, $R^6$, $R^7$, $R^8$, U, Y and Z are as described previously.

TABLE 2

Ketomethylene analogues of the pentapeptide VDVAD (SEQ ID NO: 9) (compounds V.1 to V.7)

| No. | Structure |
|---|---|
| 1 | [structure] |

TABLE 2-continued
Ketomethylene analogues of the pentapeptide VDVAD (SEQ ID NO: 9)
(compounds V.1 to V.7)
| No. | Structure |
|---|---|
| 2 | 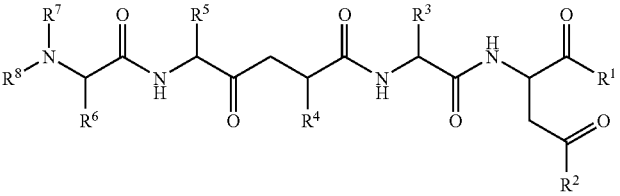 |
| 3 | 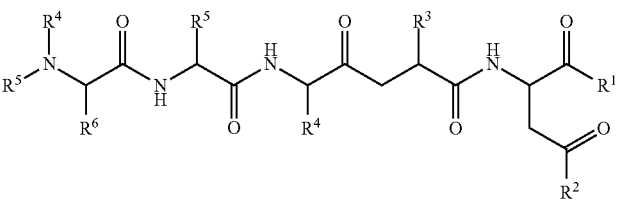 |
| 4 | 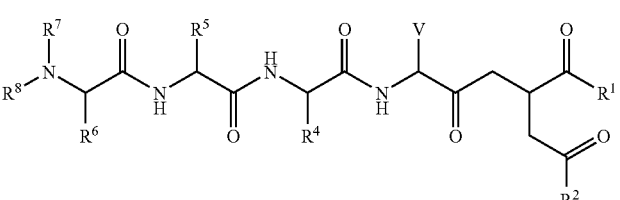 |
| 5 | 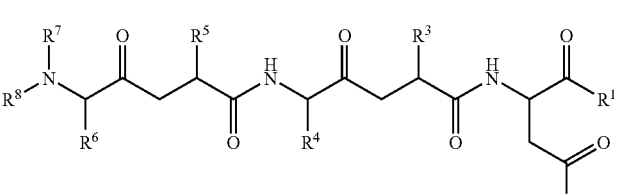 |
| 6 | 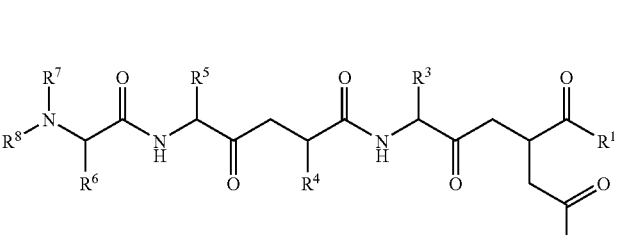 |
| 7 | 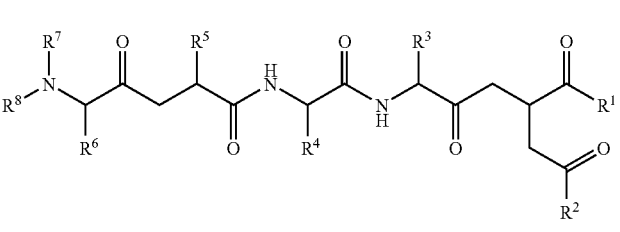 |

(c) The invention also relates to depsi-peptides analogues of the general formula VI and VII wherein
   (i) the absolute configuration of each amino acid or its isostere is either L or D;
   (ii) X is O or NH and at least one X an oxygen atom
   (iii) n, R, $R^1$, $R^2$, $R^3$, $R^4$, $R^5$, $R^6$, $R^7$, $R^8$, U, Y and Z are as described above
   (iv) $R^9$ is a hydrogen atom, (2-, 3-, 4-, 5-, 6-, 7- or 8-) quinolinyl, $C_{1-20}$ straight chain or branched alkyl, $(CH_2)_n$cycloalkyl, $(CH_2)_n$phenyl, $(CH_2)_n$substituted phenyl, $(CH_2)_n$(1- or 2-naphthyl), $(CH_2)_n$heteroaryl, OCOR or OCNHR.

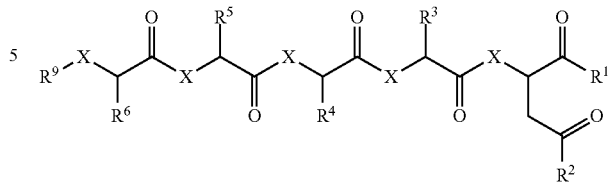

VII

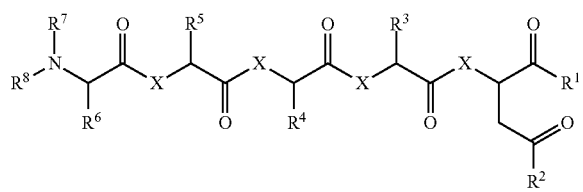

VI (d) The invention also relates to hydroxyethylene analogues of formula VIII.1 to VIII.7 (Table 3), wherein
   (i) the absolute configuration of each amino acid or its isostere is either L or D;
   (ii) n, R, $R^1$, $R^2$, $R^3$, $R^4$, $R^5$, $R^6$, $R^7$, $R^8$, U, Y and Z are as described above.

TABLE 3

Hydroxyethylene analogues of VDVAD (SEQ ID NO: 9) (compounds VIII.1 to VIII.7)

| No. | Structure |
|---|---|
| 1 | 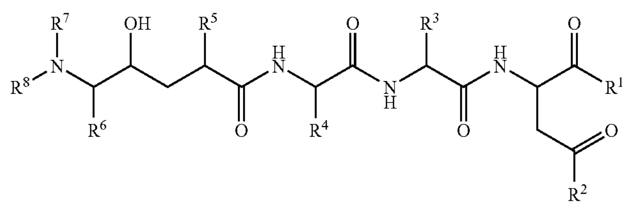 |
| 2 | 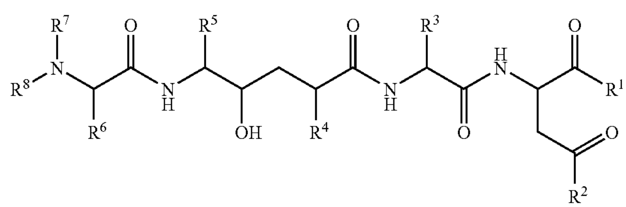 |
| 3 | 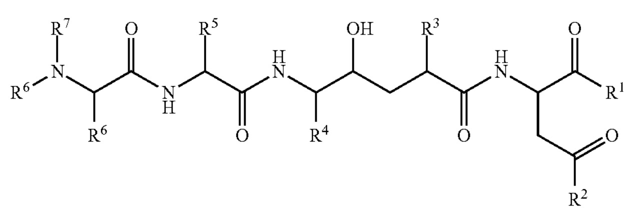 |
| 4 | 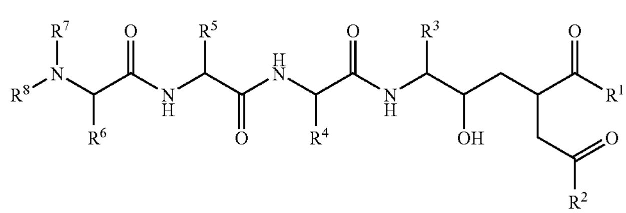 |

TABLE 3-continued

Hydroxyethylene analogues of VDVAD (SEQ ID NO: 9) (compounds VIII.1 to VIII.7)

| No. | Structure |
|---|---|
| 5 | 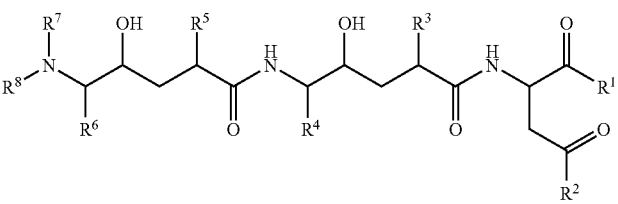 |
| 6 | 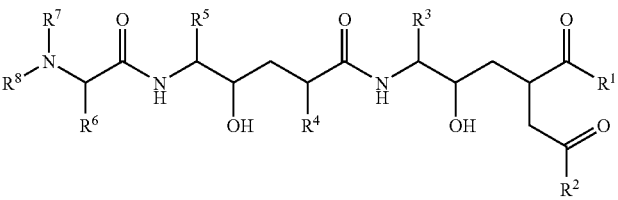 |
| 7 | 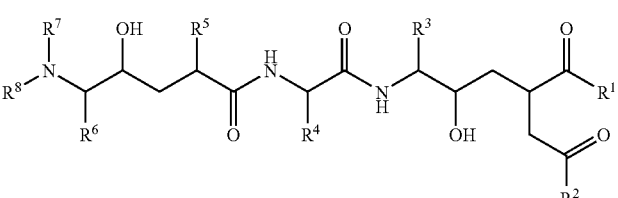 |

(e) The invention also relates to reduced pentapeptide analogues of formula IX.1 to IX.6 (Table 4), wherein
(i) the absolute configuration of each amino acid or its isostere is either L or D;
(ii) n, R, $R^1$, $R^2$, $R^3$, $R^4$, $R^5$, $R^6$, $R^7$, $R^8$, U, Y and Z are as described above.

TABLE 4

Reduced analogues of VDVAD (SEQ ID NO: 9) (compounds IX.1 to IX.6)

| No. | Structure |
|---|---|
| 1 | 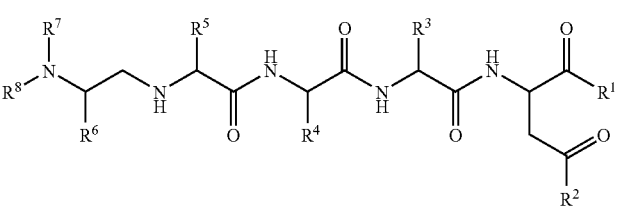 |
| 2 | 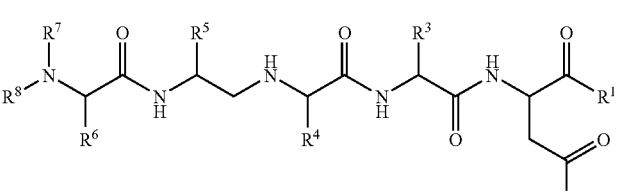 |

TABLE 4-continued

Reduced analogues of VDVAD (SEQ ID NO: 9) (compounds IX.1 to IX.6)

| No. | Structure |
|---|---|
| 3 | [chemical structure] |
| 4 | [chemical structure] |
| 5 | [chemical structure] |
| 6 | [chemical structure] |

(f) The invention also relates to unsaturated analogues of the formula X.1 to X.7 (Table 5) wherein
  (i) the absolute configuration of each amino acid or its isostere is either L or D;
  (ii) n, R, $R^1$, $R^2$, $R^3$, $R^4$, $R^5$, $R^6$, $R^7$, $R^8$, U, Y and Z are as described above.

TABLE 5

Unsaturated analogues of VDVAD (SEQ ID NO: 9) (compounds X.1 to X.7)

| No. | Structure |
|---|---|
| 1 | [chemical structure] |

TABLE 5-continued

Unsaturated analogues of VDVAD (SEQ ID NO: 9) (compounds X.1 to X.7)

| No. | Structure |
|---|---|
| 2 | 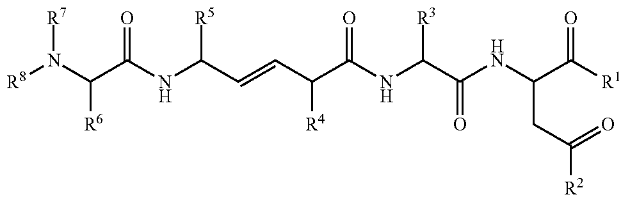 |
| 3 | 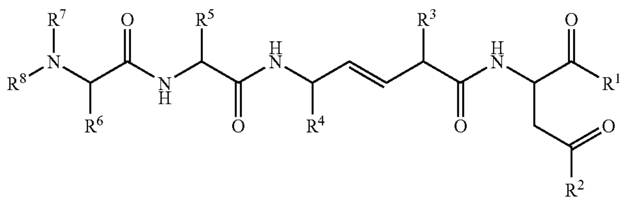 |
| 4 | 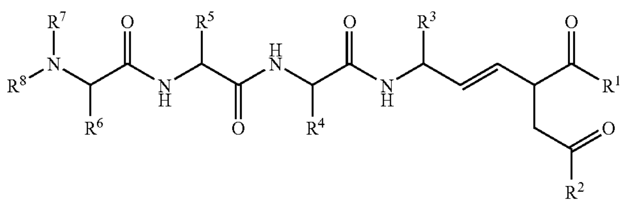 |
| 5 | 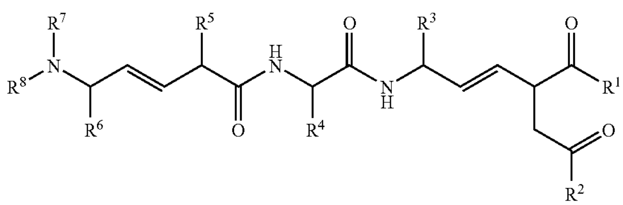 |
| 6 | 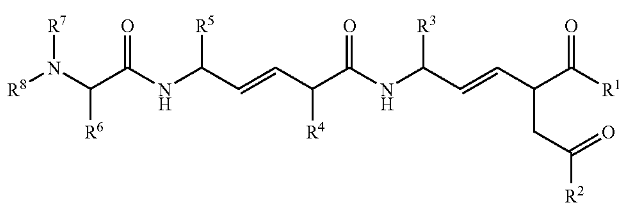 |
| 7 | 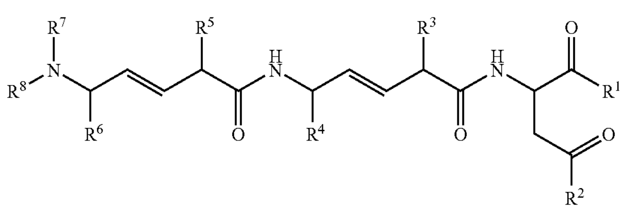 |

(g) The invention also relates to β-peptides, γ-peptides, urea, and carbamates analogues of the formula XI.1 to XI.9 (Table 6) in which
  (i) the absolute configuration of each amino acid or its isostere is either L or D;
  (ii) X is $CH_2$, NH, O
  (iii) n, R, $R^1$, $R^2$, $R^3$, $R^4$, $R^5$, $R^6$, $R^7$, $R^8$, U, Y and Z are as described above.

TABLE 6
Unsaturated analogues XI.1 to XI.9
| No. | Structure |
|---|---|
| 1 | 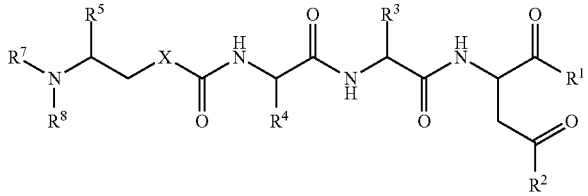 |
| 2 | 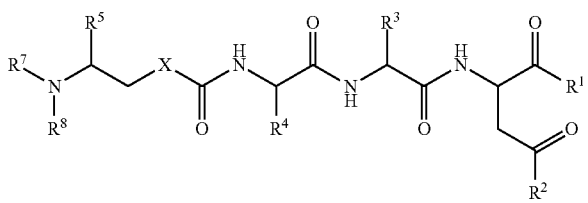 |
| 3 | 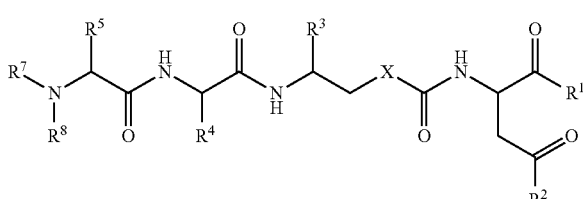 |
| 4 | 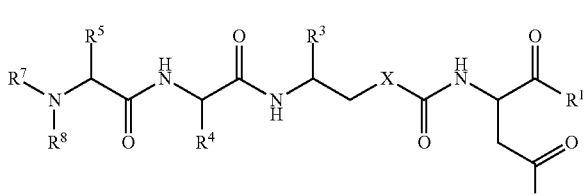 |
| 5 | 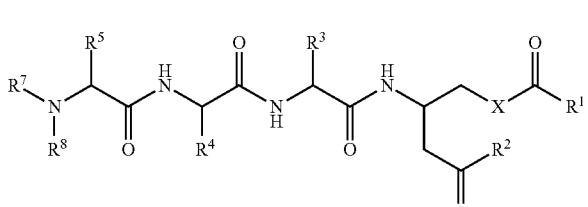 |
| 6 | 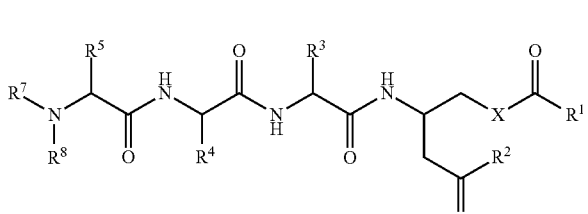 |
| 7 | 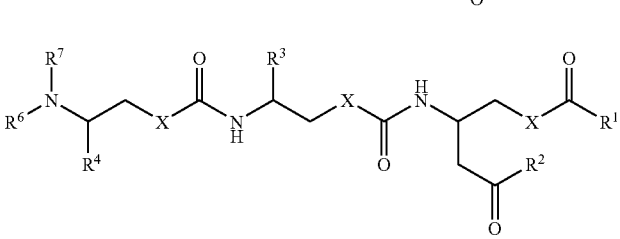 |

TABLE 6-continued

Unsaturated analogues XI.1 to XI.9

| No. | Structure |
|---|---|
| 8 | 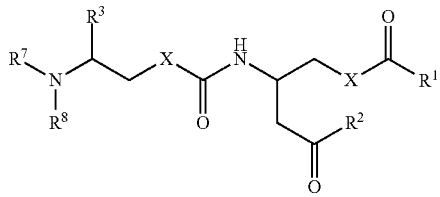 |
| 9 | 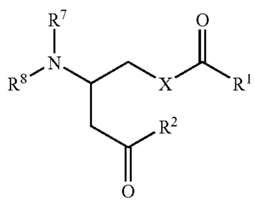 |
| 10 | 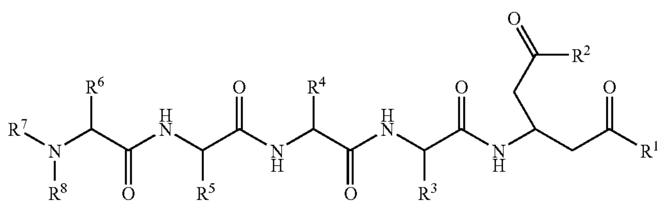 |
| 11 | 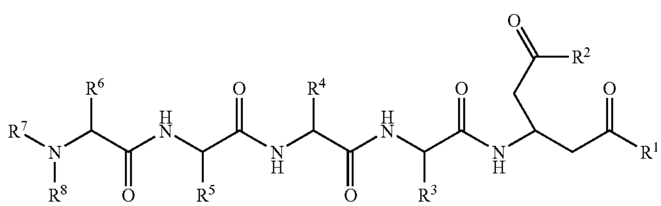 |
| 12 | 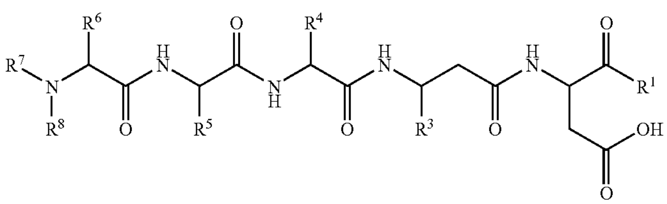 |
| 13 | 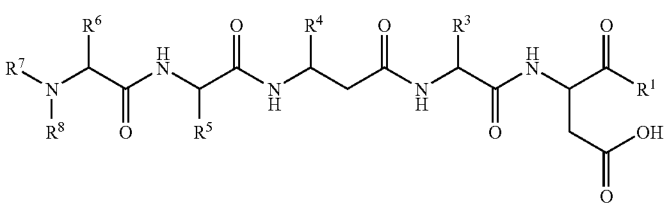 |
| 14 | 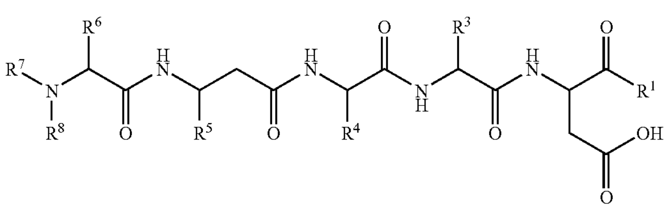 |

TABLE 6-continued

Unsaturated analogues XI.1 to XI.9

| No. | Structure |
|---|---|
| 15 | 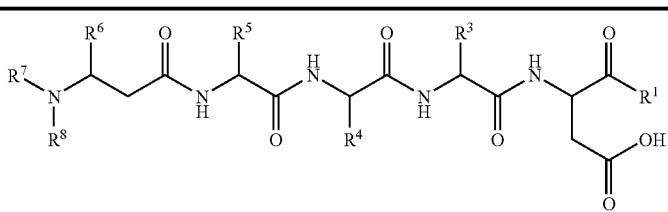 |

4. CONSTRAINED ANALOGUES OF VDVAD (SEQ ID NO:9) PENTAPEPTIDE

The invention also relates to constrained analogues of VDVAD (SEQ ID NO:9) pentapeptide shown in tables 7 to 14. In theses compounds the aryl, heteroaryl or heterocyclyl refers to substituted or unsubstituted groups. When substituted, these groups may contain one or more substituents. These substituents can be halogen (F, Cl, Br, I), OH, U, $CO(CH_2)_nNH(U)$, $CO(CH_2)_nS(U)$, OR, SR, $NH_2$, NHR, $NR_2$, OCOR, $OP(O)R_2$ wherein R and U are as described above.

(a) The invention also relates to 3-aminopyridin-2(1H)-ones, 3-aminopyrazin-2(1H)-ones, 5-aminopyrimidin-4(3H)-ones, pyridazin-3(2H)-ones, 4-aminopyridazin-3(2H)-ones, 5-amino-1,2,4-triazin-6(1H)-ones, 5-amino-1,2,3-triazin-4(3H)-ones and 6-amino-1,2,3,4-tetrazin-5(4H)-ones XII.1 to XII.15 (Table 7) as constrained analogues of the pentapeptide VDVAD in which
  (i) the absolute configuration of each amino acid or its isostere is either L or D;
  (ii) W, X and Y are CH, C or N;
  (iii) n, R, $R^1$, $R^2$, $R^3$, $R^4$, $R^5$, $R^6$, $R^7$, $R^8$, U, Y and Z are as described previously.

TABLE 7

Constrained analogues of VDVAD (SEQ ID NO: 9) (compounds XII.1 to XII.15)

| No. | Structure |
|---|---|
| 1 | 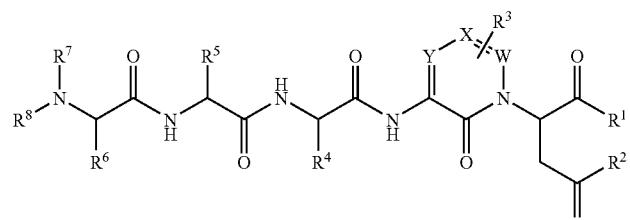 |
| 2 | 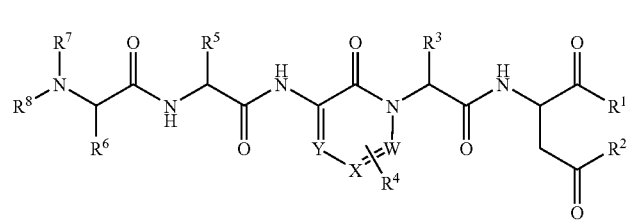 |
| 3 | 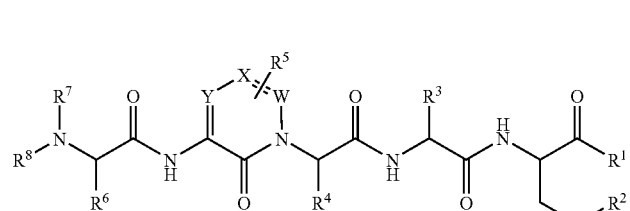 |

TABLE 7-continued

Constrained analogues of VDVAD (SEQ ID NO: 9) (compounds XII.1 to XII.15)

| No. | Structure |
|-----|-----------|
| 4 | 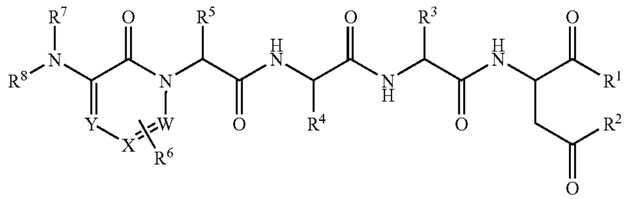 |
| 5 | 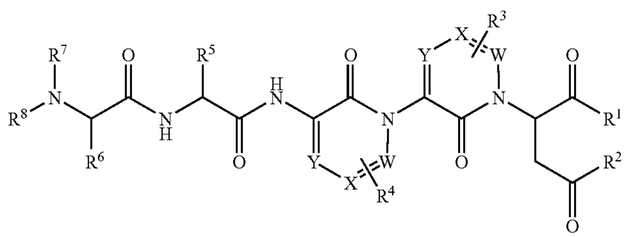 |
| 6 | 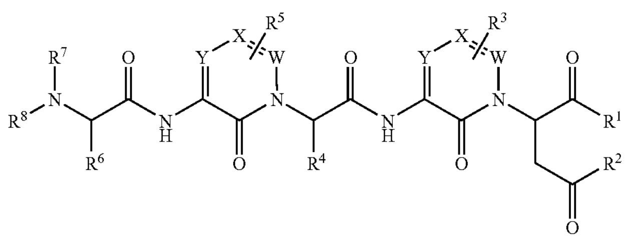 |
| 7 | 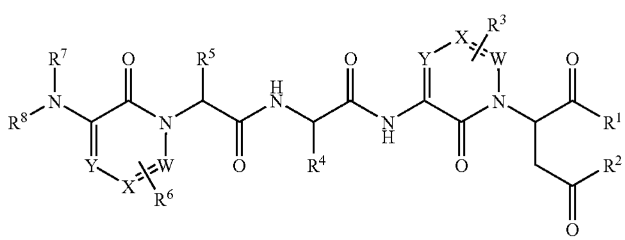 |
| 8 | 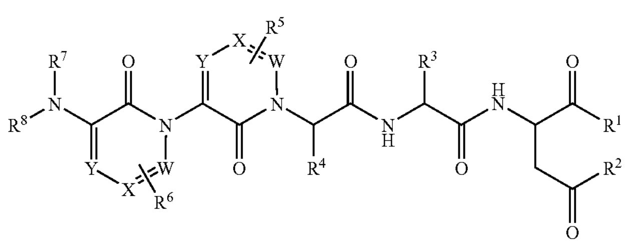 |
| 9 | 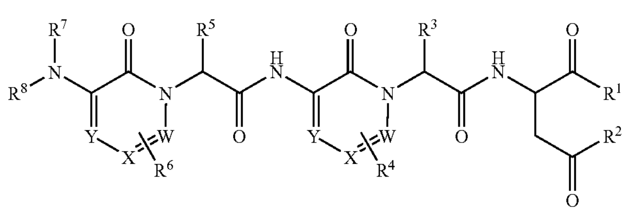 |

TABLE 7-continued

Constrained analogues of VDVAD (SEQ ID NO: 9) (compounds XII.1 to XII.15)

| No. | Structure |
|-----|-----------|
| 10 | 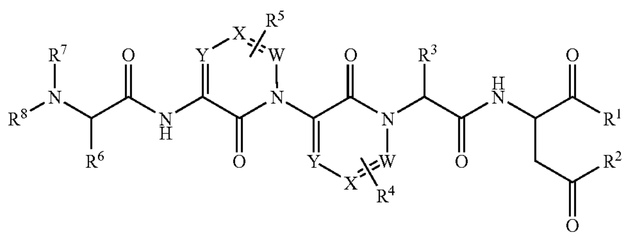 |
| 11 | 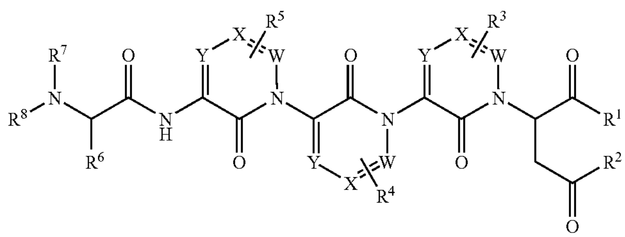 |
| 12 | 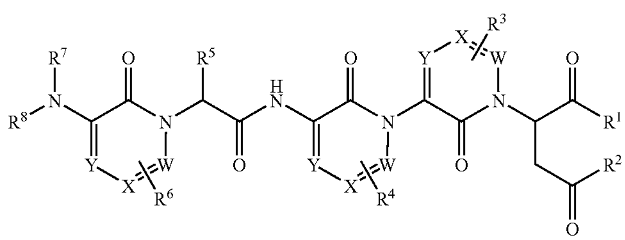 |
| 13 | 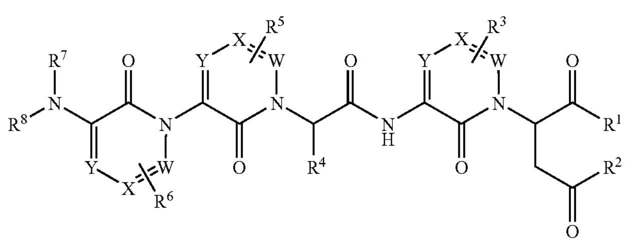 |
| 14 | 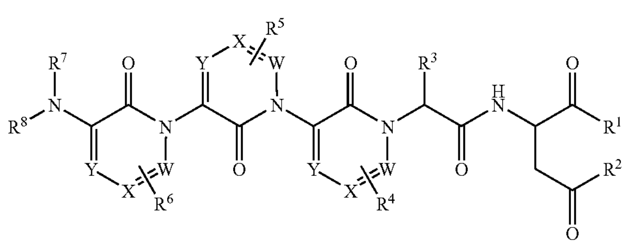 |
| 15 | 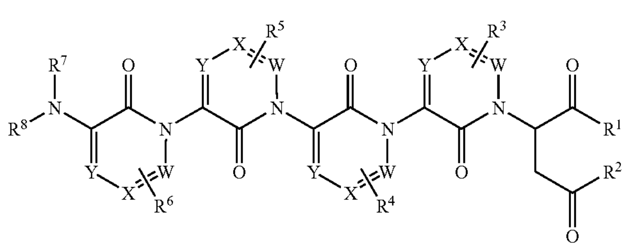 |

(b) The invention also relates to 3-aminopiperidin-2-ones, 3-aminopiperazin-2-ones, 5-amino-tetrahydropyrimidin-4(1H)-ones, 4-aminopiperazin-3-ones, 6-amino-1,2,4-triazinan-5-ones, 5-amino-1,2,4-triazinan-6-ones, 5-amino-1,2,3-triazinan-4-ones and 6-amino-1,2,3,4-tetrazinan-5-ones XIII.1 to XIII.15 (Table 8) in which (i) the absolute configuration of each amino acid or its isostere is either L or D;

(ii) W, X and Y are $CH_2$, NH, O or S;

(iii) n, R, $R^1$, $R^2$, $R^3$, $R^4$, $R^5$, $R^6$, $R^7$, $R^8$, U, Y and Z are as described above.

TABLE 8

Constrained analogues of VDVAD (SEQ ID NO: 9) (compounds XIII.1 to XIII.15)

| No. | Structure |
|---|---|
| 1 | 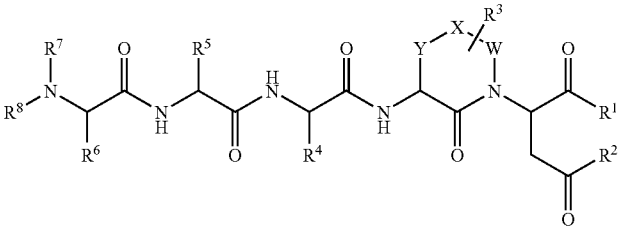 |
| 2 | 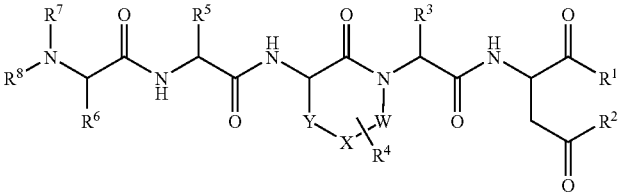 |
| 3 | 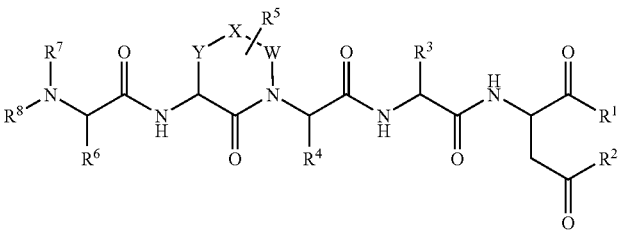 |
| 4 | 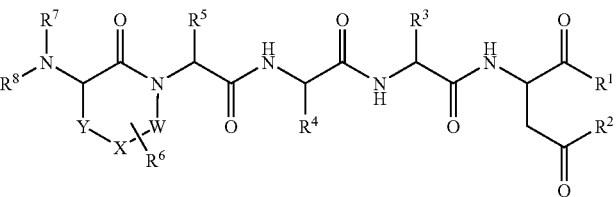 |
| 5 | 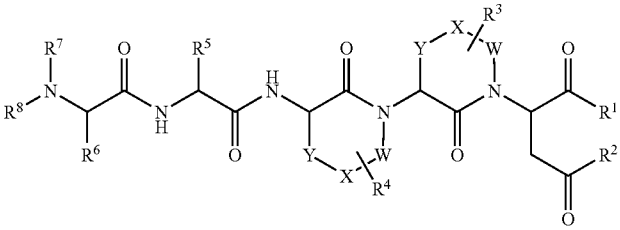 |
| 6 | 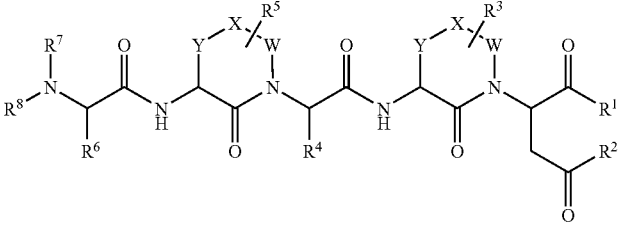 |

TABLE 8-continued

Constrained analogues of VDVAD (SEQ ID NO: 9) (compounds XIII.1 to XIII.15)

| No. | Structure |
|---|---|
| 7 | 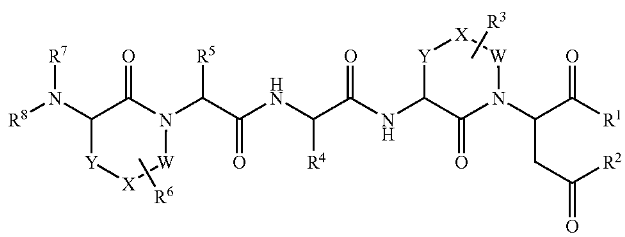 |
| 8 | 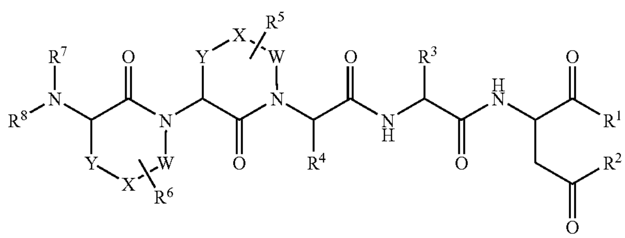 |
| 9 | 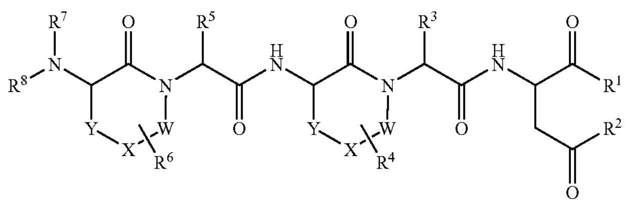 |
| 10 | 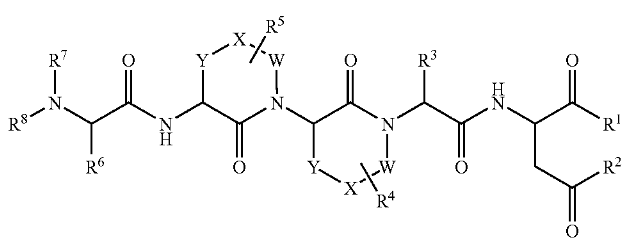 |
| 11 | 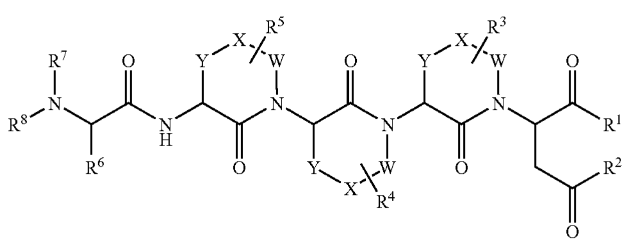 |
| 12 | 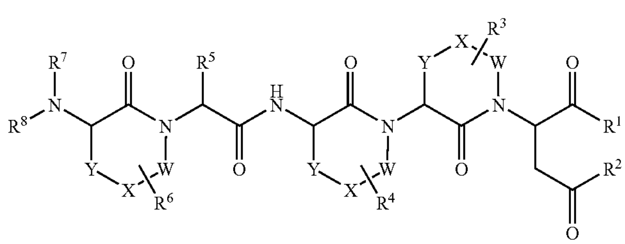 |

TABLE 8-continued

Constrained analogues of VDVAD (SEQ ID NO: 9) (compounds XIII.1 to XIII.15)

| No. | Structure |
|---|---|
| 13 | (structure) |
| 14 | (structure) |
| 15 | (structure) |

(c) Compounds of this invention also include 3-amino-3,4-dihydroquinolin-2(1H)-ones XIV.1 to XIV.15 (Table 9) in which
  (i) the absolute configuration of each amino acid or its isostere is either L or D;
  (ii) n, R, $R^1$, $R^2$, $R^3$, $R^4$, $R^5$, $R^6$, $R^7$, $R^8$, U, Y and Z are as described previously.

TABLE 9

Constrained analogues of VDVAD (SEQ ID NO: 9) (compounds XIV.1 to XIV.15)

| No. | Structure |
|---|---|
| 1 | (structure) |

TABLE 9-continued

Constrained analogues of VDVAD (SEQ ID NO: 9) (compounds XIV.1 to XIV.15)

| No. | Structure |
|-----|-----------|
| 2 | 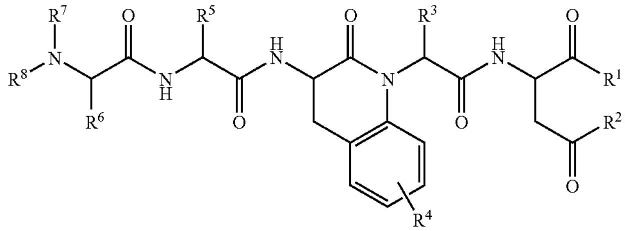 |
| 3 | 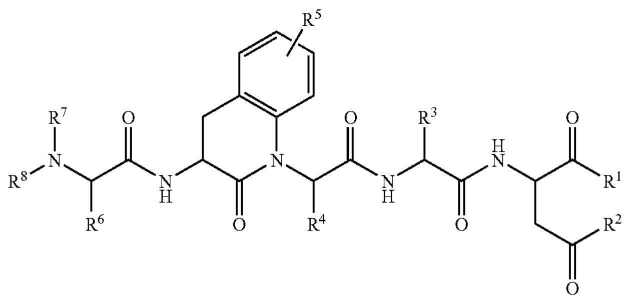 |
| 4 | 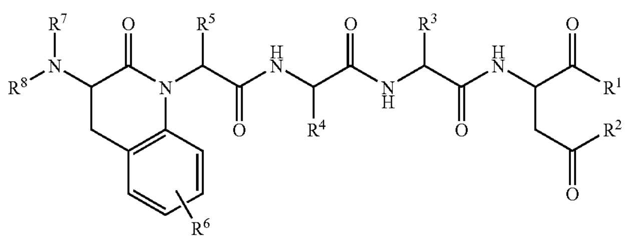 |
| 5 | 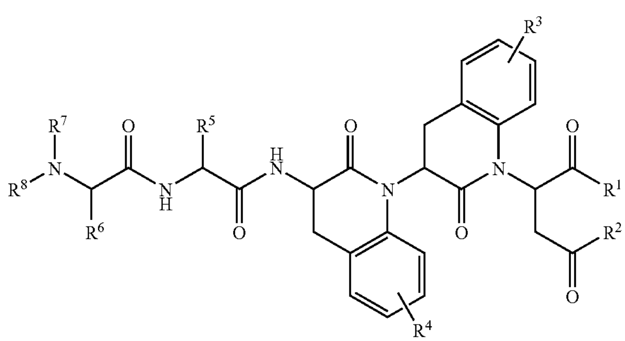 |
| 6 | 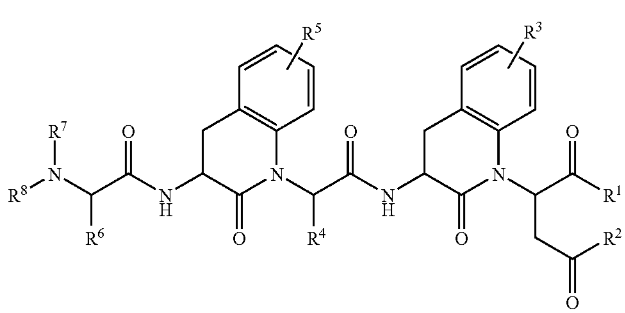 |

TABLE 9-continued

Constrained analogues of VDVAD (SEQ ID NO: 9) (compounds XIV.1 to XIV.15)

| No. | Structure |
|---|---|
| 7 | 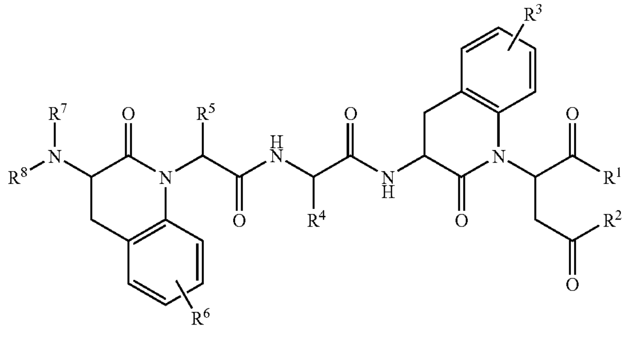 |
| 8 | 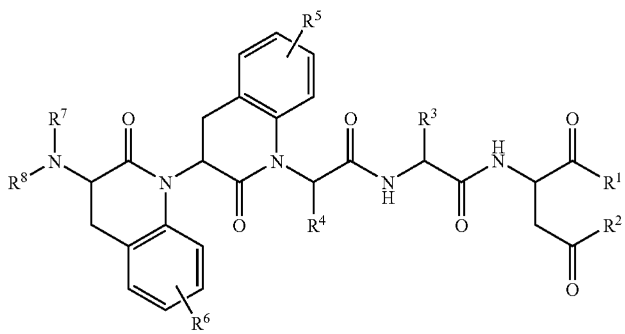 |
| 9 | 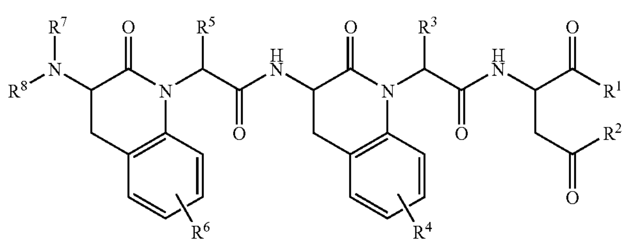 |
| 10 | 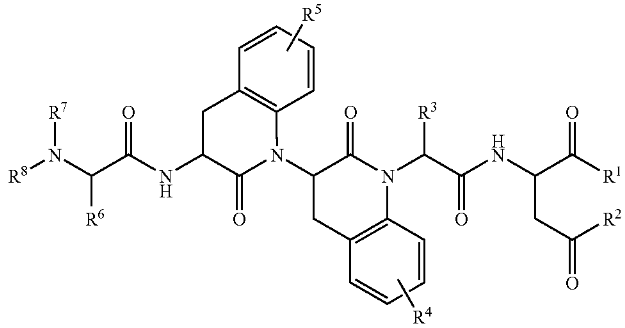 |

TABLE 9-continued
Constrained analogues of VDVAD (SEQ ID NO: 9) (compounds XIV.1 to XIV.15)
| No. | Structure |
| --- | --- |
| 11 | 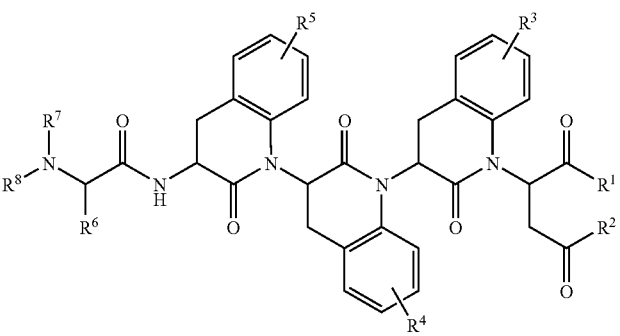 |
| 12 | 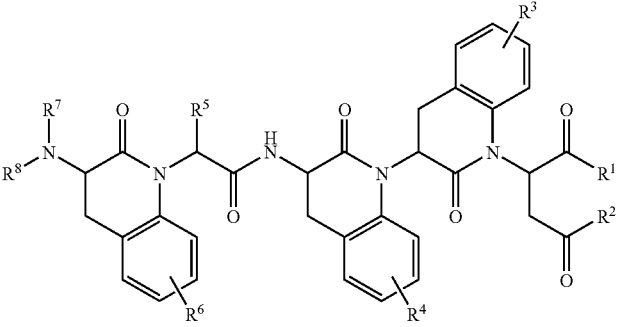 |
| 13 | 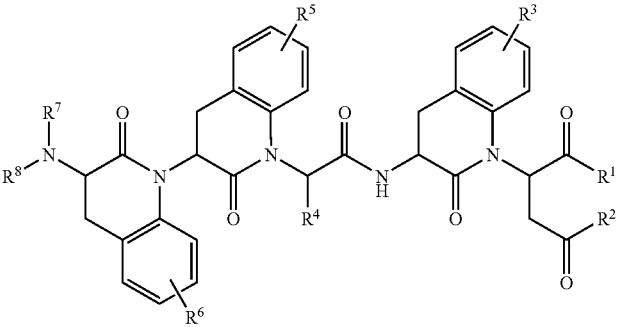 |
| 14 | 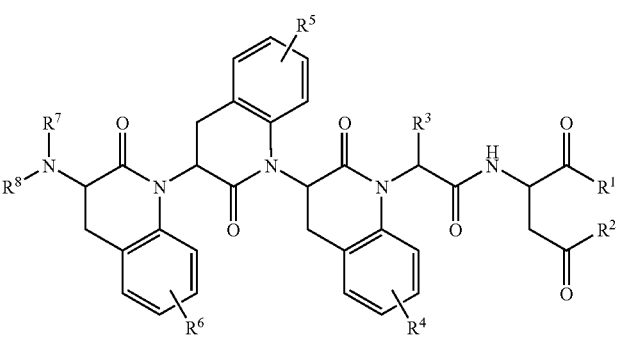 |

TABLE 9-continued

Constrained analogues of VDVAD (SEQ ID NO: 9) (compounds XIV.1 to XIV.15)

| No. | Structure |
|---|---|
| 15 | 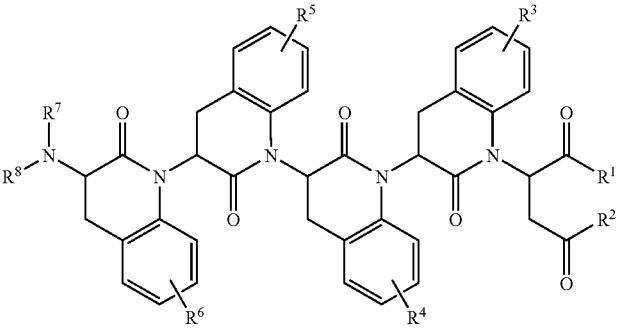 |

(d) The invention also relates to 4-amino-1,2-dihydroiso-quinolin-3(4H)-ones XV.1 to XV.15 (Table 10) in which
  (i) the absolute configuration of each amino acid or its isostere is either L or D;
  (ii) n, R, $R^1$, $R^2$, $R^3$, $R^4$, $R^5$, $R^6$, $R^7$, $R^8$, U, Y and Z are as described previously.

TABLE 10

Constrained analogues of VDVAD (SEQ ID NO: 9) (compounds XV.1 to XV.15)

| No. | Structure |
|---|---|
| 1 | 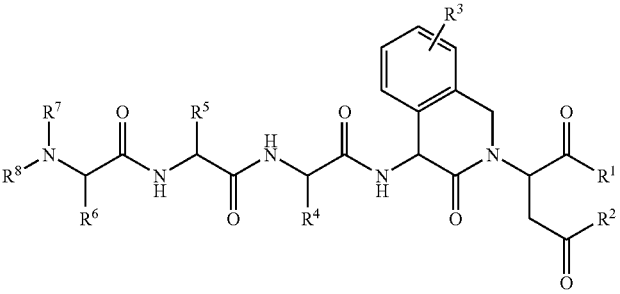 |
| 2 | 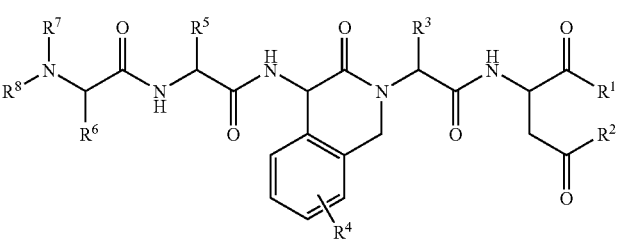 |
| 3 | 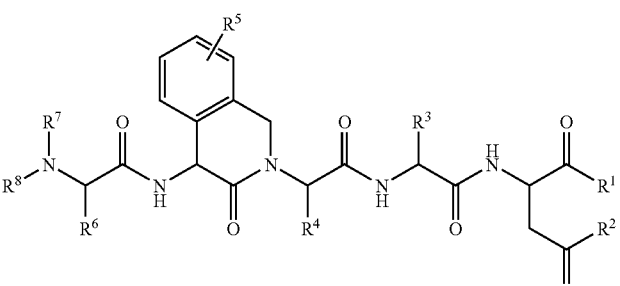 |

TABLE 10-continued
Constrained analogues of VDVAD (SEQ ID NO: 9) (compounds XV.1 to XV.15)
| No. | Structure |
|---|---|
| 4 | 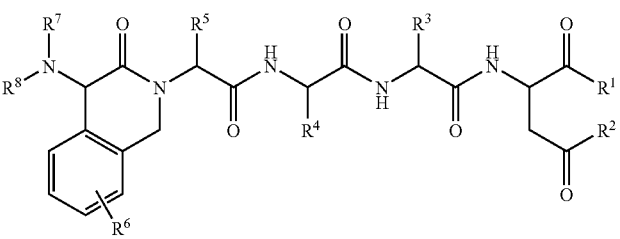 |
| 5 | 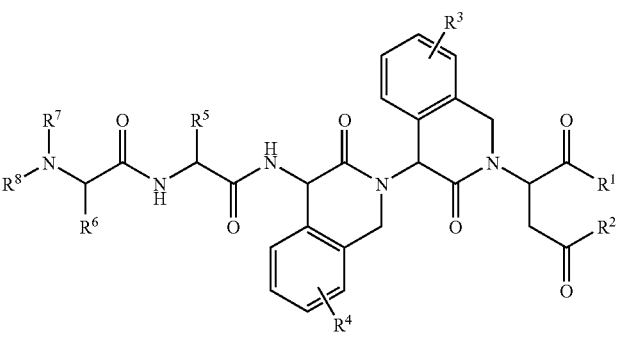 |
| 6 | 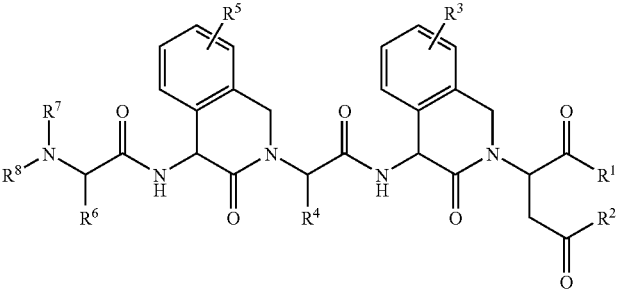 |
| 7 | 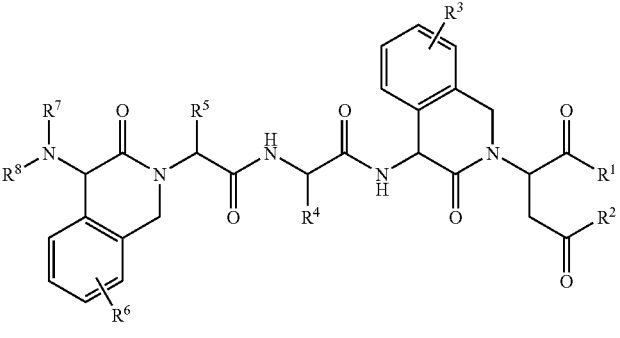 |
| 8 | 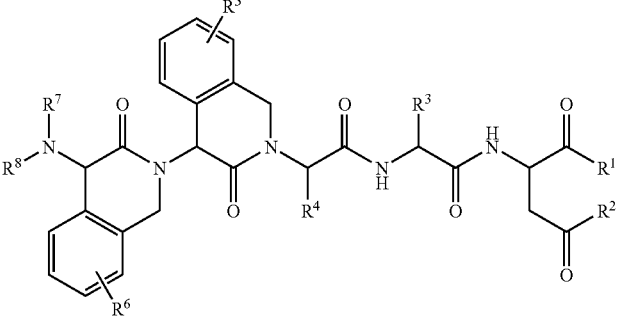 |

TABLE 10-continued

Constrained analogues of VDVAD (SEQ ID NO: 9) (compounds XV.1 to XV.15)

| No. | Structure |
|---|---|
| 9 | 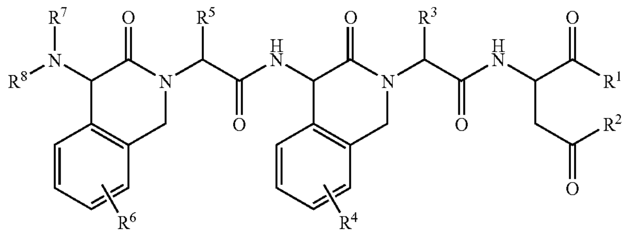 |
| 10 | 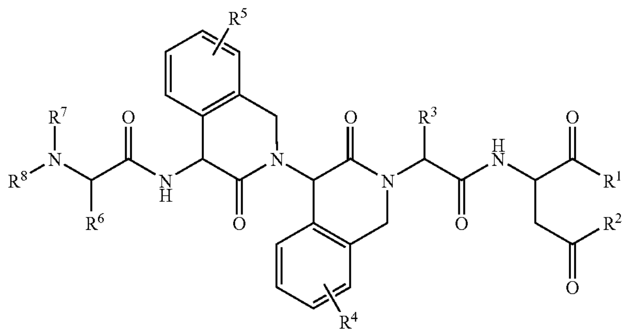 |
| 11 | 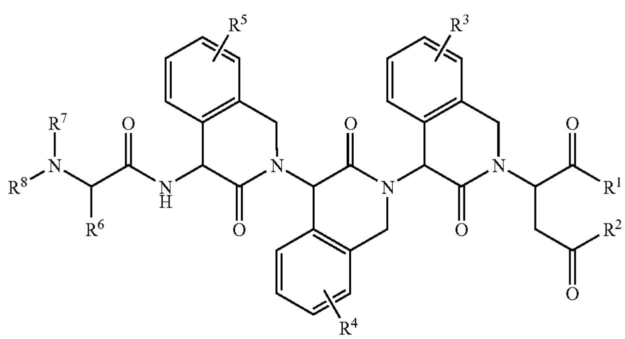 |
| 12 | 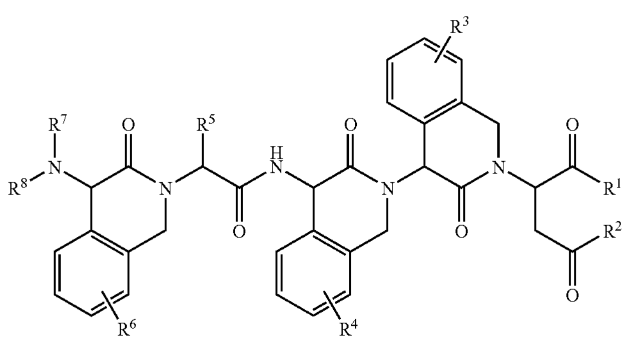 |

TABLE 10-continued

Constrained analogues of VDVAD (SEQ ID NO: 9) (compounds XV.1 to XV.15)

| No. | Structure |
|---|---|
| 13 | 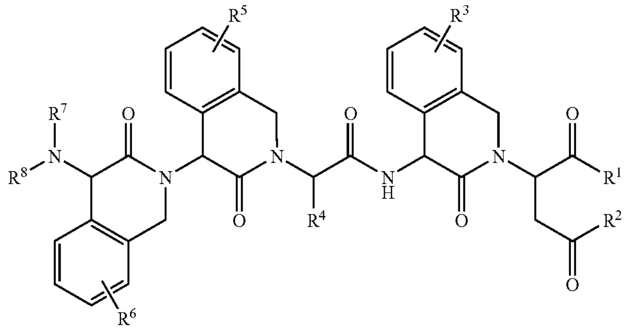 |
| 14 | 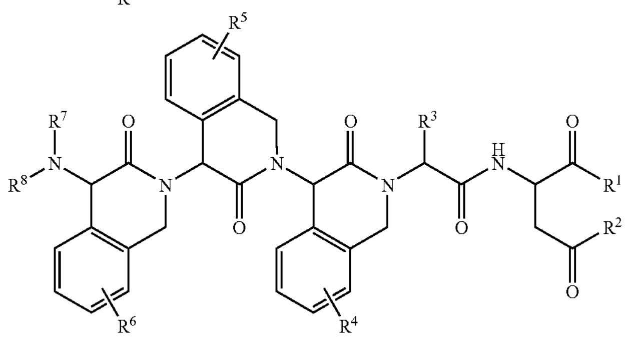 |
| 15 | 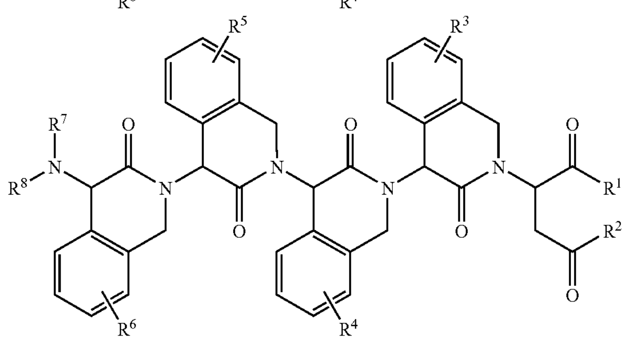 |

(e) The invention also relates to 1,2,3,4-tetrahydroisoquinoline-3-carboxamides XVI.1 to XVI.15 (Table 11) in which (i) the absolute configuration of each amino acid or its isostere is either L or D;
(ii) n, R, $R^1$, $R^2$, $R^3$, $R^4$, $R^5$, $R^6$, $R^7$, $R^8$, U, Y and Z are as described previously.

TABLE 11

Constrained VDVAD (SEQ ID NO: 9) analogues (compounds XVI.1 to XVI.15)

| No. | Structure |
|---|---|
| 1 | 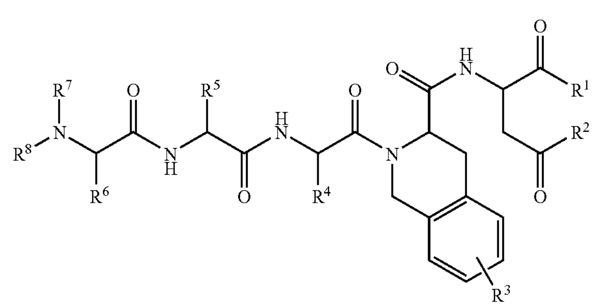 |

TABLE 11-continued

Constrained VDVAD (SEQ ID NO: 9) analogues (compounds XVI.1 to XVI.15)

| No. | Structure |
|-----|-----------|
| 2 | 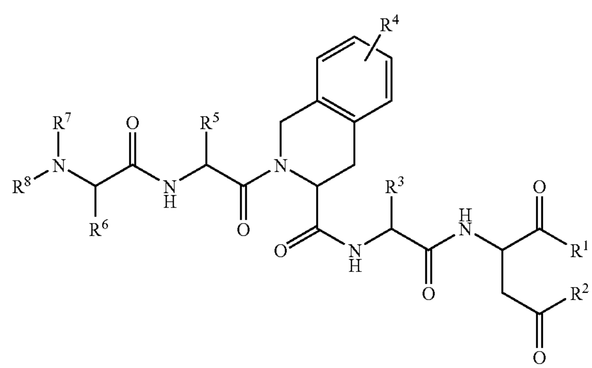 |
| 3 | 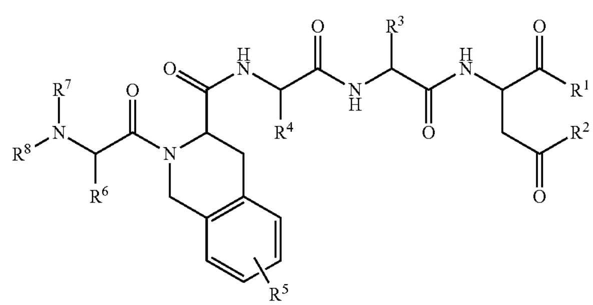 |
| 4 | 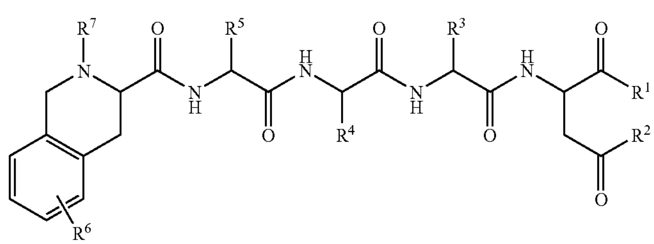 |
| 5 | 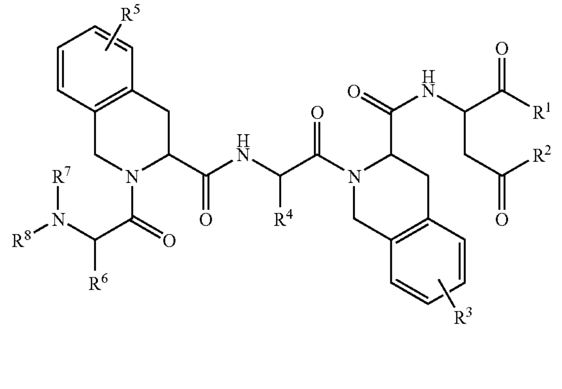 |

TABLE 11-continued
Constrained VDVAD (SEQ ID NO: 9) analogues (compounds XVI.1 to XVI.15)
| No. | Structure |
|---|---|
| 6 | 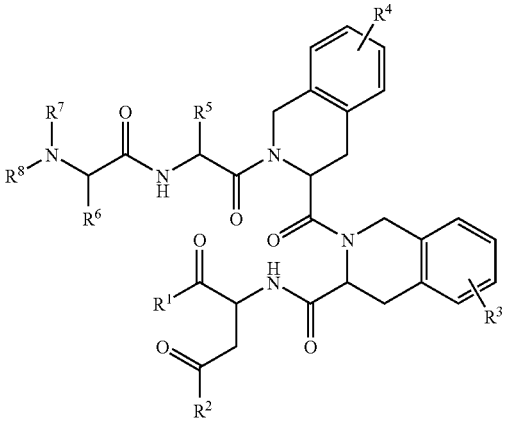 |
| 7 | 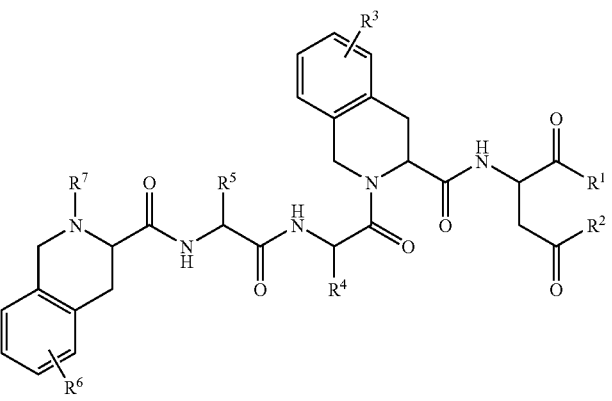 |
| 8 | 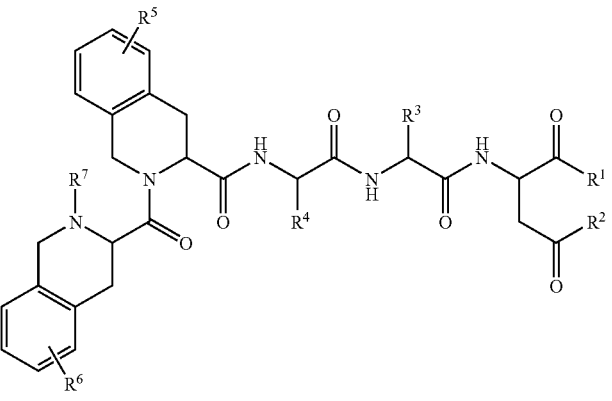 |
| 9 | 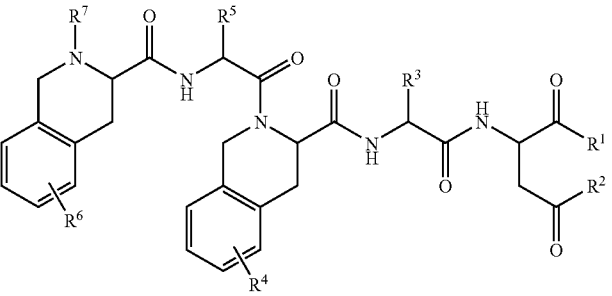 |

TABLE 11-continued
Constrained VDVAD (SEQ ID NO: 9) analogues (compounds XVI.1 to XVI.15)
| No. | Structure |
|---|---|
| 10 | 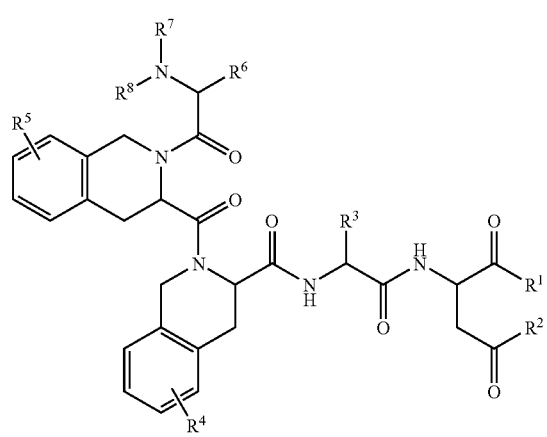 |
| 11 | 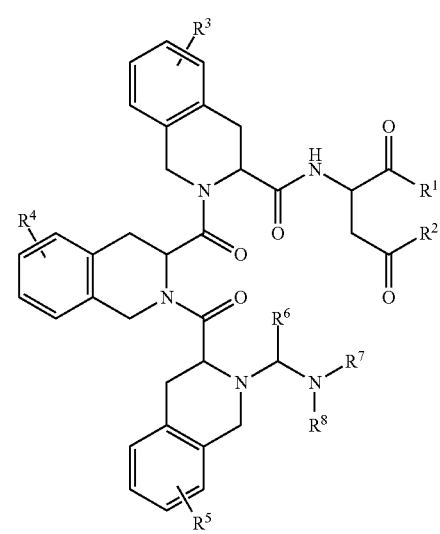 |
| 12 | 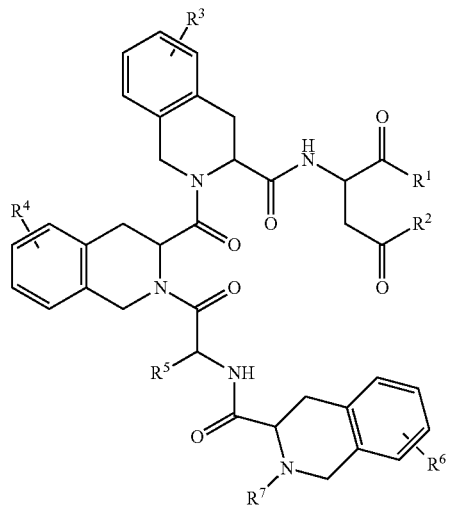 |

TABLE 11-continued

Constrained VDVAD (SEQ ID NO: 9) analogues (compounds XVI.1 to XVI.15)

| No. | Structure |
|---|---|
| 13 | 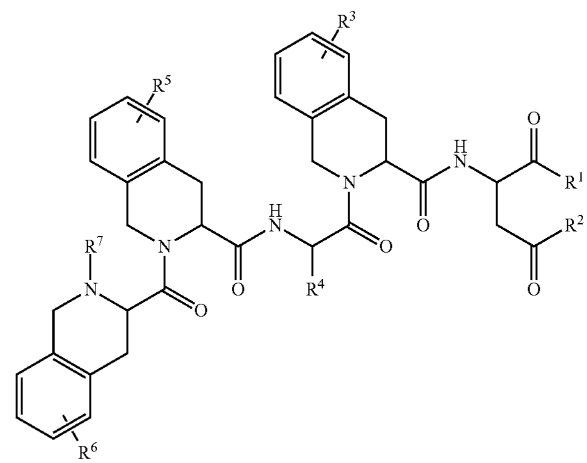 |
| 14 | 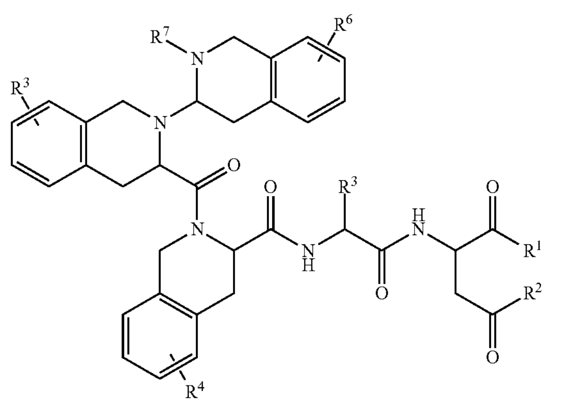 |
| 15 | 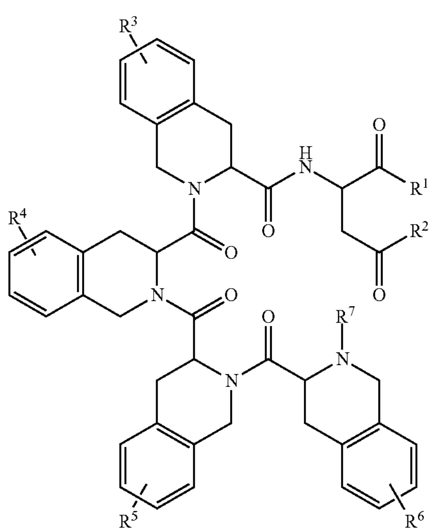 |

(f) The invention also relates to 4-amino-1,2,4,5-tetrahydrobenzo[c]azepin-3-ones XVII.1 to XVII.15 wherein
  (i) the absolute configuration of each amino acid or its isostere is either L or D;
  (ii) n, R, $R^1$, $R^2$, $R^3$, $R^4$, $R^5$, $R^6$, $R^7$, $R^8$, $R^9$, U, Y and Z are as described previously.

TABLE 12

Constrained VDVAD (SEQ ID NO: 9) analogues (compounds XVII.1 to XVII.15)

| No. | Structure |
|---|---|
| 1 | 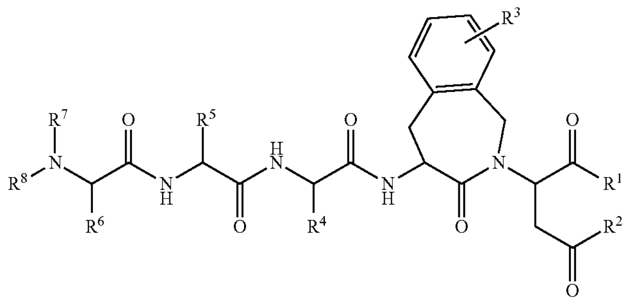 |
| 2 | 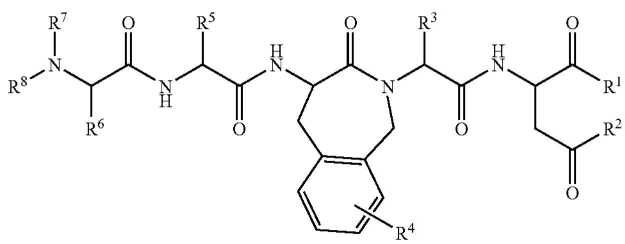 |
| 3 | 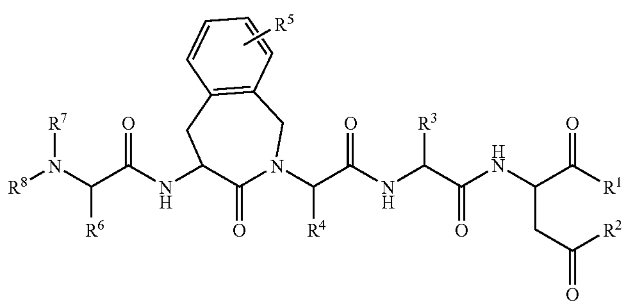 |
| 4 | 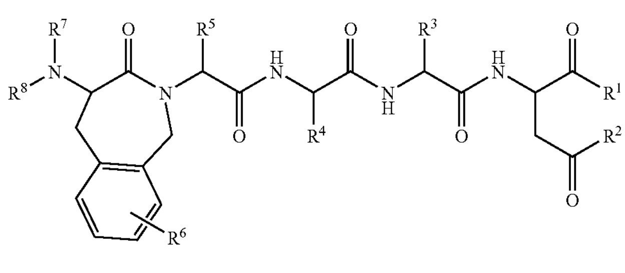 |

TABLE 12-continued

Constrained VDVAD (SEQ ID NO: 9) analogues (compounds XVII.1 to XVII.15)

| No. | Structure |
|-----|-----------|
| 5 | 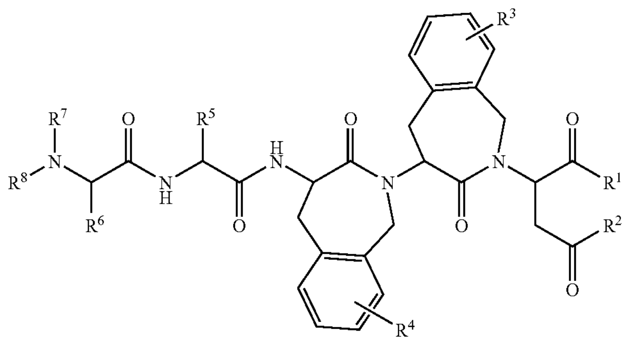 |
| 6 | 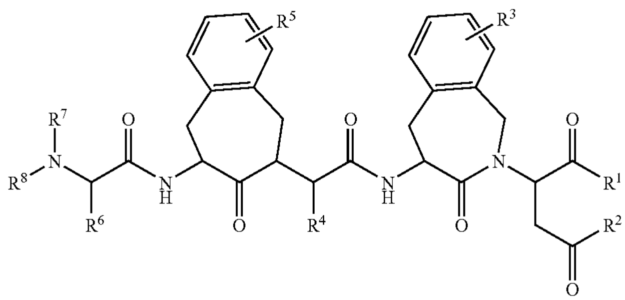 |
| 7 | 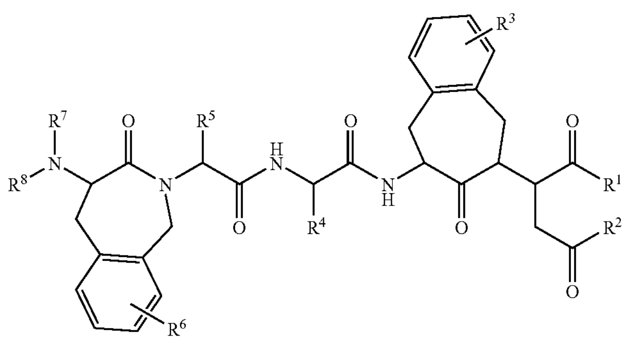 |
| 8 | 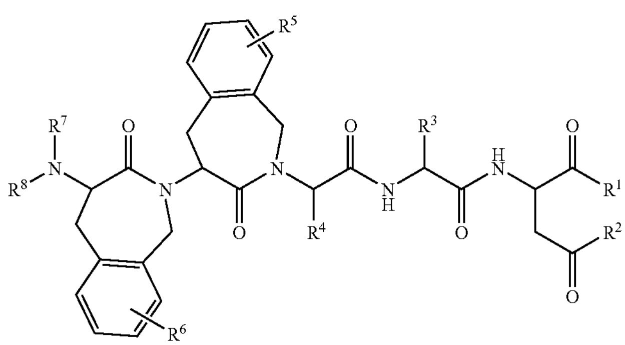 |
| 9 | 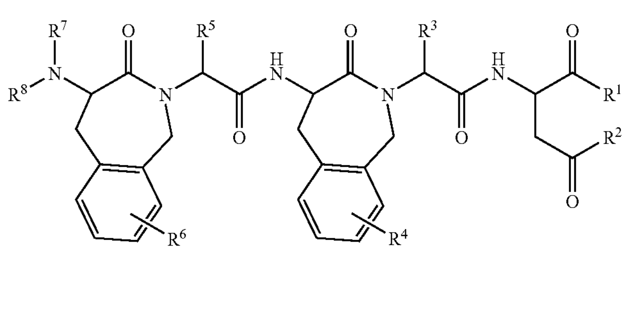 |

TABLE 12-continued

Constrained VDVAD (SEQ ID NO: 9) analogues (compounds XVII.1 to XVII.15)

| No. | Structure |
|-----|-----------|
| 10  | 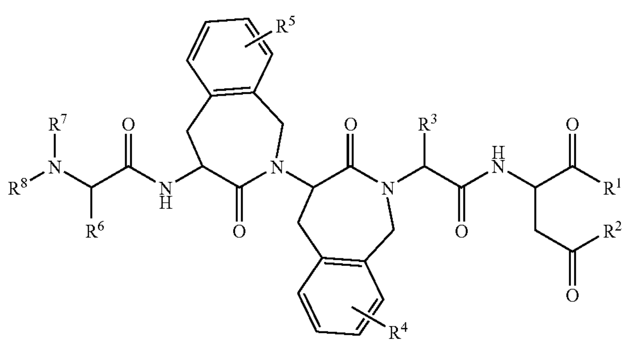          |
| 11  | 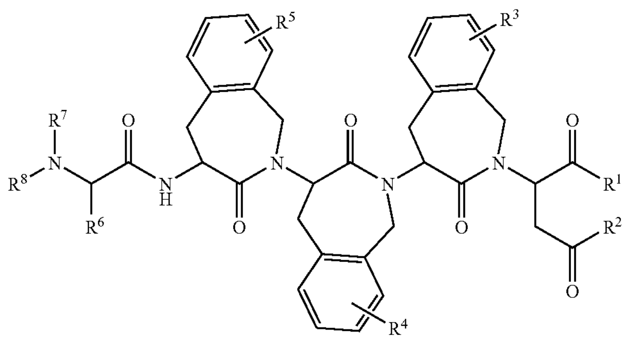          |
| 12  | 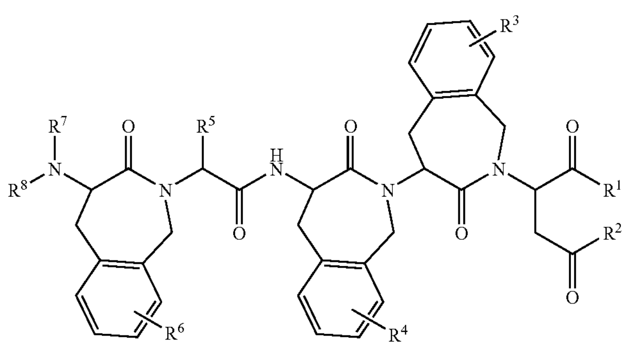          |
| 13  | 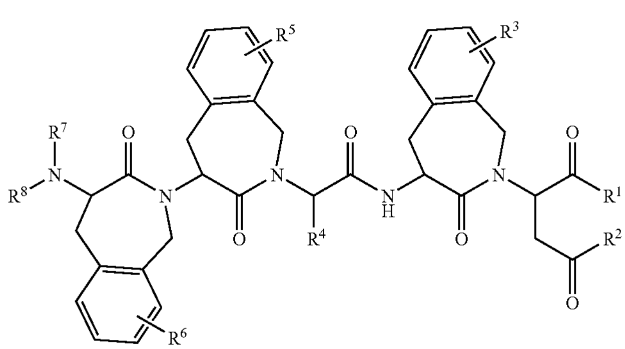          |

TABLE 12-continued

Constrained VDVAD (SEQ ID NO: 9) analogues (compounds XVII.1 to XVII.15)

| No. | Structure |
|---|---|
| 14 | 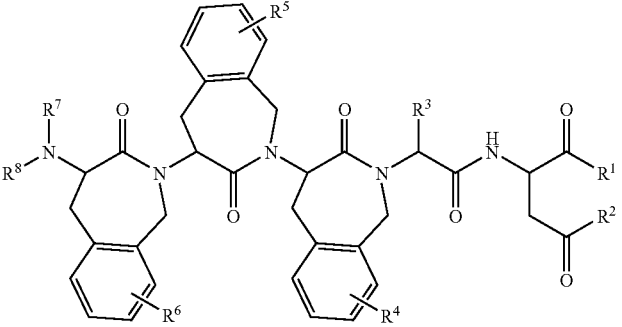 |
| 15 | 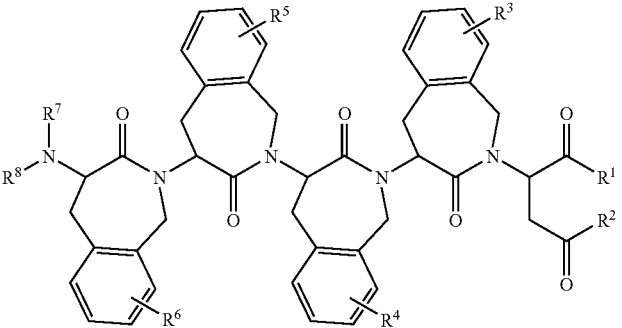 |

(g) The invention relates to 1,2,3,4-tetrahydronaphthalenes XVIII.1 to XVIII.15 in which
  (i) the absolute configuration of each amino acid or its isostere is either L or D;
  (ii) n, R, $R^1$, $R^2$, $R^3$, $R^4$, $R^5$, $R^6$, $R^7$, $R^8$, U, Y and Z are as described previously.

TABLE 13

Constrained amino acids XVIII.1 to XVIII.15

| No. | Structure |
|---|---|
| 1 | 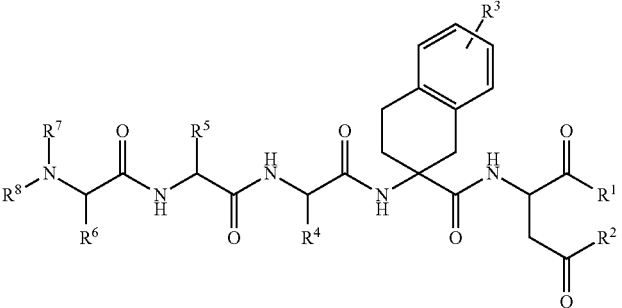 |

TABLE 13-continued

Constrained amino acids XVIII.1 to XVIII.15

| No. | Structure |
|---|---|
| 2 | 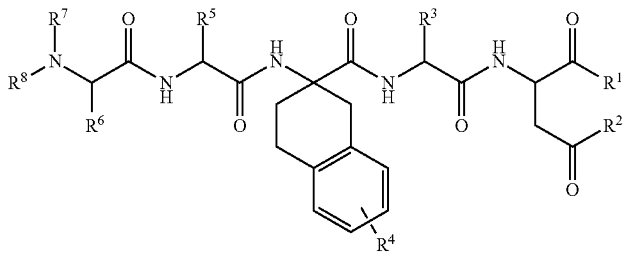 |
| 3 | 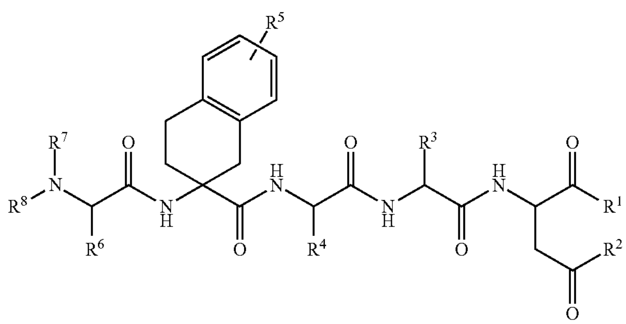 |
| 4 | 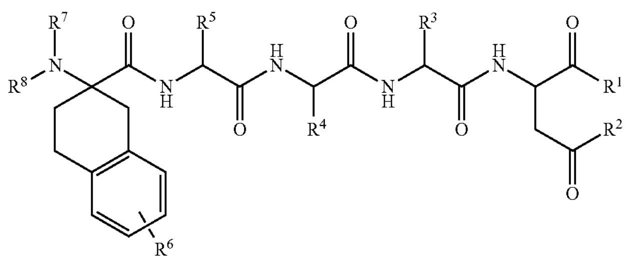 |
| 5 | 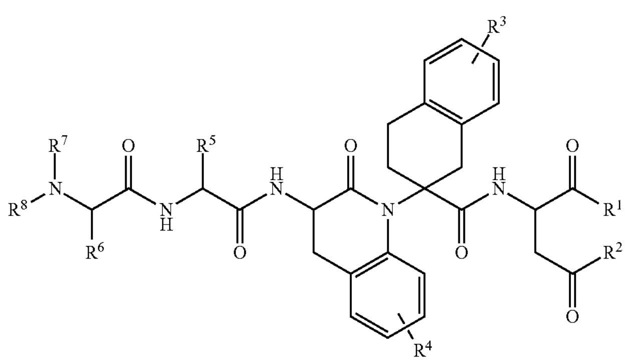 |
| 6 | 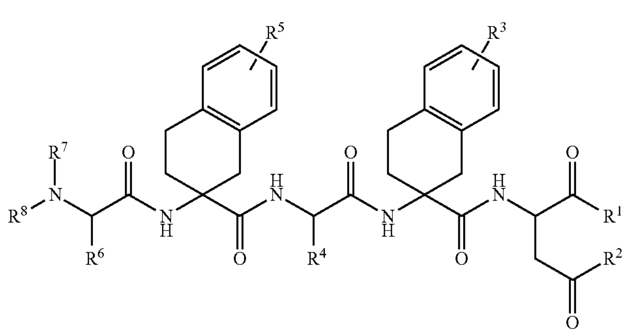 |

TABLE 13-continued

Constrained amino acids XVIII.1 to XVIII.15

| No. | Structure |
|---|---|
| 7 | 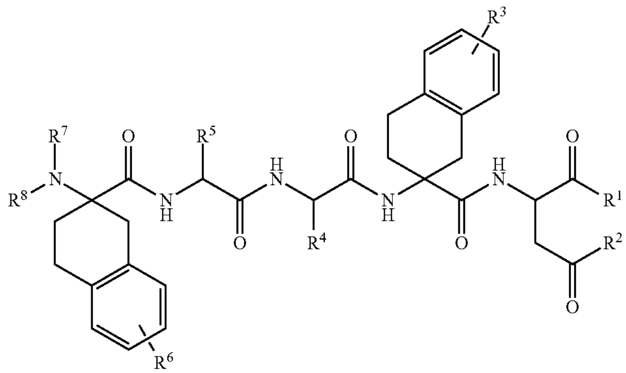 |
| 8 | 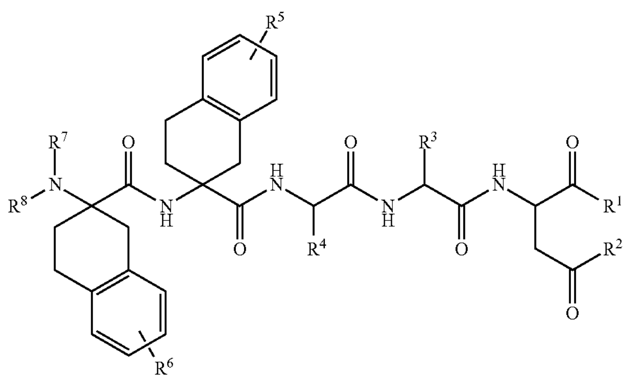 |
| 9 | 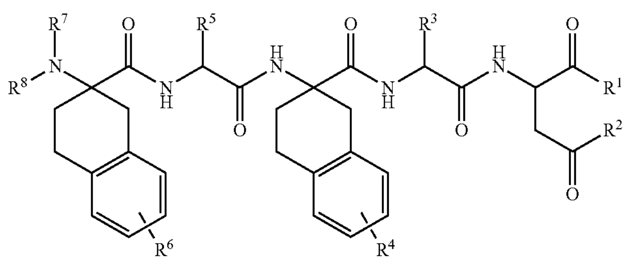 |
| 10 | 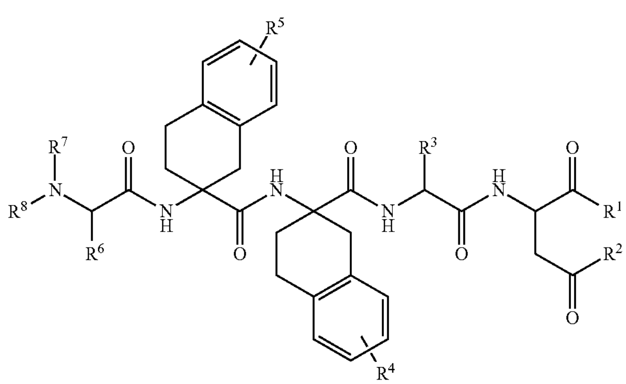 |

TABLE 13-continued

Constrained amino acids XVIII.1 to XVIII.15

| No. | Structure |
|---|---|
| 11 | 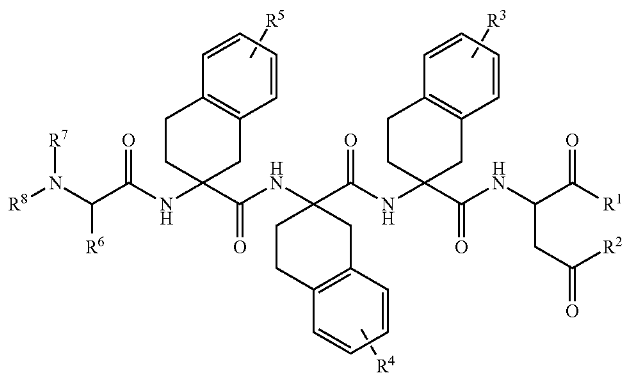 |
| 12 | 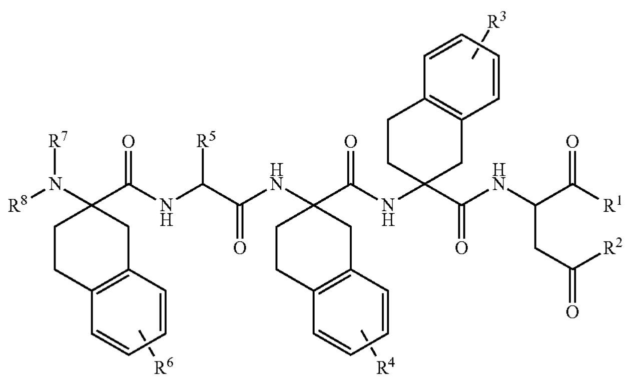 |
| 13 | 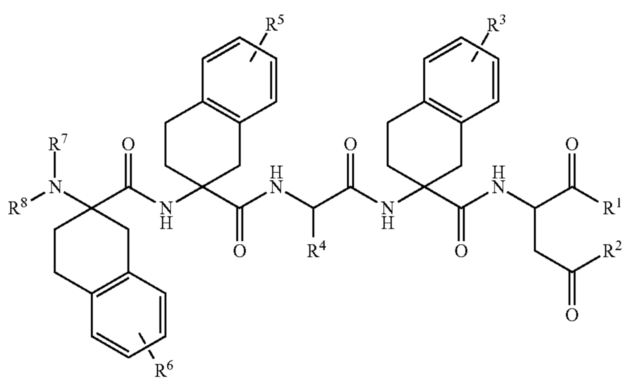 |
| 14 | 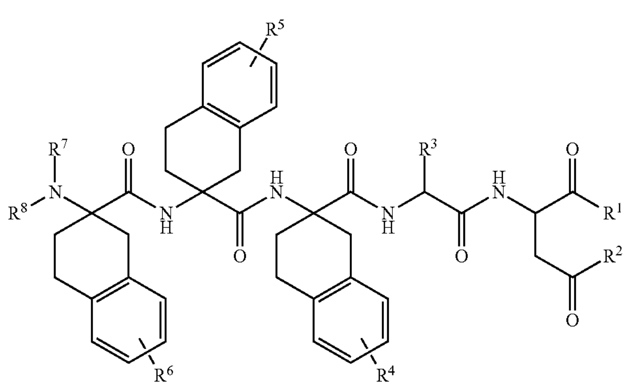 |

TABLE 13-continued

Constrained amino acids XVIII.1 to XVIII.15

| No. | Structure |
|-----|-----------|
| 15 | 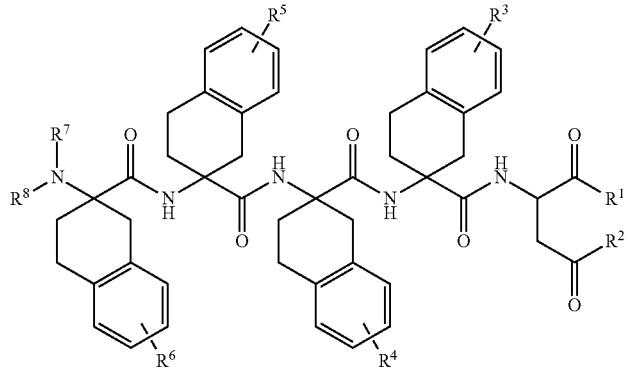 |

(h) The invention also relates to 2,3-dihydro-1H-indenes XIX.1 to XIX.15 (Table 14) in which
(i) the absolute configuration of each amino acid or its isostere is either L or D;
(ii) n, R, $R^1$, $R^2$, $R^3$, $R^4$, $R^5$, $R^6$, $R^7$, $R^8$, U, Y and Z are as described above.

TABLE 14

Constrained VDVAD (SEQ ID NO: 9) analogues (compounds XIX.1 to XIX.15)

| No. | Structure |
|-----|-----------|
| 1 | 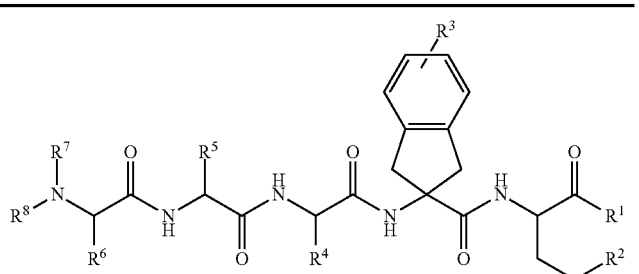 |
| 2 | 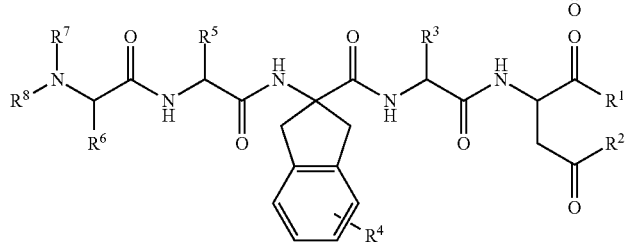 |
| 3 | 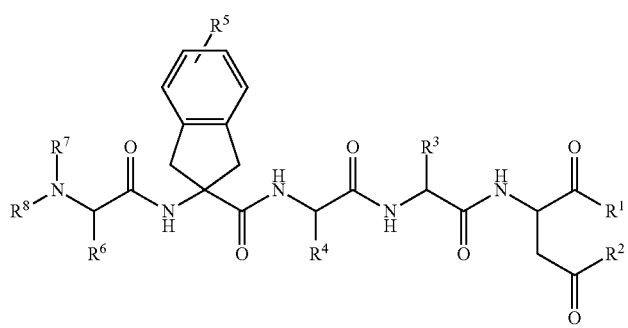 |

TABLE 14-continued

Constrained VDVAD (SEQ ID NO: 9) analogues (compounds XIX.1 to XIX.15)

| No. | Structure |
|---|---|
| 4 | 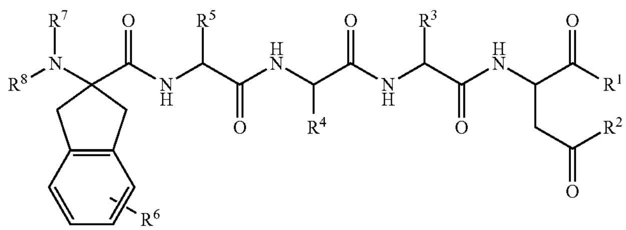 |
| 5 | 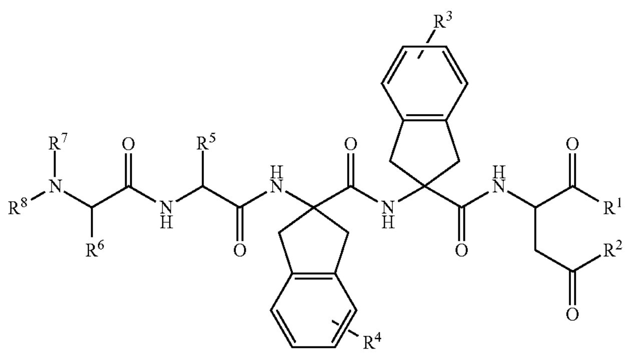 |
| 6 | 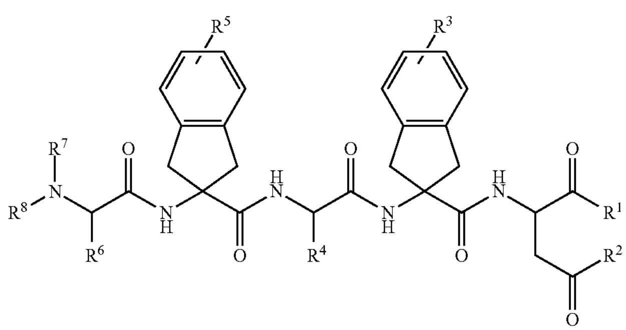 |
| 7 | 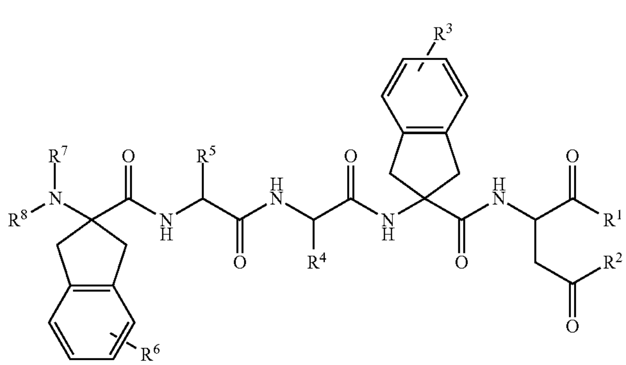 |

TABLE 14-continued
Constrained VDVAD (SEQ ID NO: 9) analogues (compounds XIX.1 to XIX.15)
| No. | Structure |
| --- | --- |
| 8 | 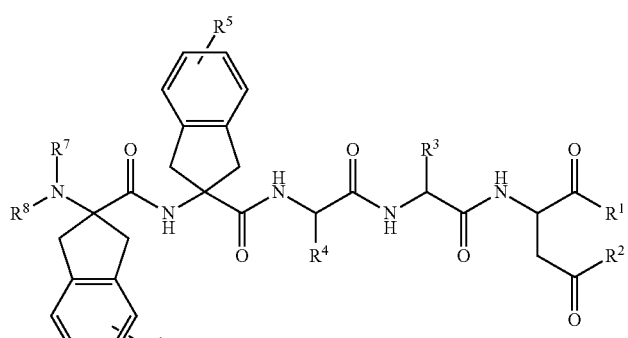 |
| 9 | 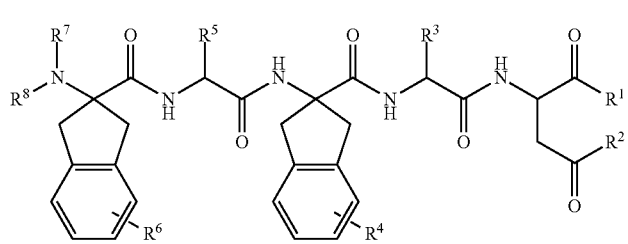 |
| 10 | 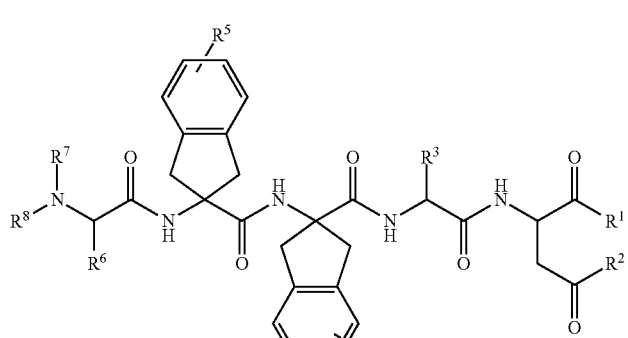 |
| 11 | 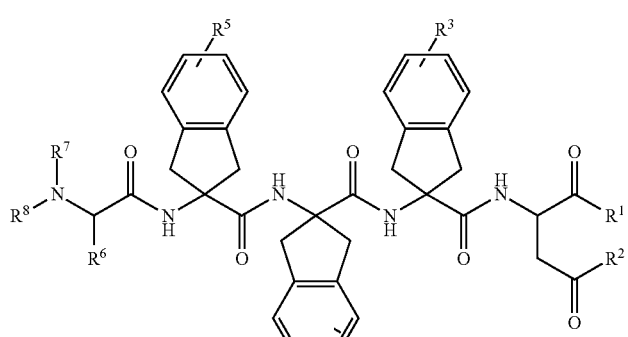 |

TABLE 14-continued

Constrained VDVAD (SEQ ID NO: 9) analogues (compounds XIX.1 to XIX.15)

| No. | Structure |
|---|---|
| 12 | 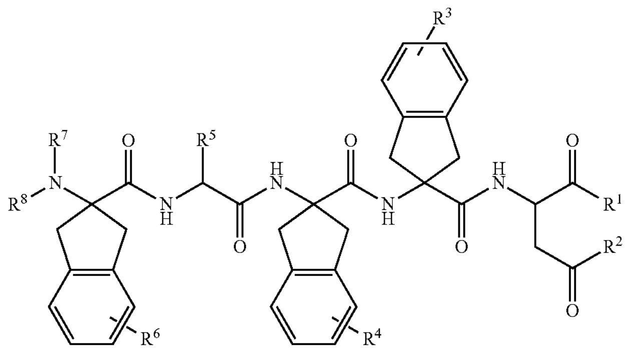 |
| 13 | 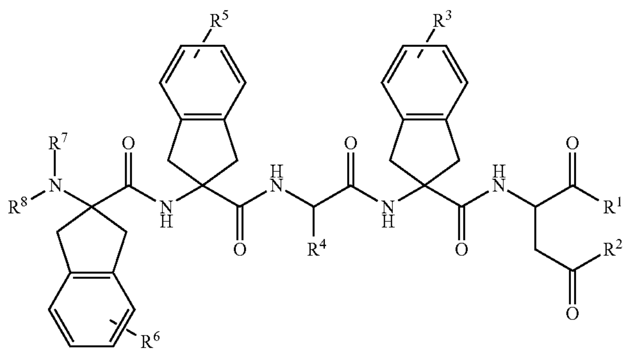 |
| 14 | 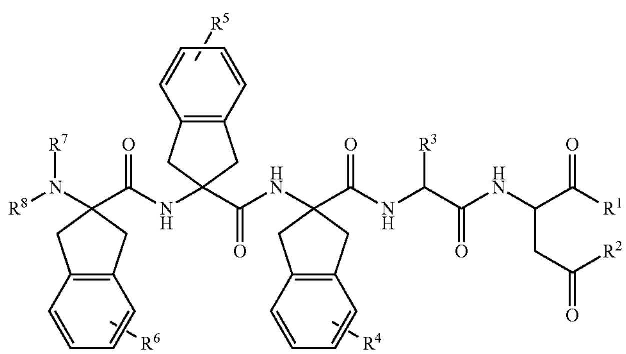 |
| 15 | 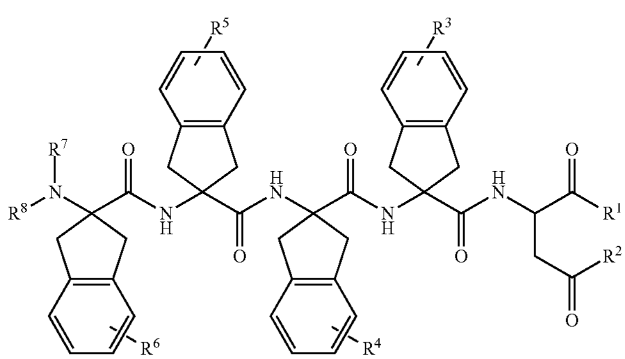 |

Said caspase-2-inhibitors are advantageously obtained by a synthetic route as illustrated in the examples. The derivatives of the structure given on schemes 1-3 will be obtained by the one skilled in the art by using chemical synthesis classical methods.

Figure 5:
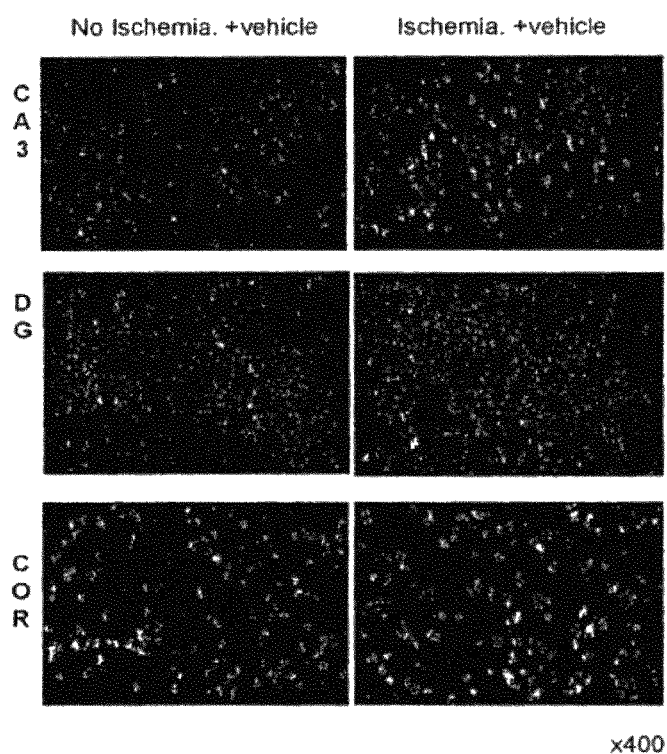

Other characteristics and advantages of the invention will be given in the following with reference to FIGS. 1 to 10, which represent, respectively:

FIGS. 1A-1D: the in vitro specificity and efficiency of Qco-VDVAD-dpf (SEQ ID NO:1) (Ac-VDVAD (SEQ ID NO:9)-AMC is referred to in FIG. 1A);

FIGS. 2A-2E: the selective caspase-2 inhibition by Qco-VDVAD-dfp (SEQ ID NO:1) strongly prevents cell death and cerebral infarct of rat neonates subjected to ischemic brain injury;

FIGS. 3A and 3B: the in vivo inhibition of caspase-2 activity and caspase-2 processing by Qco-VDVAD-dfp (SEQ ID NO:1) during neonatal ischemic brain injury;

FIGS. 4A-4D: the cell death in hippocampus and cortex of ichemic rats (4VO) model;

FIG. 5: the impact of ischemia on CA3, Dentus gyrus (DG) and cortex (COR);

FIGS. 6A-6C: the quantitation of cell death at 72 h post-ischemia;

FIGS. 7A-7C: the non-toxicity of Qco-VDVAD-dfp (SEQ ID NO:1) in non-ischemic rats;

FIGS. 8A-8B: the neuroprotection by Qco-VDVAD-dfp (SEQ ID NO:1) at 72 h post-ischemia (4VO) in the hippocampus of the young-adult rat;

FIGS. 9A-9C: the quantitative effect of Qco-VDVAD-dfp (SEQ ID NO:1) at 72 h post-ischemia; and FIGS. 10A-10C: the physiological and behavioural tests (Qco-VDVAD-dfp (SEQ ID NO:1)).

5. QCO-VDVAD-DFP (SEQ ID NO:1) IS A SELECTIVE CASPASE-2 INHIBITOR

5.1 Experimental Section 5.1.1 In vitro caspase activity assays. Human recombinant caspases 1 to 10 (25 U; QuantiZyme™ Assay System, BIOMOL, Plymouth, Pa., USA) were pre-incubated 30 min at 37° C. with Qco-VDVAD-dfp (SEQ ID NO:1) in assay buffer (50 mM HEPES, pH 7.4, 100 mM NaCl, 0.1% CHAPS, 10 mM DTT, 1 mM EDTA, 10% glycerol) and mixed with corresponding fluorogenic caspase substrates (500 μM; BIOMOL): Ac-YVAD(SEQ ID NO:3) -AMC (caspase-1), Ac-VDVAD(SEQ ID NO:9) -AMC (Caspase-2), Ac-DEVD (SEQ ID NO:4)-AMC (caspase-3/7), Ac-WEHD(SEQ ID. NO:5)-AMC (caspase-4/5), Ac-VEID(SEQ ID NO:6)-AMC (caspase-6), Ac-IETD(SEQ ID NO:7)-AMC (caspase-8), Ac-LEHD(SEQ ID NO:8)-AMC (caspase-9), or Ac-IETD(SEQ ID NO:7)-AMC (caspase-10). Substrate cleavage was assessed on a fluorescence microplate reader (TECAN, Genios; emission 510 nm, excitation 405 nm) and $IC_{50}$ value was determined from the dose-response sigmoid curves. Specific activity of each caspase was internally controlled with the corresponding specific inhibitors (1-2 μM, BIOMOL and MPBioMedicals). Other invtro assays were performed at CEREP or with CEREP protocols for calpains and granzyme-besed tests).

$IC_{50}$ determination was determined by incubating increasing concentration of Qco-VDVAD-dfp (SEQ ID NO:1) with recombinant caspase-2 in 100 μl assay buffer (50 mM HEPES, pH 7.4, 100 mM NaCl, 0.1% CHAPS, 10 mM DTT, 1 mM EDTA, 10% glycerol). The cleavage of 50 μM VDVAD (SEQ ID NO:9)-AMC by recombinant caspase-2 (125 U) was measured after 30 min at 37° C. on a fluorescence microplate reader by monitoring the fluorescence emission at 510 nm upon excitation at 405 nm.

5.1.2 Isolation, Culture of Primary Cortical Neurons and Apoptosis Induction.

Primary cortical neurons were cultured from E14 SWISS mice embryos (Janvier). Mice were sacrificed by cervical dislocation and embryos were removed by caesarean. Cerebral cortices were extracted and tissues mechanically triturated 15 times in L15 medium (Gibco BRL) by using 1000 μl tips (Eppendorf), then debris were removed, and the cell suspension was centrifuged at 850 rpm for 10 min. Neurons were plated for 2 days at a high density ($7 \cdot 10^5$ live cells per $cm^2$) in Eagle's Basal Medium (Eurobio) supplemented with 1% glutamine, 5% horse serum (HS, Eurobio) and 2.5% fetal calf serum (FCS, Eurobio) onto 6 or 24 well-plates (Sarstedt), or 4-well-Lab-Tek® chambered coverglasses (Nalge Nunc Internationnal), previously coated with 1 mg/ml polyethylenimine (Sigma). At DIV3, medium was changed daily and neurons were maintained in N5 complete medium containing 180 mg/l glucose, 5% HS and 1% FCS, and 3 μM cytosine β-D-arabinofuranoside (Sigma) and 1 μM 5-methyl-10,11-dihydro-5H-dibenzocyclohepten-5,10-imine maleate (MK-801, Sigma). Purity of culture (>95%) was controlled with an anti-Microtubule Associated Protein 2 monoclonal antibody (MAP-2, Sigma) and anti-Glial Fibrillary Acidic Protein polyclonal antibody (GFAP, Dako). Neurons were cultured used until 6 DIV on 24-well plate and subjected to serum deprivation. Briefly, neurons cultured in N5 complete medium were rapidly washed 3 times in N5 devoid of serum, and incubated for 24 hrs in N5 medium without serum, in absence or presence of Qco-VDVAD-dfp (SEQ ID NO:1).

5.1.3 Apoptosis assays. Analysis was performed on previously stained adherent neurons by fluorescence microscopy (FM) (DM IRB inverted fluorescence microscope, Leica, Rueil-malmaison, France) equipped with a 100 W mercury short arc lamp and a X 40 N PLAN L objective or a water immersion X 100 N PLAN objective. Usually, quantitative studies were performed by both FM on approximately 200-600 cells/field by scoring 5-10 random-selected fields per experiment and flow cytometry (FC) for higher sample throughput. FC analysis of apoptosis was performed after trypsinization of stained neurons by using a 3-color FACS-Calibur cytometer equipped with a 15 mW air-cooled 488 nm argon laser (Becton Dickinson). Activated caspase-2 was detected using specific FAM-conjugated peptides (called FLICA: CaspaTag™ fluorescein Caspase Activity Kits, Q-Biogen, Illkirch, France; ApoFluor™ Caspase Detection Kits, MP BioMedicals): FAM-VDVAD (SEQ ID NO:9)-fmk. Viability loss was assessed by 7-AAD (Sigma) incorporation.

5.1.4 Formulation studies. Compound Qco-VDVAD-dfp (SEQ ID NO:1) is soluble in Tween 20 or Pluronc F-68 excipients. Stability was followed throughout 7 days at RT or after freeze/thawing of aqueous solution comprising various 10-100% of excipients by using HPLC (Varian ProStar 410 equipped of Nucleosile $C_{18}$ (8 μm, 3.9×150 mm) with detection at 214 nm).

5.2 Results

Qco-VDVAD-dfp (SEQ ID NO:1) is a selective caspase-2 inhibitor (IC50=65-80 nM) with no cross reactivity against other caspases or at least 32 others related-proteases or enzymes involved in signal transduction and neuronal metabolism, nitric oxide pathway or prostanglandin metabolism (FIG. 1). Qco-VDVAD-dfp (SEQ ID NO:1) is cell-permeant because it prevents caspase-2 activity during serum-deprivation in cortical neuron cultures. In addition, Qco-VDVAD-dfp (SEQ ID NO:1) prevents neuronal death at 24 hrs in this experimental caspase-2 dependent cell death paradigm. (FIG. 1). Moreover Qco-VDVAD-dfp (SEQ ID NO:1) is suitable for animal or human administration because of its high solubility in Tween 20 or Pluronic-F68 based-mixtures. No degradation of Qco-VDVAD-dfp (SEQ ID NO:1) was found when left at room temperature until 7 days or after freeze/thawing.

These data are illustrated by the following figures:

FIG. 1: In vitro specificity and efficiency of Qco-VDVAD-dpf. (SEQ ID NO:1) (a) In vitro specificity of Qco-VDVAD-dfp (SEQ ID NO:1) on a panel of human recombinant caspases (1 to 10; 50 U). In vitro cleavage assays are performed with 0.1 µM of Qco-VDVAD-dfp (SEQ ID NO:1) (n=3; histograms indicate % of caspase activity±SD). (b) $IC_{50}$ (concentration that prevents 50% of Ac-VDVAD(SEQ ID NO:9)-AMC cleavage by human recombinant C2 (125 U)) determination range against recombinant human caspase-2: 65-80 nM (n=3 with different batches). (c) Cytoprotective effect of Qco-VDVAD-dfp on 24 h-serum(SD)-deprived neurons. Qco-VDVAD-dfp (SEQ ID NO:1) prevents caspase-2 activity and cell death at 24 hrs (n=3). (d) Inhibitory profile of Qco-VDVAD-dfp (SEQ ID NO:1) (1 µM) determined on 32 other in vitro pharmacology assays related to proteases, signal transduction and neuronal metabolism, nitric oxide pathway or prostanglandin metabolism (n=2).

Stability of formulation was determined by HPLC. Qco-VDVAD-dfp (SEQ ID NO:1) (5·10−3 M in physiological buffer containing 20% of Tween 20) was not degraded at RT after 7 days.

IV. Effects of Qco-VDVAD-dfp (SEQ ID NO:1) in Rats Following Focal Cerebral Ischemia Intro Stroke is the third most common cause of death in adults in the developed world, and an important cause of mortality and chronic neurological morbidity in children. Many strokes in children happen in the perinatal period, soon before birth or within the month after. Risk of ischaemic stroke in the mother also increases near the time of birth, and is 34 times more common in the 2 days before and 1 day after delivery than earlier in pregnancy or in the non-pregnant state. The heightened vulnerability to ischaemic stroke in both mother and child, and also to thromboses in non-cerebral sites is probably related to activation of coagulant mechanisms by parturition presumably an evolutionary adaptation to lessen the risk of hemorrhage at this crucial time.

Perinatal ischaemic stroke is a cerebrovascular event around the time of birth with pathological or radiological evidence of focal arterial infarction. Most perinatal strokes occur in the territory of the middle cerebral artery (MCA). There is a predominance of left hemisphere lesions, which may be caused by hemodynamic differences from a patent ductus arteriosus, or a more direct route involving the left common carotid. The distribution of cerebral infarction differs somewhat with gestational age-preterm infants tend to have multifocal lesions involving the cortical or lenticulostriate branches of the MCA, whereas full-term infants tend to have occlusions of the main branch.

1. Experimental Model 1.1 Transient Unilateral Focal Ischemia Model

Newborn Wistar rats (dam plus 9 pups per litter) were obtained from Janvier (Le Genest-St-Isle, France) when the pups were 3-4 days of age. The pups were housed with their dam under a 12:12 h light-dark cycle with food and water freely available. Animal experimentation was conducted according to the French and European Community guidelines for the care and use of experimental animals. Ischemia was performed in 7 day-old rats (17-21 g), as previously described (Renolleau et al., 1998). Rat pups were anesthetized with an intraperitoneal injection of chloral hydrate (350 mg/kg). Anesthetized rats were positioned on their back and a median incision was made in the neck to expose the left common carotid artery. Rats were then placed on the right side and an oblique skin incision was made between the ear and the eye. After excision of the temporal muscle, the cranial bone was removed from the frontal suture to a level below the zygomatic arch. Then, the left middle cerebral artery, exposed just after its appearance over the rhinal fissure, was coagulated at the inferior level of the cerebral vein. After this procedure, a clip was placed to occlude the left common carotid artery. Rats were then placed in an incubator to avoid hypothermia. After 50 min, the clip was removed. Carotid blood flow restoration was verified with the aid of a microscope. Neck and cranial skin incisions were then closed. During the surgical procedure, body temperature was maintained at 37-38° C. Pups were transferred in an incubator (32° C.) until recovery then after to their dams.

Qco-VDVAD-dfp (SEQ ID NO:1) was administered intraperitoneally at a dose ranging from 0.001 to 10 mg/kg 5-15 min before the ischemic onset or 1 h after ischemia. Control animals received an equivalent volume of 0.9% saline containing 10% DMSO (n=15), the vehicle required to solubilize the caspase inhibitors (vehicle-treated group). The mortality rate during ischemia or before killing did not differ between Qco-VDVAD-dfp (SEQ ID NO:1) and vehicle-treated groups (<4%). Rats were killed 48 hours after reperfusion and brains were removed. The infarct lesion (pale zone) was visually scored by an observer blinded to the treatment of animals. Brains without a clear ischemic pale zone were observed under a magnifying glass. Those exhibiting no clear MCA occlusion were discarded.

Sixteen sections from anterior striatum to posterior hippocampus (corresponding to plates 9 to 27 in Paxinos' rat brain atlas) were selected, taken at equally spaced 0.5-mm intervals. The lesion areas were measured on cresyl violet-stained sections using an image analyzer (NIH image software), and the distances between respective coronal sections were used to calculate the infarct volume. Brain sections were processed for DNA strand breaks (TUNEL assay) using the in situ Fluorescein Cell Death Detection Kit (Roche, Meylan, France) according to manufacturer's instructions.

For Tunnel analysis, brains were then fixed 2 days in 4% buffered formaldehyde. Fifty-micrometer coronal brain sections were cut on a cryostat and collected on gelatin-coated slides.

Statistical analysis was performed as followed. Assuming a beta risk of 0.2 and an alpha risk of 0.05, it was estimated that 15-16 animals in each group were needed to detect a 50% infarct volume reduction between two groups. Because three groups of animals are compared in the experiments, these values are only informative. A predetermined list with blocks of six animals was used to randomized the animals among the three groups. An investigator blind to the treatment condition did all measurements. The difference between the means was assessed by the non-parametric multiple comparison test of Kruskall-Wallis, followed by the Newman-Keul's test for non-parametric values. We consider differences to be significant at the 5% level (P<0.05).

1.2 In Vitro VDVAD(SEQ ID NO:9)-AMC Cleavage in Brain Lysates and Caspase-2 Cleavage by Western Blot Analysis Protein Extraction and Western Blot Analysis Brain hemispheres were lysed in 10 mM Hepes, 5 mM $MgCl_2$, 42 mM KCl, 1 mM DTT, 0.5% CHAPS supplemented by complete protease inhibitors cocktail (Roche, Meylan, France) by using a manual potter on ice. Homogenates were centrifuged at 10000 g/4° C. for 10 min before keeping surnageant. Protein concentration was determined using BCA test. Proteins (50 µg) were separated on 12.5% polyacrylamide gels and transferred to PVDF membranes (Amersham). Immunostaining was revealed using ECL (Amersham Pharmacia Biotech). The monoclonal anti-mouse caspase-2 antibody (52 kDa; 11B4, Alexis Biochemicals) was used at a 1:1000 dilution; actin (42 kDa; Sigma; antibody diluted 1:5000) is used as an equal loading control.

Caspase-2 activity (100 µg protein brain sample) was assessed in 100 µl assay buffer (50 mM HEPES, pH 7.4, 100 mM NaCl, 0.1% CHAPS, 10 mM DTT, 1 mM EDTA, 10% glycerol). The cleavage of 50 µM VDVAD(SEQ ID NO:9)-AMC by recombinant caspase-2 was measured after 2 h at 37° C. on a fluorescence microplate reader by monitoring the fluorescence emission at 510 nm upon excitation at 405 nm. For inhibition of VDVADase activity, inhibitors (2 µM) were pre-incubated 30 min at 37° C. in presence of caspase-2 prior to subsequent incubation with 50 µM VDVAD(SEQ ID NO:9)-AMC (30 min, 37° C.). No noticeable fluorescence background was observed with VDVAD(SEQ ID NO:9)-AMC alone.

2. Results

In this transient unilateral focal ischemia model, rat pups underwent permanent left middle cerebral artery occlusion in association with transient occlusion of the left common carotid artery with reperfusion. Brains were then analyzed 48 hours later, a time point at which the infarct was stabilized without significant edema (no more than 1.5%). Ischemia induced an infarct volume of $55.0\pm3.4$ mm$^3$, which represents a $22.1\pm1.4\%$ damage in the lesioned ipsilateral hemisphere. Infarct volumes appeared normally distributed (between 15 and 26%) (FIG. 2). A single dose of Qco-VDVAD-dfp (SEQ ID NO:1) (5 mg/kg; i.p.) was administered to rat pups before the ischemic onset. This single dose induced a highly significant 74% reduction in infarct volume ($5.7\pm2.3\%$, $p<0.01$ ((median=0.5) compared to the control group ($V=22.1\pm1.4\%$, median=21) in the Newman-Keul's test) (FIG. 2). Interestingly, On the 12 studied animals, four Qco-VDVAD-dfp (SEQ ID NO:1)-treated animals display intermediate protection ($V=16.5\pm1.32\%$) and eight animals display either complete protection or a very marked smaller infarct (median=0.5%), visible only at the level of the middle cerebral artery (levels corresponding to plates 12 and 13) but not at that of the dorsal) and hippocampus (plate 21) compared to the ischemic control animals (FIG. 2).

A single dose of Qco-VDVAD-dfp (SEQ ID NO:1) (0.1 mg/kg; i.p.) was administered 1 h after MCAO (corresponding to the beginning of reperfusion) to rat pups. This single dose induced a highly significant 44% reduction in infarct volume ($9.95\pm2.8\%$, $p<0.01$ compared to the control group ($V=22.64\pm1.6\%$) in the Newman-Keul's test) (FIG. 2).

In addition, terminal transferase dUTP nick end labeling (TUNEL) is significantly decreased in Qco-VDVAD-dfp (SEQ ID NO:1)-treated animals (FIG. 2).

The protective effect provided by Qco-VDVAD-dfp (SEQ ID NO:1) is not mediated by corporal temperature regulation (FIG. 2).

Figure 3:
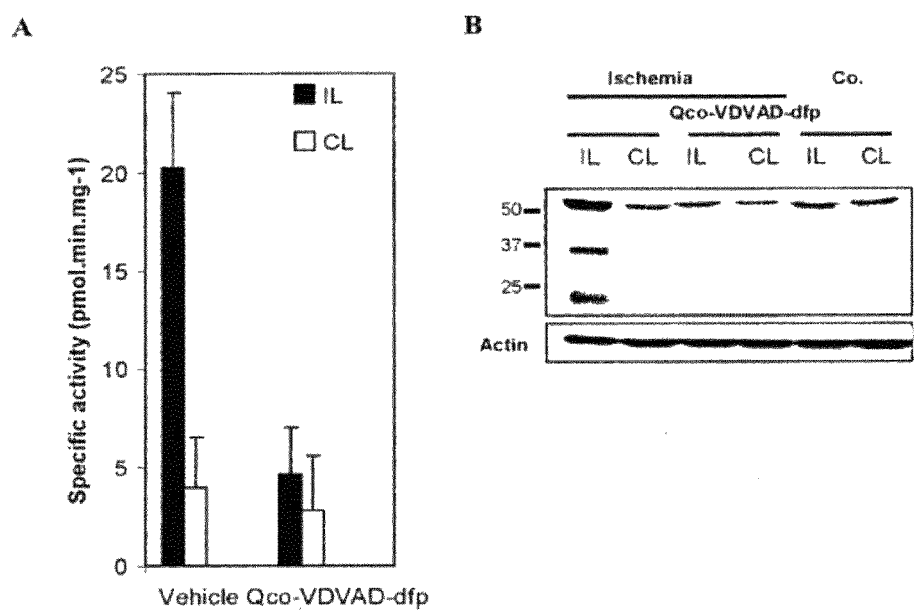

Finally, Qco-VDVAD-dfp (SEQ ID NO:1) well target in vivo caspase-2: effectively, it inhibited caspase-2 activity as well as caspase-2 processing in brain of ischemic rat pups (FIG. 3).

We demonstrate that caspase-2 is a relevant target with good neuroprotective prognosis in neonatal stroke, since in vivo inactivation of caspase-2 results in massive reduction of infarct volume during transient focal ischemia. We suggest that caspase-2 may be a valid target for in vivo prevention of hypoxic-ischemic encephalopathy at birth and perinatal stroke, a major health care in human newborns.

These data are illustrated by the following figures:

FIG. 2: Selective caspase-2 inhibition by Qco-VDVAD-dfp (SEQ ID NO:1) strongly prevents cell death and cerebral infarct of rat neonates subjected to ischemic brain injury. (a, left panel) Mean infarct volumes at 48 hrs after ischemia in vehicle-(n=17) and Qco-VDVAD-dfp-(SEQ ID NO:1) (i.p., 5 mg/kg; n=12) treated rats (mean±SEM). Qco-VDVAD-dfp (SEQ ID NO:1) induces 74% reduction ( * * * =p<0.001, Kruskall-Wallis test) when administrated 5-15 min before ischemic onset; (a, right panel) Qco-VDVAD-dfp (SEQ ID NO:1) treatments provide 2 groups displaying high/total (height) or low protection (four). Single infarct volume data are plotted. Bold and thin horizontal bars represent the group median and mean, respectively. (b) Representative cresyl violet-stained coronal sections from animals at 48 hrs post-reperfusion at the level of dorsal hippocampus (plate 21, Paxinos' rat brain atlas) and anterior commissure (plate 12). Dotted lines indicate infarct area. Arrow indicates the absence of infarct in Qco-VDVAD-dfp(SEQ ID NO:1)-treated animal. Bar represents 130 µm. (c, left panel) Mean infarct volumes at 48 hrs after ischemia in vehicle- (n=22) and Qco-VDVAD-dfp-(SEQ ID NO:1) (i.p., 0.1 mg/kg; n=19) treated rats (mean±SEM). Qco-VDVAD-dfp (SEQ ID NO:1) induces 44% reduction ( * * * =p<0.001, Kruskall-Wallis test) when administrated 1 h after ischemic onset. (c, right panel) Single infarct volume data are plotted. Bold and thin horizontal bars represent the group median and mean, respectively. (d) Cell death in the ipsilateral cortex of vehicle- and Qco-VDVAD-dfp (SEQ ID NO:1)-treated animals. Representative fluorescence micrographs (from plate 12) after in situ 3'OH end DNA labelling (bar: 100 µm). (e) Corporal temperature was measured before and after Qco-VDVAD-dfp (SEQ ID NO:1) administration (pre and post-ischemia).

FIG. 3: Ischemic rat pups were treated with 5 mg/kg (i.p) of Qco-VDVAD-dfp(SEQ ID NO:1). Animals were sacrificed at 24 hrs. Brain homogenates were subjected to caspase-2 activity assay and western blot analysis. IL: ipsilateral injured hemisphere, CL: contralateral unlesionned hemisphere. (a) Caspase-2 activity determination in vehicle versus Qco-VDVAD-dfp(SEQ ID NO:1)-treated rats. (b) Western blot analysis of caspase-2 processing in brain homogenates from vehicle-versus Qco-VDVAD-dfp(SEQ ID NO:1)-treated rats.

V. Effects of Qco-VDVAD-dfp (SEQ ID NO:1) in Rats Following Global Cerebral Ischemia Global cerebral ischemia is a condition that may be induced after cardiac arrest or cardiovascular disturbances, and that results in both blood flow reduction and hypoxia. Lesions appear in selectively vulnerable brain regions and neurons may be damaged by apoptosis during such global cerebral ischemia. Global ischemia results also in widespread and global loss of energy metabolites combined with diffuse brain edema and global damage. Mechanisms involved in lesion growth may include cystein-proteases (caspases) activation, excitotoxicity, peri-infarct depolarizations, lactacidosis, microcirculatory disturbances, and flow-metabolism uncoupling among others. If some (executionner) caspases may be activated during global ischemia, no one can comment on the role of caspase-2 in such pathological situations. Recently, we have developped a new selective caspase-2 inhibitor (2-Quinolinylcarbonyl-L-Valinyl-L-Aspartyl (methyl ester)-L-Valinyl-L-Alaninyl-L-Asparty (methyl ester) 2,6-difluorophenyl ester(SEQ ID NO:1), nammed Qco-VD- VAD-dfp(SEQ ID NO:1), that provided strong in vivo neuroprotection during neonatal cerebral ischemia. Here we investigated its cytoprotective-mediated effects against cerebral lesions occurring after cardiac arrest and behavioural-related benefits. Thus we tested Qco-VDVAD-dfp(SEQ ID NO:1)'s effect in an in vivo experimental model of global and transient cerebral ischemia (4VO, four vessel occlusion) in the young adult rat, based on Pulsinelli's one (1979).

1 Experimental Model 1.1 VO Model

Global cerebral ischemia was induced by four-vessel occlusion (4VO) according a Pulsinelli's derived method (Pulsinelli et al., 1982; Pulsinelli and Buchman, 1988) in young-adult rats (males Wistar aged of 10-12 weeks, 320 g+/−10 g; Janvier). The first day, head of anesthetised rats was positionned in stereotaxic ear bars and tilted down at approximatively 30° to the horizontal. After a midline incision at the level of cervical spine, both vertebral arteries were exposed under microscope and then coagulated by electocautery needle through the alar foramina at the level of first cervical vertebra. Both common carotides were then exposed 24 h later and clamped for 20-30 min (rats fell in the coma when electrocautherisation of both vertebral arteries have been well performed). Carotid arteries were then declamped to allow blood flow reperfusion. Vehicle and Qco-VDVAD-dfp (SEQ ID NO:1) (II, n=0) were administrated at the level of the left cerebral ventricule in the first fifth minutes of ischemia (carotides occlusion). Rats were let in their cage with waer et food ad libitum.

1.2 Estimation of Cytoprotection

The selective loss of vulnerable cells and Qco-VDVAD-dfp(SEQ ID NO:1)'s effects (intracerebroventricular (ICV) administrated) have been evaluated at 72 h. Rats were sacrificed and brain fixed by trans-cardiac perfusion with paraformaldehyde. Frontal brain slices (25 μm) were strained by Cresyl-Violet or co-stained by Hoechst 33342 and Fluorojade B to assess cell death in the hippocampus and in the cortex. Cresyl-Violet is a pink-red dye that labels cytoplamic body Nissl (endoplasmic reticulum structures) and nuclei in living cells thus resulting in pale or absence of staining in dying cells. Fluoro JadeB (green fluorescence) intake is possible only in cells which have permeable plasma membrane, thus more caracteristic of dying cells. Hoechst 33342 (blue fluorescence) label nuclei all all cells and allows to appreciate nuclear morphology changes during cell death.

Cells were counted at the level of canula, as well as 650 μm and 780 μm after the cannula (antero-posterior axis) in the left brain hemisphere. Cells are counted in three successives slices at such levels in the hippocampus (CA1, CA3, girus dentus) and cortex. Cresyl-Violet stained slices were observed under white light (Nikon Eclipse E 800M microscope equipped with ×40 et ×20 objectives and LEICA IM50 software). Both Fluoro Jade B and Hoechst stained slices were observed under a Leica DMIRB inverted fluorescence microscope equiped with ×40 objective and LEICA IM1000/Qfluorobase software (BP 340-80 excitation filter combined with LP 425 emission filter for Hoechst; BP 480/40 excitation filter combined with BP 515-560 emission filter for Fluoro Jade B).

1.3 Estimation of Behavioural Gain

Corporal temperature was measured during churgical procedure at day 1 (from anesthesia to stepl (vertebral electrocauterisation and cannula putting up) and step 2 (coratid isolation) of chirurgical procedure during. Corporal temperature was also measured 0, 10, 20 minutes after the beginning of ischemia, at day 2. Temperature was measured 24, 48, 72 H post-ischemia and before final anesthesia for perfusion at day 5. Behavioural studies (feeding, spontaneous activity and reactivity) were performed and evaluated by scoring.

Feeding: observation of stomacal contains at day 5
If refeeding=1; If no refeeding=0

Spontaneous activity: general behaviour of animals in their cage (alternance of active versus inactive phases) and reaction to prehension)
Vivacity=1; More or less vivacious=0.5; No or poor vivacity=0.

Reactivity: animal are sensitive and reactive to noise and move to the origin of the noise.
If curious=1; If relatively curious=0.5; If not very curious=0.

2 Results

Figure 6:
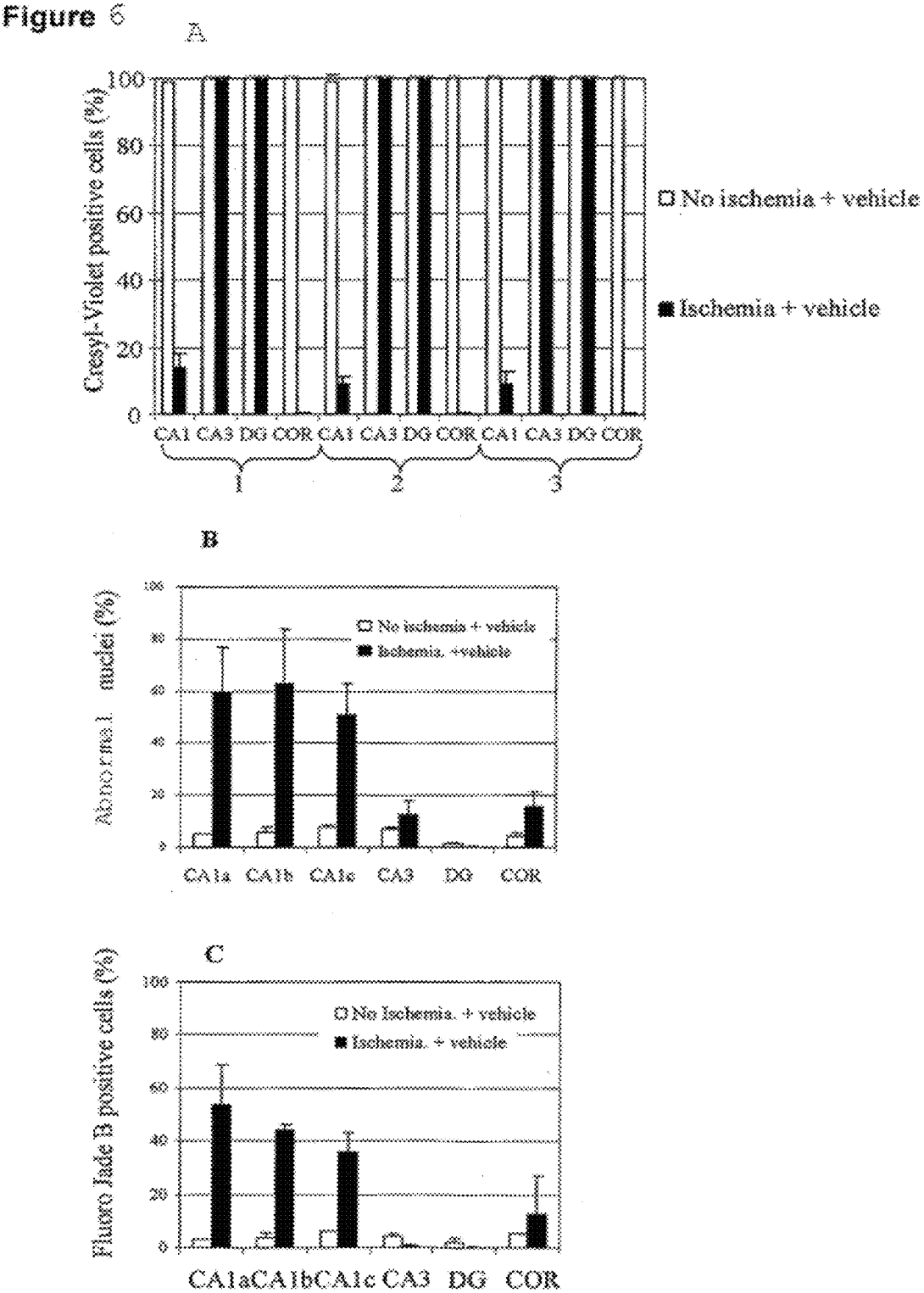

FIGS. 4-6 show that cell death occur at the level of CA1 in the hippocampus (and a few in the cortex) of 72 h post-ischemic adult rats: 90-100% of cells have lost their Cresyl-violet labelling and have abnormal cellular morphologies, 40-60% exhibited nuclear alteration, and 40-50% retained FluoroJade B in the CA1 (CA1a, b and c sub-areas) of ischemic brain. No sign of cell death was found in CA3, DG (Dentus girus) (also in CA2 and CA4, data not shown). Ischemia was also controlled by the presence of microglial cells that exhibit stick (resident microglia) or sickle (migrant microglia invading the brain after blood brain barrier rupture) shapes.

Figure 7:
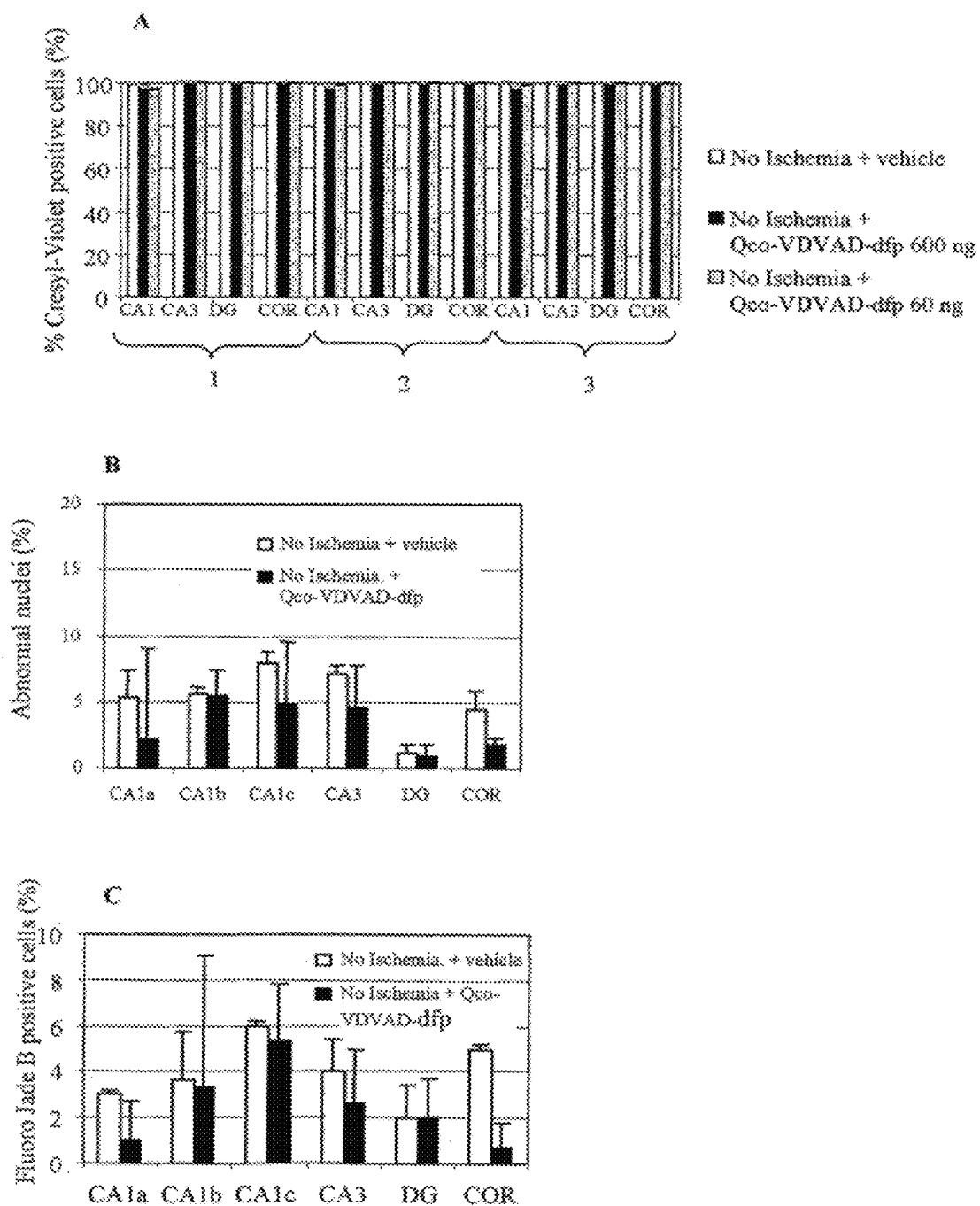

FIG. 7 shows no cell death (below basal threshold: 10%) in non-ischemic rats (icv) treated with 60-600 ng of Qco-VD-VAD-dfp (SEQ ID NO:1) whatever the level of observation in the hippocampus or in the cortex: absence of Cresyl-Violet negative cells, absence of abnormal nuclei, no Fluoro Jade B incorporation. Thus Qco-VDVAD-dfp (SEQ ID NO:1) is not topically tokic at 60-600 ng.

Figure 8:
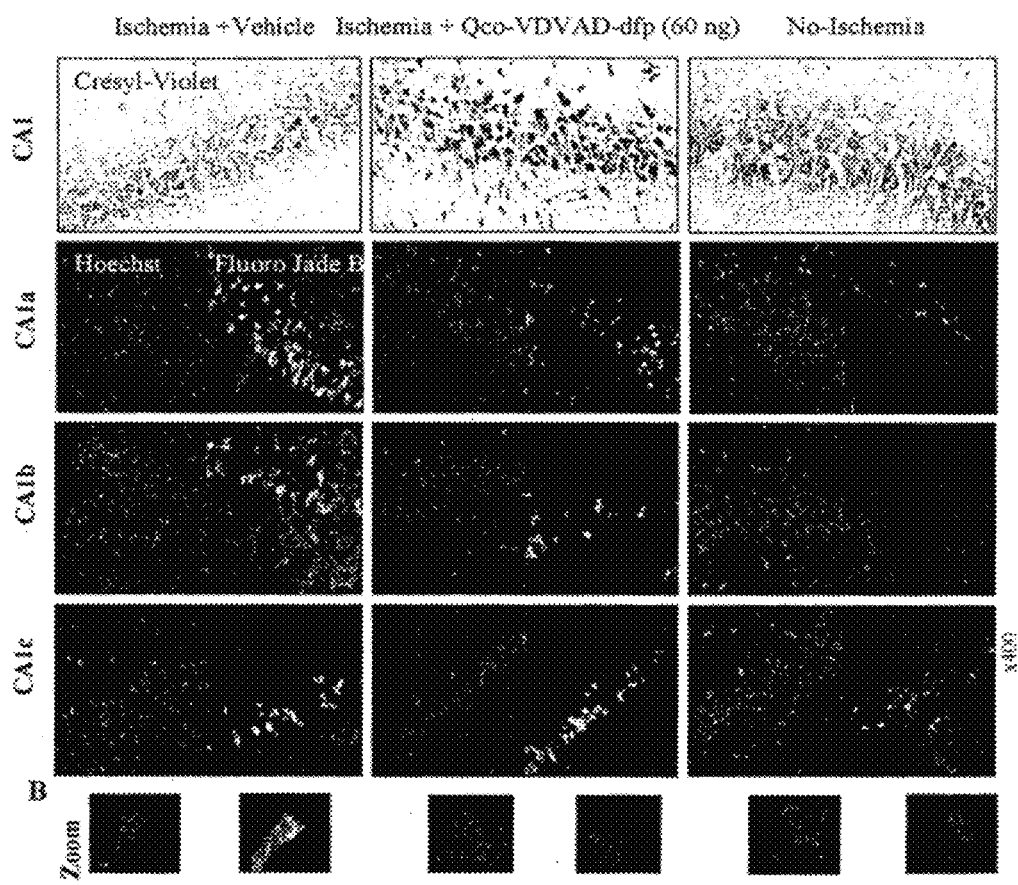
Figure 9:
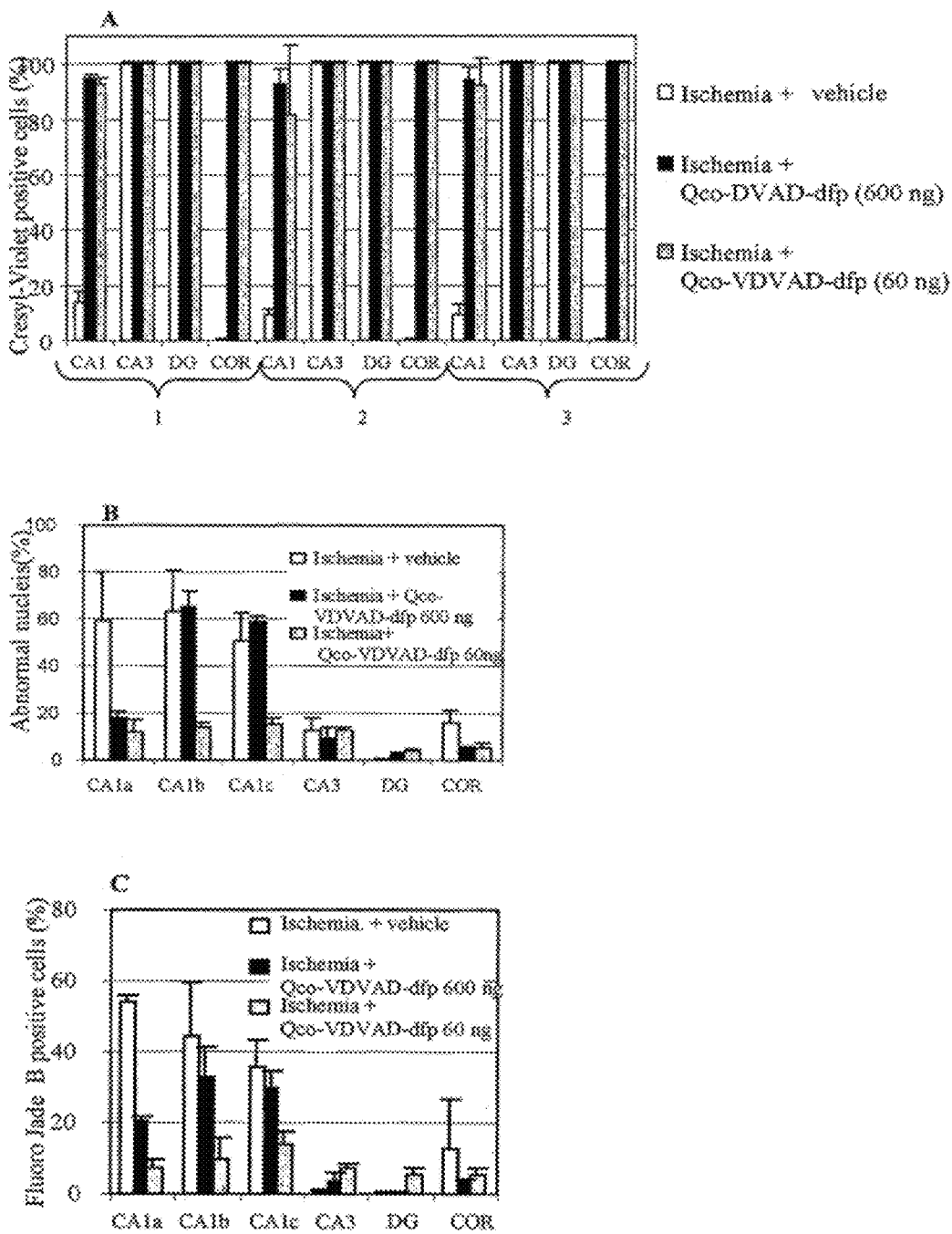

FIGS. 8-9 show the cytoprotective effects of Qco-VD-VAD-dfp (SEQ ID NO:1) at the level of CA1 in ischemic brains. In sharp contrast to ischemic rats, Qco-VDVAD-dfp's (SEQ ID NO:1) treated animals have less abnormal nuclei (nuclei were bigger and less retracted) and few cells incorporated Fluorojade B (between 10-20% instead of 50-60%). Thus colored slices looked like strongly to non-ischemic' ones. Moreover Cresyl-violet staining intensity was partially restored to the level of non-ischemic animal, but without total recovery of the cellular morphology.

Qco-VDVAD-dfp(SEQ ID NO:1)'s effects were independent of regulatory effects on temperature (FIG. 10).

Qco-VDVAD-dfp(SEQ ID NO:1)' have benefitory effects on the general behaviour of ischemic treated rat because these rats have a better scoring than untreated rats: they were more active, more reactive to noise and they fed them (FIG. 10).

These data are illustrated by the following figures:

FIG. 4: Cell death in hippocampus and cortex of ichemic rats (4VO) model.

A: Cell death in the hippocampus (CA1, CA3, DG) and cortex of 72 h post-ischemic adult rats. Global and transient cerebral ischemia was induced by 4 vessels occlusion (4VO; n=5). Rats were treated (icv) with DMSO (here, 7,255%; 0.7255% not shown). Slices are stained by Cresyl-Violet. B: Cell death in the hippocampus (CA1) of 72 h post-ischemic adult rats. Global and transient cerebral ischemia was induced by 4 vessels occlusion ((4VO; n=5). Rats were treated (icv) with DMSO (7,255%). Slices are stained by Hoechst 33432 (blue nuclei) and Fluoro Jade B (green nuclei and cytoplasm). C: High magnification of Hoechst and Fluoro Jade B fluorescence micrographs (size are increased by 2 and 6 folds, respectively). D: Microglial activation as a marker of ischemia. Microglial cells exhibit stick (resident microglia) or sickle (migrant microglia invading the brain after blood brain barrier rupture) shapes.

FIG. 5: Impact of ischemia on CA3, Dentus gyrus (DG) and cortex (COR). Cell death in the hippocampus (CA3, DG) and cortex (COR) at 72 h post-ischemia in adult rats. Global and transient cerebral ischemia was induced by 4 vessels occlusion ((4VO; n=5). Rats were treated (icv) with DMSO (here, 7,255%; 0.7255% not shown). Slices are co-stained by Fluoro Jade B/Hoechst at CA1 level (n=5).

FIG. 6: Quantitation of cell death at 72 h post-ischemia. Cell death in the hippocampus (CA1, CA3, DG,) and cortex (COR) at 72 h post-ischemia in adult rats. Global and transient cerebral ischemia was induced by 4 vessels occlusion ((4VO; n=5). Rats were treated (icv) with DMSO (here, 7.255%; 0.7255% not shown) (n=5). A: Quantitation of Cresyl-Violet positives cells at the level of injection of DMSO or TRP6 (1), 650 µm after (2) or 780 µm after (3). B: Quantitation of abnormal nuclei assessed by Hoechst staining in the hippocampus ($CA1_{a,b,c}$, CA3, DG) and cortex (COR) of ischemic and non-ischemic brains. C: Quantitation of FluoroJade B positive cells in the hippocampus ($CA1_{a,b,c}$, CA3, DG) and cortex (COR) of ischemic and non-ischemic brains.

FIG. 7: Non-toxicity of Qco-VDVAD-dfp (SEQ ID NO:1) in non-ischemic rats. Cell death in the hippocampus (CA1, CA3, DG,) and cortex (COR) at 72 h after icv administration of DMSO (here, 7.255%; 0.7255% not shown) or Qco-VDVAD-dfp (SEQ ID NO:1) (60 or 600 ng) (n=5) in non-ischemic rats. A: Quantitation of Cresyl-Violet positives cells in presence of increasing doses of TRP6 at the level of injection of DMSO or Qco-VDVAD-dfp (1), 650 µm after (2) or 780 µm after (3). B: Quantitation of abnormal nuclei assessed by Hoechst staining in the hippocampus ($CA1_{a,b,c}$, CA3, DG) and cortex (COR) of vehicle-trated of Qco-VDVAD-dfp (SEQ ID NO:1) treated rats. C: Quantitation of FluoroJade B positive cells in the hippocampus ($CA1_{a,b,c}$, CA3, DG) and cortex (COR) of ischemic and non-ischemic brains.

FIG. 8: Neuroprotection by Qco-VDVAD-dfp (SEQ ID NO:1) at 72 h post-ischemia (4VO) in the hippocampus of the young-adult rat. A: Microgaphs (×400) representative for CA1 and its sub-areas (CA1a, CA1b, CA1c) in vehicle-treated (DMSO 0.7255%) or Qco-VDVAD-dfp(SEQ ID NO:1)-treated (60 ng) ischemic rats versus non-ischemic animals (vehicle treated). Slices are stained with Cresyl-Violet (upper line), Hoechst (blue nuclei in left columns) or Fluoro Jade B (green fluorescence in right columns). B: High magnification (6 folds) of Hoechst and Fluoro Jade B fluorescence micrographs.

FIG. 9: Quantitative effect of Qco-VDVAD-dfp (SEQ ID NO:1) at 72 h post-ischemia. Cell death in the hippocampus (CA1, CA3, DG,) and cortex (COR) at 72 h post-ischemia in adult rats. Global and transient cerebral ischemia was induced by 4 vessels occlusion ((4VO; n=5). Rats were treated (icv) with DMSO (here, 7.255%; 0.7255% not shown) or Qco-VDVAD-dfp (60 or 600 ng) (n=5). A: Quantitation of Cresyl-Violet positives cells in presence of increasing doses of TRP6 at the level of injection of DMSO or Qco-VDVAD-dfp (SEQ ID NO:1) (1), 650 µm after (2) or 780 µm after (3). B: Quantitation of abnormal nuclei assessed by Hoechst staining in the hippocampus ($CA1_{a,b,c}$, CA3, DG) and cortex (COR) of vehicle-trated of Qco-VDVAD-dfp(SEQ ID NO:1)-treated rats. C: Quantitation of Fluoro Jade B positive cells in the hippocampus ($CA1_{a,b,c}$, CA3, DG) and cortex (COR) of ischemic and non-ischemic brains.

FIG. 10: Physiological and behavioural tests. A: Physiologial studies. Corporal temperature measurement from anesthesia to step 1 (vertebral electrocauterisation and cannula putting up) and step 2 (coratid isolation) of chirurgical procedure during day 1; 0, 10, 20 minutes after the beginning of ischemia at day 2; 24, 48, 72 H post-ischemia and before final anesthesia for perfusion at day 5. B: Behavioural studies: mean of parameters per group. Feeding: observation of stomacal contains at day 5, If refeeding=1, If no refeeding=0; Spontaneous activity: general behaviour of animals in their cage (alternance of active versus inactive phases) and reaction to prehension), Vivacity=1, More or less vivacious=0.5, No or poor vivacity=0; Reactivity: animal are sensitive and reactive to noise and move to the origin of the noise. If curious=1, If relatively curious=0.5, If not very curious=0.

C: Behavioural studies: total scoring (sum of total scores per group).

EXAMPLE

Obtention of Caspase-2 Inhibitors of Structure II

The main steps used for the synthesis are summarized on schemes 1 to 3. The percentage of reaction from compound 9 to compound 10 is 88%.

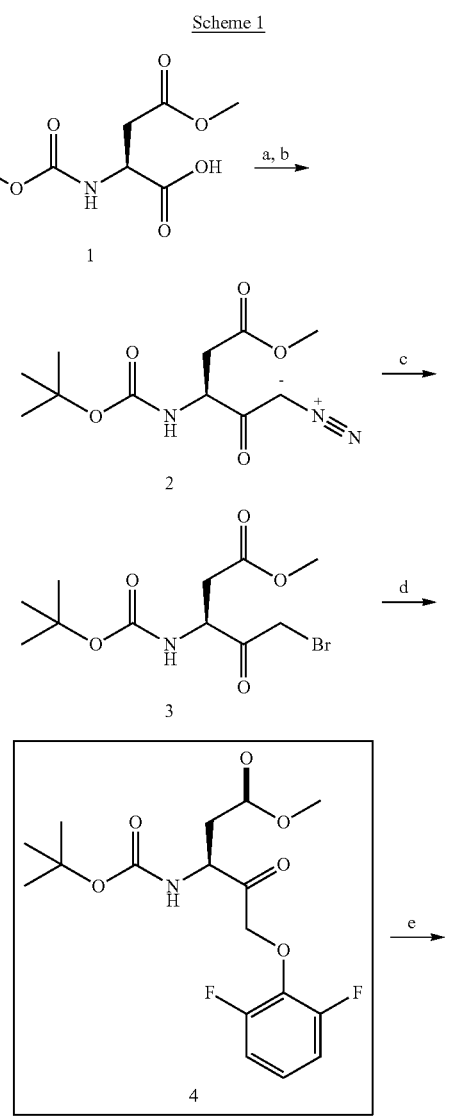

Scheme 1

Scheme 2
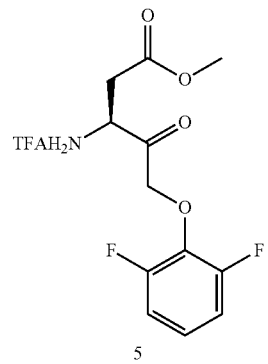
5
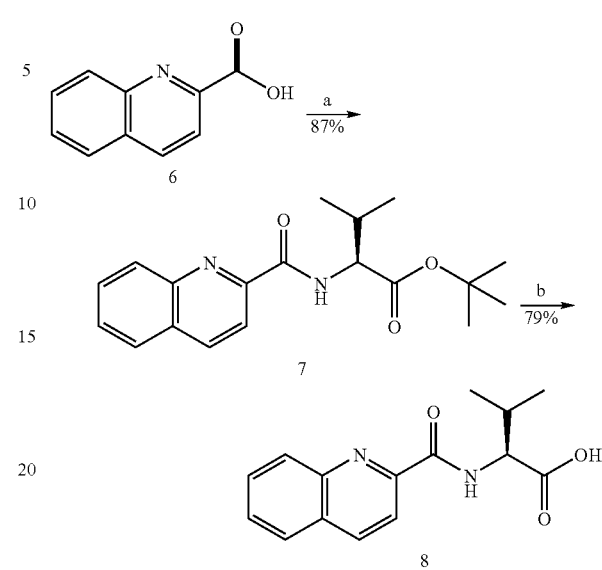
(a) THF, NMM, -15° C.
(b) EtOCOCl
(b) CH₂N₂.
(c) Et₂O, THF, HBr/AcOH.
(d) DMF, KF, 2,6-difluorophenol.
(e) TFA, DCM.
(a) DCC, HOBt, DIEA, DCM.
(b) TFA/DCM (1:1), reflux, 3 h.
Scheme 3
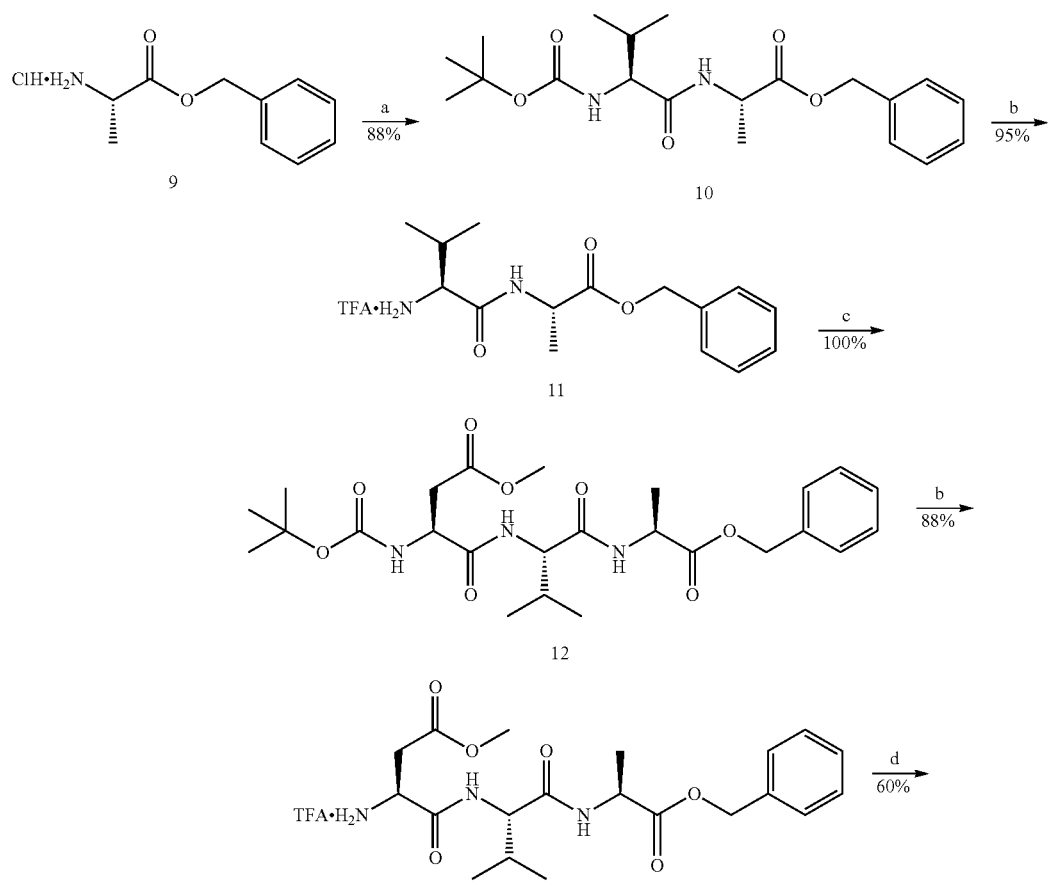

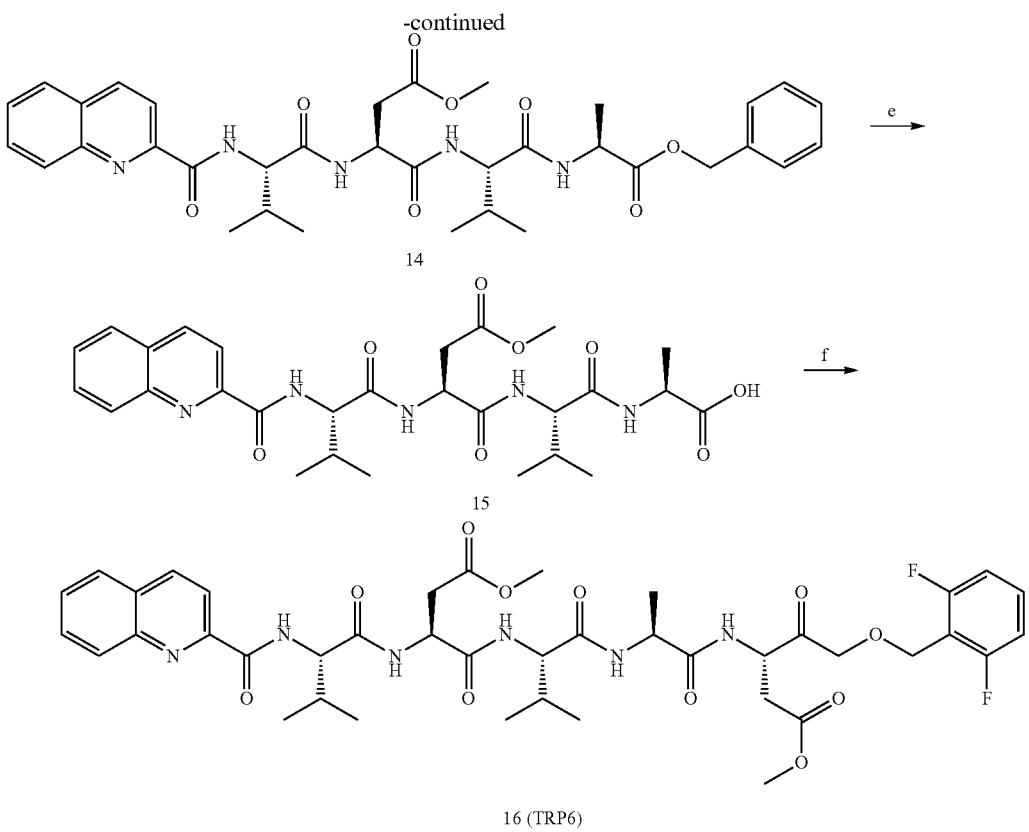

DIEA, Boc-Val-OH, DCC, HOBt.
(b) DCM/TFA (1:1), 1 h.
(c) DCM, DIEA, Boc-Asp(OMe)—OH, BOP, HOBt.
(d) DCM, DIEA, Qco-Val-OH, BOP, HOBt
(e) MeOH, cat. H₂, PdC, rt. 1-2 days.
(f) DCM, DIEA, TFA H-Asp(OMe)—CH₂—O-(2,6difluorophenyl), BOP, HOBt.

BIBLIOGRAPHIC REFERENCES

Pulsinelli W A, Waldman S, Rawlinson D, Plum F, Moderate hyperglycemia augments ischemic brain damage: a neuropathologic study in the rat. Neurology. 1982, 32:1239-1246.

Pulsinelli W. A., Buchman A. M. (1988). The Four-vessel Occlusion Rat Model: Method for Complete Occlusion of vertebral arteries and control of collateral circulation. Stroke. 19, 913-914

Renolleau, S., D. Aggoun-Zouaoui, Y. Ben-Ari, and C. Charriaut-Marlangue. 1998. A model of transient unilateral focal ischemia with reperfusion in the P7 neonatal rat: morphological changes indicative of apoptosis. Stroke 29: 1454-1461.

The invention claimed is:

1. A caspase-2 inhibitor with a structure of formula (Ia) or (Ib):

wherein n=1.

2. A caspase-2 inhibitor according to claim 1 having a structure of formula (II), wherein n=1:

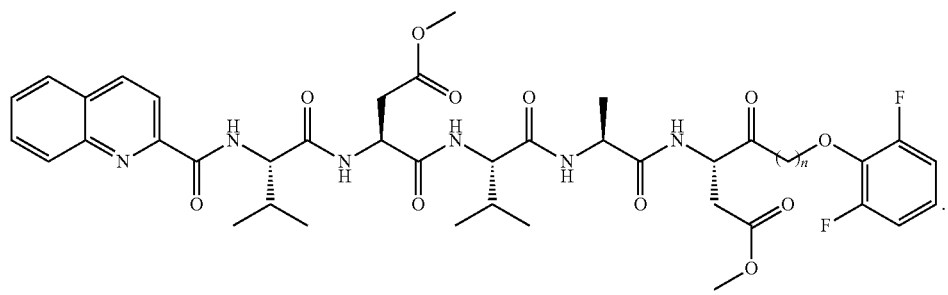

3. A pharmaceutical composition comprising an inhibitor of claim 1 or 2 optionally comprising a pharmaceutically acceptable carrier.

4. A method of blocking caspase-2 activity in cell death comprising administering a pharmaceutical composition according to claim 3, to a person in need of said blocking.

5. A method of neuroprotection or cerebroprotection comprising administering the pharmaceutical composition of claim 3, to a person in need of neuroprotective or cerebroprotective effect.

6. A method of cytoprotection comprising administering the pharmaceutical composition of claim 3, to a person in need of said cytoprotective effect.

7. A method of treating a person in need of treatment of a pathological condition selected from the group consisting of ischemic injuries following cerebral focal ischemia, ischemic injuries following cerebral focal ischemia as a consequence of MCAO, and ischemic injuries following cerebral focal ischemia as a consequence of strokes at birth or in the perinatal period, said method comprising administering the pharmaceutical composition of claim 3 to the person.

* * * * *

```
                        SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: NON_TER
<222> LOCATION: (1)..(1)
<223> OTHER INFORMATION: This residue is not the N-terminus of the
      complete molecule
<220> FEATURE:
```

```
<221> NAME/KEY: MOD_RES
<222> LOCATION: (2)..(2)
<223> OTHER INFORMATION: Methyl ester modified Asp
<220> FEATURE:
<221> NAME/KEY: MOD_RES
<222> LOCATION: (5)..(5)
<223> OTHER INFORMATION: Methyl ester modified Asp
<220> FEATURE:
<221> NAME/KEY: NON_TER
<222> LOCATION: (5)..(5)
<223> OTHER INFORMATION: This residue is not the C-terminus of the
      complete molecule

<400> SEQUENCE: 1

Val Asp Val Ala Asp
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Asp Glu Ser Asp
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Val Ala Asp
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Glu Val Asp
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Glu His Asp
1

<210> SEQ ID NO 6
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 6

Val Glu Ile Asp
1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Glu Thr Asp
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Glu His Asp
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Asp Val Ala Asp
1               5
```